(12) United States Patent
Rubin-Wilson et al.

(10) Patent No.: US 6,323,395 B1
(45) Date of Patent: Nov. 27, 2001

(54) NUCLEOTIDE SEQUENCES OF MAIZE AND SOYBEAN β-KETOACYL-ACYL CARRIER PROTEIN SYNTHASE II AND THEIR USE IN THE REGULATION OF FATTY ACID CONTENT OF OIL

(75) Inventors: Beth C. Rubin-Wilson; Scott A. Young, both of Indianapolis, IN (US); Otto Folkerts, Guilford, CT (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/212,609

(22) Filed: Dec. 16, 1998

Related U.S. Application Data

(60) Provisional application No. 60/068,784, filed on Dec. 24, 1997.

(51) Int. Cl.[7] ............................... A01H 1/00; A01H 1/02; C12N 15/82; C12N 5/02; C07H 21/04

(52) U.S. Cl. ........................ 800/281; 800/285; 800/286; 800/295; 800/298; 435/6; 435/183; 435/320.1; 435/410; 435/440; 536/23.1; 536/23.2; 536/23.6

(58) Field of Search ................................. 536/23.1, 23.6, 536/24.1, 23.2; 530/350, 378, 377, 376; 435/69.1, 6, 320.1, 71.1, 410, 440; 800/264, 298, 295, 281

(56) References Cited

U.S. PATENT DOCUMENTS 5,475,099 * 12/1995 Knauf et al. ..................... 536/23.6
5,510,255 * 4/1996 Knauf et al. .................... 435/172.3

* cited by examiner

*Primary Examiner*—John L. LeGuyader
*Assistant Examiner*—Janet Epps
(74) *Attorney, Agent, or Firm*—Donald R. Stuart

(57) ABSTRACT

Genes encoding β-Ketoacyl-Acyl Carrier Protein Synthase II have been isolated from maize and soybean tissues. These proteins, when expressed in a plant, can alter the saturate levels of the oil.

22 Claims, No Drawings

SEQUENCE LISTING

```
<160> NUMBER OF SEQ ID NOS: 29

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:5' primer
      with 256-fold degeneracy
<221> NAME/KEY: unsure
<222> LOCATION: (6)
<223> OTHER INFORMATION: a, t, c, or g
<221> NAME/KEY: unsure
<222> LOCATION: (12)
<223> OTHER INFORMATION: a, t, c, or g
<221> NAME/KEY: unsure
<222> LOCATION: (18)
<223> OTHER INFORMATION: a, t, c, or g

<400> SEQUENCE: 1
gayggnttyg tnatgggnga                                               20

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:3' primer
      with 256 fold degeneracy
<221> NAME/KEY: unsure
<222> LOCATION: (3)
<223> OTHER INFORMATION: a, t, c, or g
<221> NAME/KEY: unsure
<222> LOCATION: (6)
<223> OTHER INFORMATION: a, t, c, or g
<221> NAME/KEY: unsure
<222> LOCATION: (12)
<223> OTHER INFORMATION: a, t, c, or g

<400> SEQUENCE: 2
tgnccnccra anccraa                                                  17

<210> SEQ ID NO 3
<211> LENGTH: 527
<212> TYPE: DNA
<213> ORGANISM: Zea mays
<220> FEATURE:
<221> NAME/KEY: CDS
<222> LOCATION: (1)..(525)

<400> SEQUENCE: 3 gat ggt ttt gtt atg ggg gaa ggg gct ggt gtc ctc gta ttg gaa gaa    48
Asp Gly Phe Val Met Gly Glu Gly Ala Gly Val Leu Val Leu Glu Glu
  1               5                  10                  15 ctt gag cat gcc aag gaa aga ggt gca aca ata tat gct gaa ttt ctt    96
Leu Glu His Ala Lys Glu Arg Gly Ala Thr Ile Tyr Ala Glu Phe Leu
             20                  25                  30 ggt gga agc ttc aca tgt gat gct tac cac atg act gag cca cat cct   144
Gly Gly Ser Phe Thr Cys Asp Ala Tyr His Met Thr Glu Pro His Pro
         35                  40                  45
```

```
gaa gga aga ggg att gct ctc tgc atc gaa aag gca cta gct gat gca     192
Glu Gly Arg Gly Ile Ala Leu Cys Ile Glu Lys Ala Leu Ala Asp Ala
        50                  55                  60 ggg gta gca agg gaa gaa atc aac tac gtg aat gcc cat gca aca tct     240
Gly Val Ala Arg Glu Glu Ile Asn Tyr Val Asn Ala His Ala Thr Ser
 65                  70                  75                  80 aca caa gca ggt gac ttg aag gag tat gag gct atc gtg cgc tgt ttt     288
Thr Gln Ala Gly Asp Leu Lys Glu Tyr Glu Ala Ile Val Arg Cys Phe
                 85                  90                  95 cgc cag aac cct caa ctg agg gtg aac tcg acc aaa tca atg act ggg     336
Arg Gln Asn Pro Gln Leu Arg Val Asn Ser Thr Lys Ser Met Thr Gly
            100                 105                 110 cat ctt ata gga gca gct ggt gga ata gaa gca gtt gct tct ata caa     384
His Leu Ile Gly Ala Ala Gly Gly Ile Glu Ala Val Ala Ser Ile Gln
        115                 120                 125 gct ata aga act ggt tgg gtc cat cca aat ttg aat tta gaa aat cca     432
Ala Ile Arg Thr Gly Trp Val His Pro Asn Leu Asn Leu Glu Asn Pro
130                 135                 140 gag gac acc gtg gac gtg ggc gtc ttg gta ggg tca cag aag gag aga     480
Glu Asp Thr Val Asp Val Gly Val Leu Val Gly Ser Gln Lys Glu Arg
145                 150                 155                 160 tgt gaa gtg aag gtg gcg ttg tcc aac tca ttc gga ttc ggt ggg ca      527
Cys Glu Val Lys Val Ala Leu Ser Asn Ser Phe Gly Phe Gly Gly
                165                 170                 175

<210> SEQ ID NO 4
<211> LENGTH: 175
<212> TYPE: PRT
<213> ORGANISM: Zea mays

<400> SEQUENCE: 4

Asp Gly Phe Val Met Gly Glu Gly Ala Gly Val Leu Val Leu Glu Glu
 1               5                  10                  15

Leu Glu His Ala Lys Glu Arg Gly Ala Thr Ile Tyr Ala Glu Phe Leu
                20                  25                  30

Gly Gly Ser Phe Thr Cys Asp Ala Tyr His Met Thr Glu Pro His Pro
            35                  40                  45

Glu Gly Arg Gly Ile Ala Leu Cys Ile Glu Lys Ala Leu Ala Asp Ala
        50                  55                  60

Gly Val Ala Arg Glu Glu Ile Asn Tyr Val Asn Ala His Ala Thr Ser
 65                  70                  75                  80

Thr Gln Ala Gly Asp Leu Lys Glu Tyr Glu Ala Ile Val Arg Cys Phe
                 85                  90                  95

Arg Gln Asn Pro Gln Leu Arg Val Asn Ser Thr Lys Ser Met Thr Gly
            100                 105                 110

His Leu Ile Gly Ala Ala Gly Gly Ile Glu Ala Val Ala Ser Ile Gln
        115                 120                 125

Ala Ile Arg Thr Gly Trp Val His Pro Asn Leu Asn Leu Glu Asn Pro
130                 135                 140

Glu Asp Thr Val Asp Val Gly Val Leu Val Gly Ser Gln Lys Glu Arg
145                 150                 155                 160

Cys Glu Val Lys Val Ala Leu Ser Asn Ser Phe Gly Phe Gly Gly
                165                 170                 175

<210> SEQ ID NO 5
<211> LENGTH: 2058
<212> TYPE: DNA
<213> ORGANISM: Zea mays
```

```
<220> FEATURE:
<221> NAME/KEY: CDS
<222> LOCATION: (30)..(1517)
<221> NAME/KEY: mat_peptide
<222> LOCATION: (219)..(1517)

<400> SEQUENCE: 5
cggcacgagc ggcacgaggg aggggggca atg gcg gcc gtg gca ggc cca ctc         53
                                Met Ala Ala Val Ala Gly Pro Leu
                                    -60 tgc acg tgg ctc gtc gcc gcg tgc tta tct gcg gca tgc gac gct gaa        101
Cys Thr Trp Leu Val Ala Ala Cys Leu Ser Ala Ala Cys Asp Ala Glu
-55             -50                 -45                 -40 gag cac aag cag aag cat ttc tgc gca ggc gga agc cgc gct ggg ggc        149
Glu His Lys Gln Lys His Phe Cys Ala Gly Gly Ser Arg Ala Gly Gly
            -35                 -30                 -25 ggt gtc atg ctc ggc cag cgc cgc ctc ggc gcg cgg cgt cgc ggc            197
Gly Val Met Leu Gly Gln Arg Arg Leu Gly Ala Arg Arg Arg Gly
        -20                 -15                 -10 ttg gcg cgc tct gga atg act atg gct gtt gcc tta caa gct gaa aga        245
Leu Ala Arg Ser Gly Met Thr Met Ala Val Ala Leu Gln Ala Glu Arg
    -5                  -1   1                5 agt gtc att gaa aag aag aaa ccc gat atc aaa caa agg agg gtg gtt        293
Ser Val Ile Glu Lys Lys Lys Pro Asp Ile Lys Gln Arg Arg Val Val
 10              15                  20                  25 gtc act ggc atg ggt gta gtg aca cca ttg ggc cat gat cct gac gtg        341
Val Thr Gly Met Gly Val Val Thr Pro Leu Gly His Asp Pro Asp Val
                 30                  35                  40 ttt tac aac aat ctt ctt gat ggt gtt agc gga ata agt gag att gag        389
Phe Tyr Asn Asn Leu Leu Asp Gly Val Ser Gly Ile Ser Glu Ile Glu
             45                  50                  55 agg ttt gac tgt tcc aac ttc ccc acg aga att gca gga gag ata aaa        437
Arg Phe Asp Cys Ser Asn Phe Pro Thr Arg Ile Ala Gly Glu Ile Lys
         60                  65                  70 tcc ttc tct act gat ggt tgg gtt gca cct aaa ctt gca aag cgg atg        485
Ser Phe Ser Thr Asp Gly Trp Val Ala Pro Lys Leu Ala Lys Arg Met
     75                  80                  85 gac aag ttt atg cta tat ctg ata act gct gga aag aag gca tta gaa        533
Asp Lys Phe Met Leu Tyr Leu Ile Thr Ala Gly Lys Lys Ala Leu Glu
 90                  95                 100                 105 aat ggt gga ctc act gaa gaa cta agg aat gag ttg gac aaa acc agg        581
Asn Gly Gly Leu Thr Glu Glu Leu Arg Asn Glu Leu Asp Lys Thr Arg
                 110                 115                 120 tgt ggg gtt ctt att ggt tct gca atg ggt ggc atg aag gtt ttt aat        629
Cys Gly Val Leu Ile Gly Ser Ala Met Gly Gly Met Lys Val Phe Asn
             125                 130                 135 gat gca att gaa gca ctg agg gtc tct tac aag aaa atg aac cca ttt        677
Asp Ala Ile Glu Ala Leu Arg Val Ser Tyr Lys Lys Met Asn Pro Phe
         140                 145                 150 tgt gtt cct ttt gca act acg aat atg ggc tct gcg atc ctt gca atg        725
Cys Val Pro Phe Ala Thr Thr Asn Met Gly Ser Ala Ile Leu Ala Met
    155                 160                 165 gat ctg gga tgg atg gga cca aac tat tct att tcc aca gct tgt gct        773
Asp Leu Gly Trp Met Gly Pro Asn Tyr Ser Ile Ser Thr Ala Cys Ala
170                 175                 180                 185 acc agt aac ttc tgt atc ctt aat gca gca aac cac atc aga aga ggc        821
Thr Ser Asn Phe Cys Ile Leu Asn Ala Ala Asn His Ile Arg Arg Gly
                190                 195                 200 gaa gct gac gtt atg ctc tgc ggt ggt tct gat gca cct ctt atc cca        869
Glu Ala Asp Val Met Leu Cys Gly Gly Ser Asp Ala Pro Leu Ile Pro
            205                 210                 215
```

```
atc gga ttg gga ggt ttt gtg gca tgc aga gct ctt tca cag agg aac      917
Ile Gly Leu Gly Gly Phe Val Ala Cys Arg Ala Leu Ser Gln Arg Asn
            220                 225                 230 agt gac cca aca aaa gct tct cgg cct tgg gac atg gga cgt gat ggt      965
Ser Asp Pro Thr Lys Ala Ser Arg Pro Trp Asp Met Gly Arg Asp Gly
235                 240                 245 ttt gtt atg ggg gaa ggg gct ggt gtc ctc gta ttg gaa gaa ctt gag     1013
Phe Val Met Gly Glu Gly Ala Gly Val Leu Leu Glu Glu Leu Glu
250                 255                 260                 265 cat gcc aag gaa aga ggt gca aca ata tat gct gaa ttt ctt ggt gga     1061
His Ala Lys Glu Arg Gly Ala Thr Ile Tyr Ala Glu Phe Leu Gly Gly
                270                 275                 280 agc ttc aca tgt gat gct tac cac atg act gag cca cat cct gaa gga     1109
Ser Phe Thr Cys Asp Ala Tyr His Met Thr Glu Pro His Pro Glu Gly
            285                 290                 295 aga ggg att gct ctc tgc atc gaa aag gca cta gct gat gca ggg gta     1157
Arg Gly Ile Ala Leu Cys Ile Glu Lys Ala Leu Ala Asp Ala Gly Val
        300                 305                 310 gca agg gaa gaa atc aac tac gtg aat gcc cat gca aca tct aca caa     1205
Ala Arg Glu Glu Ile Asn Tyr Val Asn Ala His Ala Thr Ser Thr Gln
315                 320                 325 gca ggt gac ttg aag gag tat gag gct atc gtg cgc tgt ttt cgc cag     1253
Ala Gly Asp Leu Lys Glu Tyr Glu Ala Ile Val Arg Cys Phe Arg Gln
330                 335                 340                 345 aac cct caa ctg agg gtg aac tcg acc aaa tca atg act ggg cat ctt     1301
Asn Pro Gln Leu Arg Val Asn Ser Thr Lys Ser Met Thr Gly His Leu
                350                 355                 360 ata gga gca gct ggt gga ata gaa gca gtt gct tct ata caa gct ata     1349
Ile Gly Ala Ala Gly Gly Ile Glu Ala Val Ala Ser Ile Gln Ala Ile
            365                 370                 375 aga act ggt tgg gtc cat cca aat ttg aat tta gaa aat cca gag gac     1397
Arg Thr Gly Trp Val His Pro Asn Leu Asn Leu Glu Asn Pro Glu Asp
        380                 385                 390 acc gtg gac gtg ggc gtc ttg gta ggg tca cag aag gag aga tgt gaa     1445
Thr Val Asp Val Gly Val Leu Val Gly Ser Gln Lys Glu Arg Cys Glu
395                 400                 405 gtg aag gtg gcg ttg tcc aac tca ttc gga ttc ggt ggg cac aac tca     1493
Val Lys Val Ala Leu Ser Asn Ser Phe Gly Phe Gly Gly His Asn Ser
410                 415                 420                 425 tcg att ctc ttt gcc ccc ttt aag tgaacatgac cgaggcgaag aaccgacatc   1547
Ser Ile Leu Phe Ala Pro Phe Lys
                430 ttcatcatcg cgcaaatggc ttcatatatc tggaactcca catagaaatc tggtggattc   1607 tgcaacttcc tccgtgccac acatactgca tatggaggtc caaagtgagg gtacaatact   1667 atgccacaca catttgagcg aacaaaacat cagccccct acatgtttca tctactatca    1727 caaagttgca aaatatatat ggtaactatc aaagaactta ccgtacctgg gccagtgttt   1787 tcgccttcac catacctgcc cattgtcagt actatttcct acatttggtg tagtcccgta   1847 gcttaatcct cttccctgcg gaggtgatgg gatcttatgt tgtattgttg ttgccaacag   1907 tatcgttatt agccatgaat tgctggttcc cactgtaagc atcactggac gttttcgctt   1967 tggttgtttc tgtttcctgc tgttcataac cgagttaaag atatgtaaat ggcgaccctg   2027 ttcggccttt aatcaaaaaa aaaaaaaaaa a                                   2058

<210> SEQ ID NO 6
<211> LENGTH: 496
<212> TYPE: PRT
```

```
<213> ORGANISM: Zea mays

<400> SEQUENCE: 6

Met Ala Val Ala Gly Pro Leu Cys Thr Trp Leu Val Ala Cys
        -60             -55             -50

Leu Ser Ala Ala Cys Asp Ala Glu Glu His Lys Gln Lys His Phe Cys
        -45             -40                 -35

Ala Gly Gly Ser Arg Ala Gly Gly Val Met Leu Gly Gln Arg Arg
        -30             -25             -20

Arg Leu Gly Ala Arg Arg Arg Gly Leu Ala Arg Ser Gly Met Thr Met
-15                 -10                 -5                  -1   1

Ala Val Ala Leu Gln Ala Glu Arg Ser Val Ile Glu Lys Lys Pro
                5                   10                  15

Asp Ile Lys Gln Arg Arg Val Val Thr Gly Met Gly Val Val Thr
            20                  25                  30

Pro Leu Gly His Asp Pro Asp Val Phe Tyr Asn Asn Leu Leu Asp Gly
            35                  40                  45

Val Ser Gly Ile Ser Glu Ile Glu Arg Phe Asp Cys Ser Asn Phe Pro
50                  55                  60                  65

Thr Arg Ile Ala Gly Glu Ile Lys Ser Phe Ser Thr Asp Gly Trp Val
                70                  75                  80

Ala Pro Lys Leu Ala Lys Arg Met Asp Lys Phe Met Leu Tyr Leu Ile
                85                  90                  95

Thr Ala Gly Lys Lys Ala Leu Glu Asn Gly Gly Leu Thr Glu Glu Leu
                100                 105                 110

Arg Asn Glu Leu Asp Lys Thr Arg Cys Gly Val Leu Ile Gly Ser Ala
115                 120                 125

Met Gly Gly Met Lys Val Phe Asn Asp Ala Ile Glu Ala Leu Arg Val
130                 135                 140                 145

Ser Tyr Lys Lys Met Asn Pro Phe Cys Val Pro Phe Ala Thr Thr Asn
                150                 155                 160

Met Gly Ser Ala Ile Leu Ala Met Asp Leu Gly Trp Met Gly Pro Asn
                165                 170                 175

Tyr Ser Ile Ser Thr Ala Cys Ala Thr Ser Asn Phe Cys Ile Leu Asn
                180                 185                 190

Ala Ala Asn His Ile Arg Arg Gly Glu Ala Asp Val Met Leu Cys Gly
195                 200                 205

Gly Ser Asp Ala Pro Leu Ile Pro Ile Gly Leu Gly Gly Phe Val Ala
210                 215                 220                 225

Cys Arg Ala Leu Ser Gln Arg Asn Ser Asp Pro Thr Lys Ala Ser Arg
                230                 235                 240

Pro Trp Asp Met Gly Arg Asp Gly Phe Val Met Gly Glu Gly Ala Gly
                245                 250                 255

Val Leu Val Leu Glu Glu Leu Glu His Ala Lys Glu Arg Gly Ala Thr
            260                 265                 270

Ile Tyr Ala Glu Phe Leu Gly Gly Ser Phe Thr Cys Asp Ala Tyr His
            275                 280                 285

Met Thr Glu Pro His Pro Glu Gly Arg Gly Ile Ala Leu Cys Ile Glu
290                 295                 300                 305

Lys Ala Leu Ala Asp Ala Gly Val Ala Arg Glu Ile Asn Tyr Val
                310                 315                 320

Asn Ala His Ala Thr Ser Thr Gln Ala Gly Asp Leu Lys Glu Tyr Glu
                325                 330                 335
```

-continued

```
Ala Ile Val Arg Cys Phe Arg Gln Asn Pro Gln Leu Arg Val Asn Ser
        340                 345                 350
Thr Lys Ser Met Thr Gly His Leu Ile Gly Ala Ala Gly Gly Ile Glu
    355                 360                 365
Ala Val Ala Ser Ile Gln Ala Ile Arg Thr Gly Trp Val His Pro Asn
370                 375                 380                 385
Leu Asn Leu Glu Asn Pro Glu Asp Thr Val Asp Val Gly Val Leu Val
                390                 395                 400
Gly Ser Gln Lys Glu Arg Cys Glu Val Lys Val Ala Leu Ser Asn Ser
                405                 410                 415
Phe Gly Phe Gly Gly His Asn Ser Ser Ile Leu Phe Ala Pro Phe Lys
            420                 425                 430
```

<210> SEQ ID NO 7
<211> LENGTH: 1491
<212> TYPE: DNA
<213> ORGANISM: Zea mays
<220> FEATURE:
<221> NAME/KEY: CDS
<222> LOCATION: (1)..(1488)
<221> NAME/KEY: mat_peptide
<222> LOCATION: (190)..(1488)

<400> SEQUENCE: 7

```
atg gcg gcc gtg gca ggc cca ctc tgc acg tgg ctc gtc gcc gcg tgc      48
Met Ala Ala Val Ala Gly Pro Leu Cys Thr Trp Leu Val Ala Ala Cys
            -60                 -55                 -50 tta tct gcg gca tgc gac gct gaa gag cac aag cag aag cat ttc tgc      96
Leu Ser Ala Ala Cys Asp Ala Glu Glu His Lys Gln Lys His Phe Cys
        -45                 -40                 -35 gca ggc gga agc cgc gct ggg ggc ggt gtc atg ctc ggc cag cgc cgc     144
Ala Gly Gly Ser Arg Ala Gly Gly Gly Val Met Leu Gly Gln Arg Arg
    -30                 -25                 -20 cgc ctc ggc gcg cgg cgt cgc ggc ttg gcg cgc tct gga atg act atg     192
Arg Leu Gly Ala Arg Arg Arg Gly Leu Ala Arg Ser Gly Met Thr Met
-15                 -10                 -5                  -1   1 gct gtt gcc tta caa gct gaa aga agt gtc att gaa aag aag aaa ccc     240
Ala Val Ala Leu Gln Ala Glu Arg Ser Val Ile Glu Lys Lys Lys Pro
            5                   10                  15 gat atc aaa caa agg agg gtg gtt gtc act ggc atg ggt gta gtg aca     288
Asp Ile Lys Gln Arg Arg Val Val Val Thr Gly Met Gly Val Val Thr
        20                  25                  30 cca ttg ggc cat gat cct gac gtg ttt tac aac aat ctt ctt gat ggt     336
Pro Leu Gly His Asp Pro Asp Val Phe Tyr Asn Asn Leu Leu Asp Gly
    35                  40                  45 gtt agc gga ata agt gag att gag agg ttt gac tgt tcc aac ttc ccc     384
Val Ser Gly Ile Ser Glu Ile Glu Arg Phe Asp Cys Ser Asn Phe Pro
50                  55                  60                  65 acg aga att gca gga gag ata aaa tcc ttc tct act gat ggt tgg gtt     432
Thr Arg Ile Ala Gly Glu Ile Lys Ser Phe Ser Thr Asp Gly Trp Val
                70                  75                  80 gca cct aaa ctt gca aag cgg atg gac aag ttt atg cta tat ctg ata     480
Ala Pro Lys Leu Ala Lys Arg Met Asp Lys Phe Met Leu Tyr Leu Ile
            85                  90                  95 act gct gga aag aag gca tta gaa aat ggt gga ctc act gaa gaa cta     528
Thr Ala Gly Lys Lys Ala Leu Glu Asn Gly Gly Leu Thr Glu Glu Leu
        100                 105                 110 agg aat gag ttg gac aaa acc agg tgt ggg gtt ctt att ggt tct gca     576
Arg Asn Glu Leu Asp Lys Thr Arg Cys Gly Val Leu Ile Gly Ser Ala
    115                 120                 125
```

```
                                                -continued atg ggt ggc atg aag gtt ttt aat gat gca att gaa gca ctg agg gtc    624
Met Gly Gly Met Lys Val Phe Asn Asp Ala Ile Glu Ala Leu Arg Val
130                 135                 140                 145 tct tac aag aaa atg aac cca ttt tgt gtt cct ttt gca act acg aat    672
Ser Tyr Lys Lys Met Asn Pro Phe Cys Val Pro Phe Ala Thr Thr Asn
                150                 155                 160 atg ggc tct gcg atc ctt gca atg gat ctg gga tgg atg gga cca aac    720
Met Gly Ser Ala Ile Leu Ala Met Asp Leu Gly Trp Met Gly Pro Asn
            165                 170                 175 tat tct att tcc aca gct tgt gct acc agt aac ttc tgt atc ctt aat    768
Tyr Ser Ile Ser Thr Ala Cys Ala Thr Ser Asn Phe Cys Ile Leu Asn
        180                 185                 190 gca gca aac cac atc aga aga ggc gaa gct gac gtt atg ctc tgc ggt    816
Ala Ala Asn His Ile Arg Arg Gly Glu Ala Asp Val Met Leu Cys Gly
    195                 200                 205 ggt tct gat gca cct ctt atc cca atc gga ttg gga ggt ttt gtg gca    864
Gly Ser Asp Ala Pro Leu Ile Pro Ile Gly Leu Gly Gly Phe Val Ala
210                 215                 220                 225 tgc aga gct ctt tca cag agg aac agt gac cca aca aaa gct tct cgg    912
Cys Arg Ala Leu Ser Gln Arg Asn Ser Asp Pro Thr Lys Ala Ser Arg
                230                 235                 240 cct tgg gac atg gga cgt gat ggt ttt gtt atg ggg gaa ggg gct ggt    960
Pro Trp Asp Met Gly Arg Asp Gly Phe Val Met Gly Glu Gly Ala Gly
            245                 250                 255 gtc ctc gta ttg gaa gaa ctt gag cat gcc aag gaa aga ggt gca aca   1008
Val Leu Val Leu Glu Glu Leu Glu His Ala Lys Glu Arg Gly Ala Thr
        260                 265                 270 ata tat gct gaa ttt ctt ggt gga agc ttc aca tgt gat gct tac cac   1056
Ile Tyr Ala Glu Phe Leu Gly Gly Ser Phe Thr Cys Asp Ala Tyr His
    275                 280                 285 atg act gag cca cat cct gaa gga aga ggg att gct ctc tgc atc gaa   1104
Met Thr Glu Pro His Pro Glu Gly Arg Gly Ile Ala Leu Cys Ile Glu
290                 295                 300                 305 aag gca cta gct gat gca ggg gta gca agg gaa gaa atc aac tac gtg   1152
Lys Ala Leu Ala Asp Ala Gly Val Ala Arg Glu Glu Ile Asn Tyr Val
                310                 315                 320 aat gcc cat gca aca tct aca caa gca ggt gac ttg aag gag tat gag   1200
Asn Ala His Ala Thr Ser Thr Gln Ala Gly Asp Leu Lys Glu Tyr Glu
            325                 330                 335 gct atc gtg cgc tgt ttc cgc cag aac cct caa ctg agg gtg aac tcg   1248
Ala Ile Val Arg Cys Phe Arg Gln Asn Pro Gln Leu Arg Val Asn Ser
        340                 345                 350 acc aaa tca atg act ggg cat ctt ata gga gca gct ggt gga ata gaa   1296
Thr Lys Ser Met Thr Gly His Leu Ile Gly Ala Ala Gly Gly Ile Glu
    355                 360                 365 gca gtt gct tct ata caa gct ata aga act ggt tgg gtc cat cca aat   1344
Ala Val Ala Ser Ile Gln Ala Ile Arg Thr Gly Trp Val His Pro Asn
370                 375                 380                 385 ttg aat tta gaa aat cca gag gac acc gtg gac gtg ggc gtc ttg gta   1392
Leu Asn Leu Glu Asn Pro Glu Asp Thr Val Asp Val Gly Val Leu Val
                390                 395                 400 ggg tca cag aag gag aga tgt gaa gtg aag gtg gcg ttg tcc aac tca   1440
Gly Ser Gln Lys Glu Arg Cys Glu Val Lys Val Ala Leu Ser Asn Ser
            405                 410                 415 ttc gga ttc ggt ggg cac aac tca tcg att ctc ttt gcc ccc ttt aag   1488
Phe Gly Phe Gly Gly His Asn Ser Ser Ile Leu Phe Ala Pro Phe Lys
        420                 425                 430 tga                                                               1491
```

<210> SEQ ID NO 8
<211> LENGTH: 1302
<212> TYPE: DNA
<213> ORGANISM: Zea mays
<220> FEATURE:
<221> NAME/KEY: CDS
<222> LOCATION: (1)..(1299)

<400> SEQUENCE: 8

| | | | | | | | | | | | | | | | | |
|---|---|---|---|---|---|---|---|---|---|---|---|---|---|---|---|---|
| atg | gct | gtt | gcc | tta | caa | gct | gaa | aga | agt | gtc | att | gaa | aag | aag | aaa | 48 |
| Met | Ala | Val | Ala | Leu | Gln | Ala | Glu | Arg | Ser | Val | Ile | Glu | Lys | Lys | Lys | |
| 1 | | | | 5 | | | | | 10 | | | | | 15 | | |
| ccc | gat | atc | aaa | caa | agg | agg | gtg | gtt | gtc | act | ggc | atg | ggt | gta | gtg | 96 |
| Pro | Asp | Ile | Lys | Gln | Arg | Arg | Val | Val | Val | Thr | Gly | Met | Gly | Val | Val | |
| | | | 20 | | | | | 25 | | | | | 30 | | | |
| aca | cca | ttg | ggc | cat | gat | cct | gac | gtg | ttt | tac | aac | aat | ctt | ctt | gat | 144 |
| Thr | Pro | Leu | Gly | His | Asp | Pro | Asp | Val | Phe | Tyr | Asn | Asn | Leu | Leu | Asp | |
| | | 35 | | | | | 40 | | | | | 45 | | | | |
| ggt | gtt | agc | gga | ata | agt | gag | att | gag | agg | ttt | gac | tgt | tcc | aac | ttc | 192 |
| Gly | Val | Ser | Gly | Ile | Ser | Glu | Ile | Glu | Arg | Phe | Asp | Cys | Ser | Asn | Phe | |
| | 50 | | | | | 55 | | | | | 60 | | | | | |
| ccc | acg | aga | att | gca | gga | gag | ata | aaa | tcc | ttc | tct | act | gat | ggt | tgg | 240 |
| Pro | Thr | Arg | Ile | Ala | Gly | Glu | Ile | Lys | Ser | Phe | Ser | Thr | Asp | Gly | Trp | |
| 65 | | | | | 70 | | | | | 75 | | | | | 80 | |
| gtt | gca | cct | aaa | ctt | gca | aag | cgg | atg | gac | aag | ttt | atg | cta | tat | ctg | 288 |
| Val | Ala | Pro | Lys | Leu | Ala | Lys | Arg | Met | Asp | Lys | Phe | Met | Leu | Tyr | Leu | |
| | | | | 85 | | | | | 90 | | | | | 95 | | |
| ata | act | gct | gga | aag | aag | gca | tta | gaa | aat | ggt | gga | ctc | act | gaa | gaa | 336 |
| Ile | Thr | Ala | Gly | Lys | Lys | Ala | Leu | Glu | Asn | Gly | Gly | Leu | Thr | Glu | Glu | |
| | | | 100 | | | | | 105 | | | | | 110 | | | |
| cta | agg | aat | gag | ttg | gac | aaa | acc | agg | tgt | ggg | gtt | ctt | att | ggt | tct | 384 |
| Leu | Arg | Asn | Glu | Leu | Asp | Lys | Thr | Arg | Cys | Gly | Val | Leu | Ile | Gly | Ser | |
| | | 115 | | | | | 120 | | | | | 125 | | | | |
| gca | atg | ggt | ggc | atg | aag | gtt | ttt | aat | gat | gca | att | gaa | gca | ctg | agg | 432 |
| Ala | Met | Gly | Gly | Met | Lys | Val | Phe | Asn | Asp | Ala | Ile | Glu | Ala | Leu | Arg | |
| | 130 | | | | | 135 | | | | | 140 | | | | | |
| gtc | tct | tac | aag | aaa | atg | aac | cca | ttt | tgt | gtt | cct | ttt | gca | act | acg | 480 |
| Val | Ser | Tyr | Lys | Lys | Met | Asn | Pro | Phe | Cys | Val | Pro | Phe | Ala | Thr | Thr | |
| 145 | | | | | 150 | | | | | 155 | | | | | 160 | |
| aat | atg | ggc | tct | gcg | atc | ctt | gca | atg | gat | ctg | gga | tgg | atg | gga | cca | 528 |
| Asn | Met | Gly | Ser | Ala | Ile | Leu | Ala | Met | Asp | Leu | Gly | Trp | Met | Gly | Pro | |
| | | | 165 | | | | | 170 | | | | | 175 | | | |
| aac | tat | tct | att | tcc | aca | gct | tgt | gct | acc | agt | aac | ttc | tgt | atc | ctt | 576 |
| Asn | Tyr | Ser | Ile | Ser | Thr | Ala | Cys | Ala | Thr | Ser | Asn | Phe | Cys | Ile | Leu | |
| | | | 180 | | | | | 185 | | | | | 190 | | | |
| aat | gca | gca | aac | cac | atc | aga | aga | ggc | gaa | gct | gac | gtt | atg | ctc | tgc | 624 |
| Asn | Ala | Ala | Asn | His | Ile | Arg | Arg | Gly | Glu | Ala | Asp | Val | Met | Leu | Cys | |
| | | 195 | | | | | 200 | | | | | 205 | | | | |
| ggt | ggt | tct | gat | gca | cct | ctt | atc | cca | atc | gga | ttg | gga | ggt | ttt | gtg | 672 |
| Gly | Gly | Ser | Asp | Ala | Pro | Leu | Ile | Pro | Ile | Gly | Leu | Gly | Gly | Phe | Val | |
| | 210 | | | | | 215 | | | | | 220 | | | | | |
| gca | tgc | aga | gct | ctt | tca | cag | agg | aac | agt | gac | cca | aca | aaa | gct | tct | 720 |
| Ala | Cys | Arg | Ala | Leu | Ser | Gln | Arg | Asn | Ser | Asp | Pro | Thr | Lys | Ala | Ser | |
| 225 | | | | | 230 | | | | | 235 | | | | | 240 | |
| cgg | cct | tgg | gac | atg | gga | cgt | gat | ggt | ttt | gtt | atg | ggg | gaa | ggg | gct | 768 |
| Arg | Pro | Trp | Asp | Met | Gly | Arg | Asp | Gly | Phe | Val | Met | Gly | Glu | Gly | Ala | |
| | | | | 245 | | | | | 250 | | | | | 255 | | |
| ggt | gtc | ctc | gta | ttg | gaa | gaa | ctt | gag | cat | gcc | aag | gaa | aga | ggt | gca | 816 |
| Gly | Val | Leu | Val | Leu | Glu | Glu | Leu | Glu | His | Ala | Lys | Glu | Arg | Gly | Ala | |
| | | | 260 | | | | | 265 | | | | | 270 | | | |
| aca | ata | tat | gct | gaa | ttt | ctt | ggt | gga | agc | ttc | aca | tgt | gat | gct | tac | 864 |

```
Thr Ile Tyr Ala Glu Phe Leu Gly Gly Ser Phe Thr Cys Asp Ala Tyr
            275                 280                 285 cac atg act gag cca cat cct gaa gga aga ggg att gct ctc tgc atc      912
His Met Thr Glu Pro His Pro Glu Gly Arg Gly Ile Ala Leu Cys Ile
290                 295                 300 gaa aag gca cta gct gat gca ggg gta gca agg gaa gaa atc aac tac      960
Glu Lys Ala Leu Ala Asp Ala Gly Val Ala Arg Glu Glu Ile Asn Tyr
305                 310                 315                 320 gtg aat gcc cat gca aca tct aca caa gca ggt gac ttg aag gag tat     1008
Val Asn Ala His Ala Thr Ser Thr Gln Ala Gly Asp Leu Lys Glu Tyr
            325                 330                 335 gag gct atc gtg cgc tgt ttt cgc cag aac cct caa ctg agg gtg aac     1056
Glu Ala Ile Val Arg Cys Phe Arg Gln Asn Pro Gln Leu Arg Val Asn
            340                 345                 350 tcg acc aaa tca atg act ggg cat ctt ata gga gca gct ggt gga ata     1104
Ser Thr Lys Ser Met Thr Gly His Leu Ile Gly Ala Ala Gly Gly Ile
            355                 360                 365 gaa gca gtt gct tct ata caa gct ata aga act ggt tgg gtc cat cca     1152
Glu Ala Val Ala Ser Ile Gln Ala Ile Arg Thr Gly Trp Val His Pro
370                 375                 380 aat ttg aat tta gaa aat cca gag gac acc gtg gac gtg ggc gtc ttg     1200
Asn Leu Asn Leu Glu Asn Pro Glu Asp Thr Val Asp Val Gly Val Leu
385                 390                 395                 400 gta ggg tca cag aag gag aga tgt gaa gtg aag gtg gcg ttg tcc aac     1248
Val Gly Ser Gln Lys Glu Arg Cys Glu Val Lys Val Ala Leu Ser Asn
            405                 410                 415 tca ttc gga ttc ggt ggg cac aac tca tcg att ctc ttt gcc ccc ttt     1296
Ser Phe Gly Phe Gly Gly His Asn Ser Ser Ile Leu Phe Ala Pro Phe
            420                 425                 430 aag tga                                                              1302
Lys

<210> SEQ ID NO 9
<211> LENGTH: 433
<212> TYPE: PRT
<213> ORGANISM: Zea mays

<400> SEQUENCE: 9

Met Ala Val Ala Leu Gln Ala Glu Arg Ser Val Ile Glu Lys Lys Lys
1               5                   10                  15

Pro Asp Ile Lys Gln Arg Val Val Val Thr Gly Met Gly Val Val
            20                  25                  30

Thr Pro Leu Gly His Asp Pro Asp Val Phe Tyr Asn Asn Leu Leu Asp
        35                  40                  45

Gly Val Ser Gly Ile Ser Glu Ile Glu Arg Phe Asp Cys Ser Asn Phe
    50                  55                  60

Pro Thr Arg Ile Ala Gly Glu Ile Lys Ser Phe Ser Thr Asp Gly Trp
65                  70                  75                  80

Val Ala Pro Lys Leu Ala Lys Arg Met Asp Lys Phe Met Leu Tyr Leu
                85                  90                  95

Ile Thr Ala Gly Lys Lys Ala Leu Glu Asn Gly Leu Thr Glu Glu
            100                 105                 110

Leu Arg Asn Glu Leu Asp Lys Thr Arg Cys Gly Val Leu Ile Gly Ser
        115                 120                 125

Ala Met Gly Gly Met Lys Val Phe Asn Asp Ala Ile Glu Ala Leu Arg
    130                 135                 140

Val Ser Tyr Lys Lys Met Asn Pro Phe Cys Val Pro Phe Ala Thr Thr
145                 150                 155                 160
```

```
Asn Met Gly Ser Ala Ile Leu Ala Met Asp Leu Gly Trp Met Gly Pro
                165                 170                 175

Asn Tyr Ser Ile Ser Thr Ala Cys Ala Thr Ser Asn Phe Cys Ile Leu
            180                 185                 190

Asn Ala Ala Asn His Ile Arg Arg Gly Glu Ala Asp Val Met Leu Cys
        195                 200                 205

Gly Gly Ser Asp Ala Pro Leu Ile Pro Ile Gly Leu Gly Phe Val
    210                 215                 220

Ala Cys Arg Ala Leu Ser Gln Arg Asn Ser Asp Pro Thr Lys Ala Ser
225                 230                 235                 240

Arg Pro Trp Asp Met Gly Arg Asp Gly Phe Val Met Gly Glu Gly Ala
                245                 250                 255

Gly Val Leu Val Leu Glu Glu Leu Glu His Ala Lys Glu Arg Gly Ala
            260                 265                 270

Thr Ile Tyr Ala Glu Phe Leu Gly Gly Ser Phe Thr Cys Asp Ala Tyr
        275                 280                 285

His Met Thr Glu Pro His Pro Glu Gly Arg Gly Ile Ala Leu Cys Ile
    290                 295                 300

Glu Lys Ala Leu Ala Asp Ala Gly Val Ala Arg Glu Glu Ile Asn Tyr
305                 310                 315                 320

Val Asn Ala His Ala Thr Ser Thr Gln Ala Gly Asp Leu Lys Glu Tyr
                325                 330                 335

Glu Ala Ile Val Arg Cys Phe Arg Gln Asn Pro Gln Leu Arg Val Asn
            340                 345                 350

Ser Thr Lys Ser Met Thr Gly His Leu Ile Gly Ala Ala Gly Gly Ile
        355                 360                 365

Glu Ala Val Ala Ser Ile Gln Ala Ile Arg Thr Gly Trp Val His Pro
    370                 375                 380

Asn Leu Asn Leu Glu Asn Pro Glu Asp Thr Val Asp Val Gly Val Leu
385                 390                 395                 400

Val Gly Ser Gln Lys Glu Arg Cys Glu Val Lys Val Ala Leu Ser Asn
                405                 410                 415

Ser Phe Gly Phe Gly Gly His Asn Ser Ser Ile Leu Phe Ala Pro Phe
            420                 425                 430

Lys

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:5' primer
      with 128-fold degeneracy
<221> NAME/KEY: unsure
<222> LOCATION: (9)
<223> OTHER INFORMATION: a, t, g, or c
<221> NAME/KEY: unsure
<222> LOCATION: (18)
<223> OTHER INFORMATION: a, t, g, or c

<400> SEQUENCE: 10
atgaayccnt tytgygtncc                                                    20

<210> SEQ ID NO 11
<211> LENGTH: 22
<212> TYPE: DNA
<213> ORGANISM: Artificial Sequence
<220> FEATURE:
```

```
<223> OTHER INFORMATION: Description of Artificial Sequence:3' primer
      with 1024-fold degeneracy
<221> NAME/KEY: unsure
<222> LOCATION: (3)
<223> OTHER INFORMATION: a, t, g, or c
<221> NAME/KEY: unsure
<222> LOCATION: (12)
<223> OTHER INFORMATION: a, t, g, or c
<221> NAME/KEY: unsure
<222> LOCATION: (21)
<223> OTHER INFORMATION: a, t, g, or c

<400> SEQUENCE: 11
tcnggrttyt gnccraarca nc                                              22

<210> SEQ ID NO 12
<211> LENGTH: 596
<212> TYPE: DNA
<213> ORGANISM: Glycine max
<220> FEATURE:
<221> NAME/KEY: CDS
<222> LOCATION: (1)..(594)

<400> SEQUENCE: 12 atg aat cct ttt tgt gta cct ttt gca aca aca aat atg ggt tct gcc      48
Met Asn Pro Phe Cys Val Pro Phe Ala Thr Thr Asn Met Gly Ser Ala
 1               5                  10                  15 atg ctt gca atg gat ctg gga tgg atg ggc cct aat tat tct atc tct      96
Met Leu Ala Met Asp Leu Gly Trp Met Gly Pro Asn Tyr Ser Ile Ser
             20                  25                  30 aca gct tgt gct aca agt aac ttt tgt ata ttg aat gca gca aac cat     144
Thr Ala Cys Ala Thr Ser Asn Phe Cys Ile Leu Asn Ala Ala Asn His
         35                  40                  45 atc att aga ggt gaa gct gat gtg atg ctt tgt ggt ggc tca gat gct     192
Ile Ile Arg Gly Glu Ala Asp Val Met Leu Cys Gly Gly Ser Asp Ala
     50                  55                  60 gct att ata cca att ggt ttg gga ggc ttt gtg gca tgc agg gca ctc     240
Ala Ile Ile Pro Ile Gly Leu Gly Gly Phe Val Ala Cys Arg Ala Leu
 65                  70                  75                  80 tca caa agg aat act gat cct acc aaa gct tca cgc cct tgg gac att     288
Ser Gln Arg Asn Thr Asp Pro Thr Lys Ala Ser Arg Pro Trp Asp Ile
                 85                  90                  95 aac cgt gat gga ttt gtc atg gga gaa ggg gct gga gtt ttg ctt tta     336
Asn Arg Asp Gly Phe Val Met Gly Glu Gly Ala Gly Val Leu Leu Leu
            100                 105                 110 gaa gaa ctg gag cat gct aag aaa aga ggt gca acc ata tat gct gaa     384
Glu Glu Leu Glu His Ala Lys Lys Arg Gly Ala Thr Ile Tyr Ala Glu
        115                 120                 125 ttc ctt ggt gga agt ttc acc tgt gat gca tat cat gtg act gag ccg     432
Phe Leu Gly Gly Ser Phe Thr Cys Asp Ala Tyr His Val Thr Glu Pro
    130                 135                 140 cgt cct gat ggg gct ggt gtt att ctt tgc att gaa aag gca tta gct     480
Arg Pro Asp Gly Ala Gly Val Ile Leu Cys Ile Glu Lys Ala Leu Ala
145                 150                 155                 160 cag tct gga gta tca aaa gag gat gtg aat tac ata aat gca cat gcc     528
Gln Ser Gly Val Ser Lys Glu Asp Val Asn Tyr Ile Asn Ala His Ala
                165                 170                 175 aca tcc aca cca gct gga gat ctt aag gag tac caa gct cta atg cat     576
Thr Ser Thr Pro Ala Gly Asp Leu Lys Glu Tyr Gln Ala Leu Met His
            180                 185                 190 tgt ttt ggt caa aac ccc ga                                          596
Cys Phe Gly Gln Asn Pro
        195
```

```
<210> SEQ ID NO 13
<211> LENGTH: 198
<212> TYPE: PRT
<213> ORGANISM: Glycine max

<400> SEQUENCE: 13

Met Asn Pro Phe Cys Val Pro Phe Ala Thr Thr Asn Met Gly Ser Ala
  1               5                  10                  15

Met Leu Ala Met Asp Leu Gly Trp Met Gly Pro Asn Tyr Ser Ile Ser
             20                  25                  30

Thr Ala Cys Ala Thr Ser Asn Phe Cys Ile Leu Asn Ala Ala Asn His
         35                  40                  45

Ile Ile Arg Gly Glu Ala Asp Val Met Leu Cys Gly Gly Ser Asp Ala
     50                  55                  60

Ala Ile Ile Pro Ile Gly Leu Gly Gly Phe Val Ala Cys Arg Ala Leu
 65                  70                  75                  80

Ser Gln Arg Asn Thr Asp Pro Thr Lys Ala Ser Arg Pro Trp Asp Ile
                 85                  90                  95

Asn Arg Asp Gly Phe Val Met Gly Glu Gly Ala Gly Val Leu Leu Leu
            100                 105                 110

Glu Glu Leu Glu His Ala Lys Lys Arg Gly Ala Thr Ile Tyr Ala Glu
        115                 120                 125

Phe Leu Gly Gly Ser Phe Thr Cys Asp Ala Tyr His Val Thr Glu Pro
    130                 135                 140

Arg Pro Asp Gly Ala Gly Val Ile Leu Cys Ile Glu Lys Ala Leu Ala
145                 150                 155                 160

Gln Ser Gly Val Ser Lys Glu Asp Val Asn Tyr Ile Asn Ala His Ala
                165                 170                 175

Thr Ser Thr Pro Ala Gly Asp Leu Lys Glu Tyr Gln Ala Leu Met His
            180                 185                 190

Cys Phe Gly Gln Asn Pro
        195

<210> SEQ ID NO 14
<211> LENGTH: 2078
<212> TYPE: DNA
<213> ORGANISM: Glycine max
<220> FEATURE:
<221> NAME/KEY: CDS
<222> LOCATION: (179)..(1642)
<221> NAME/KEY: mat_peptide
<222> LOCATION: (347)..(1665)

<400> SEQUENCE: 14
agaataatcc ctttgttgaa accaaaacga cgacgcgtca cttcactttc atgtatctgc      60
gtgtctcgtc gtttctactt gctgttgctg ttgctgttgt tgattagcct cattcactca    120
ctcactcact cactcactcg ctcgcaacca caaccttgga tttcaatttt tttcattc      178 atg gct tcg acc acc acc tcc tcc ctc tgc acg tgg ctc gtc gct gct      226
Met Ala Ser Thr Thr Thr Ser Ser Leu Cys Thr Trp Leu Val Ala Ala
    -55                 -50                 -45 tgc atg tca gtc acg tgc gac gcc gac cgc acc aga acc cct cac gca      274
Cys Met Ser Val Thr Cys Asp Ala Asp Arg Thr Arg Thr Pro His Ala
-40                 -35                 -30                 -25 atc ttc cgc tcc tcc aaa aag tct cgc aag tct caa ttc aac gtc tct      322
Ile Phe Arg Ser Ser Lys Lys Ser Arg Lys Ser Gln Phe Asn Val Ser
                -20                 -15                 -10 cga tcc act cat tct ggt aaa aca atg gct gta gct ttg caa cct acc      370
```

```
                Arg Ser Thr His Ser Gly Lys Thr Met Ala Val Ala Leu Gln Pro Thr
                         -5              -1  1                  5 caa gag gtc aca aca ata aaa aaa cct cct aca aag caa agg cga gta            418
Gln Glu Val Thr Thr Ile Lys Lys Pro Pro Thr Lys Gln Arg Arg Val
     10              15                  20 gtt gtg aca gga ttg ggt gtg gtt aca cca ctt ggg cat gag cca gat            466
Val Val Thr Gly Leu Gly Val Val Thr Pro Leu Gly His Glu Pro Asp
 25              30                  35                  40 atc ttc tac aat aat ttg ctt gat ggt gtt agt ggc ata agt gag att            514
Ile Phe Tyr Asn Asn Leu Leu Asp Gly Val Ser Gly Ile Ser Glu Ile
                 45                  50                  55 gaa aca ttt gac tgt gca gaa tat cca aca agg att gct ggt gaa atc            562
Glu Thr Phe Asp Cys Ala Glu Tyr Pro Thr Arg Ile Ala Gly Glu Ile
                 60                  65                  70 aag tct ttc tca act gat ggc tgg gta gca cca aaa ctt tct aag aga            610
Lys Ser Phe Ser Thr Asp Gly Trp Val Ala Pro Lys Leu Ser Lys Arg
         75                  80                  85 atg gat aaa ttt atg ctc tat atg ctg aca gct ggc aaa aaa gcc ttg            658
Met Asp Lys Phe Met Leu Tyr Met Leu Thr Ala Gly Lys Lys Ala Leu
         90                  95                 100 gtt gat ggt gga att act gat gat gta atg gat gag tta aat aaa gat            706
Val Asp Gly Gly Ile Thr Asp Asp Val Met Asp Glu Leu Asn Lys Asp
105                 110                 115                 120 aag tgt gga gtt ctg att ggc tca gca atg ggt ggc atg aag gtt ttc            754
Lys Cys Gly Val Leu Ile Gly Ser Ala Met Gly Gly Met Lys Val Phe
                125                 130                 135 aat gat gcc att gaa gct tta cga atc tca tat aag aag atg aat cct            802
Asn Asp Ala Ile Glu Ala Leu Arg Ile Ser Tyr Lys Lys Met Asn Pro
                140                 145                 150 ttt tgt gta cct ttt gca aca aca aat atg ggt tct gcc atg ctt gca            850
Phe Cys Val Pro Phe Ala Thr Thr Asn Met Gly Ser Ala Met Leu Ala
        155                 160                 165 atg gat ctg gga tgg atg ggc cct aat tat tct atc tct aca gct tgt            898
Met Asp Leu Gly Trp Met Gly Pro Asn Tyr Ser Ile Ser Thr Ala Cys
        170                 175                 180 gct aca agt aac ttt tgt ata ttg aat gca gca aac cat atc att aga            946
Ala Thr Ser Asn Phe Cys Ile Leu Asn Ala Ala Asn His Ile Ile Arg
185                 190                 195                 200 ggt gaa gct gat gtg atg ctt tgt ggt ggc tca gat gct gct att ata            994
Gly Glu Ala Asp Val Met Leu Cys Gly Gly Ser Asp Ala Ala Ile Ile
                205                 210                 215 cca att ggt ttg gga ggc ttt gtg gca tgc agg gca ctc tca caa agg           1042
Pro Ile Gly Leu Gly Gly Phe Val Ala Cys Arg Ala Leu Ser Gln Arg
                220                 225                 230 aat act gat cct acc aaa gct tca cgc cct tgg gac att aac cgt gat           1090
Asn Thr Asp Pro Thr Lys Ala Ser Arg Pro Trp Asp Ile Asn Arg Asp
        235                 240                 245 gga ttt gtc atg gga gaa ggg gct gga gtt ttg ctt tta gaa gaa ctg           1138
Gly Phe Val Met Gly Glu Gly Ala Gly Val Leu Leu Leu Glu Glu Leu
        250                 255                 260 gag cat gct aag aaa aga ggt gca acc ata tat gct gaa ttc ctt ggt           1186
Glu His Ala Lys Lys Arg Gly Ala Thr Ile Tyr Ala Glu Phe Leu Gly
265                 270                 275                 280 gga agt ttc acc tgt gat gca tat cat gtg act gag ccg cgt cct gat           1234
Gly Ser Phe Thr Cys Asp Ala Tyr His Val Thr Glu Pro Arg Pro Asp
                285                 290                 295 ggg gct ggt gtt att ctt tgc att gaa aag gca tta gct cag tct gga           1282
Gly Ala Gly Val Ile Leu Cys Ile Glu Lys Ala Leu Ala Gln Ser Gly
                300                 305                 310
```

-continued

```
gta tca aaa gag gat gtg aat tac ata aat gca cat gcc aca tcc aca      1330
Val Ser Lys Glu Asp Val Asn Tyr Ile Asn Ala His Ala Thr Ser Thr
        315                 320                 325 cca gct gga gat ctt aag gag tac caa gct cta atg cat tgt ttt ggt      1378
Pro Ala Gly Asp Leu Lys Glu Tyr Gln Ala Leu Met His Cys Phe Gly
    330                 335                 340 caa aac ccc aag tta cga gtg aat tct aca aaa tct atg att ggt cat      1426
Gln Asn Pro Lys Leu Arg Val Asn Ser Thr Lys Ser Met Ile Gly His
345                 350                 355                 360 cta cta ggg gca gct ggc gct gtg gaa gct gtg gcc aca ata cag gca      1474
Leu Leu Gly Ala Ala Gly Ala Val Glu Ala Val Ala Thr Ile Gln Ala
                365                 370                 375 att agg aca ggg tgg gtt cat ccc aat atc aac cta gaa aag cca gat      1522
Ile Arg Thr Gly Trp Val His Pro Asn Ile Asn Leu Glu Lys Pro Asp
        380                 385                 390 aat gga gtg gat gct aaa gtg ctt gtt ggc tca aag aaa gag aga ctg      1570
Asn Gly Val Asp Ala Lys Val Leu Val Gly Ser Lys Lys Glu Arg Leu
    395                 400                 405 gat gtc aag gca gcc ttg tcg aat tca ttt ggt ttt ggg ggt cac aat      1618
Asp Val Lys Ala Ala Leu Ser Asn Ser Phe Gly Phe Gly Gly His Asn
410                 415                 420 tct tca atc ata ttt gca cct tac aagtgaaaca gatttcagag cactactttc    1672
Ser Ser Ile Ile Phe Ala Pro Tyr
425                 430 ttattattat aaggtactga gtacccagac aatgttattg catactaact ccagtgtttt   1732
tggttgggtg agaatatatg cggtgtggat tagttggttg gatcagtatc tgttgagaaa   1792
cattgttttt tgggatgggg ttacagaatc agaatgttga tagattatct ggtgctcctg   1852
gtgagagaga gtgagtgagt ctctatctat ccactgctat aaaatcctat ctttaccatg   1912
aatatgaatg gctagagtag gagttgaccc acttttgatg taaccgttta acaaccattt   1972
tgatgggatg gatacagtct tgttttattc ccatgtacaa atagaccctc atggctctgg   2032
gcattgggca ataaccagtt taagtgatta aaaaaaaaaa aaaaaa                  2078
```

<210> SEQ ID NO 15
<211> LENGTH: 488
<212> TYPE: PRT
<213> ORGANISM: Glycine max

<400> SEQUENCE: 15

```
Met Ala Ser Thr Thr Ser Ser Leu Cys Thr Trp Leu Val Ala Ala
        -55                 -50                 -45

Cys Met Ser Val Thr Cys Asp Ala Asp Arg Thr Arg Thr Pro His Ala
-40                 -35                 -30                 -25

Ile Phe Arg Ser Ser Lys Lys Ser Arg Lys Ser Gln Phe Asn Val Ser
                -20                 -15                 -10

Arg Ser Thr His Ser Gly Lys Thr Met Ala Val Ala Leu Gln Pro Thr
            -5                  -1   1                   5

Gln Glu Val Thr Thr Ile Lys Lys Pro Pro Thr Lys Gln Arg Arg Val
    10                  15                  20

Val Val Thr Gly Leu Gly Val Thr Pro Leu Gly His Glu Pro Asp
25                  30                  35                  40

Ile Phe Tyr Asn Asn Leu Leu Asp Gly Val Ser Gly Ile Ser Glu Ile
                45                  50                  55

Glu Thr Phe Asp Cys Ala Glu Tyr Pro Thr Arg Ile Ala Gly Glu Ile
            60                  65                  70

Lys Ser Phe Ser Thr Asp Gly Trp Val Ala Pro Lys Leu Ser Lys Arg
```

```
                    75                  80                  85
Met Asp Lys Phe Met Leu Tyr Met Leu Thr Ala Gly Lys Lys Ala Leu
     90                  95                 100

Val Asp Gly Gly Ile Thr Asp Val Met Asp Glu Leu Asn Lys Asp
105                 110                 115                 120

Lys Cys Gly Val Leu Ile Gly Ser Ala Met Gly Met Lys Val Phe
                125                 130                 135

Asn Asp Ala Ile Glu Ala Leu Arg Ile Ser Tyr Lys Lys Met Asn Pro
                140                 145                 150

Phe Cys Val Pro Phe Ala Thr Thr Asn Met Gly Ser Ala Met Leu Ala
            155                 160                 165

Met Asp Leu Gly Trp Met Gly Pro Asn Tyr Ser Ile Ser Thr Ala Cys
        170                 175                 180

Ala Thr Ser Asn Phe Cys Ile Leu Asn Ala Ala Asn His Ile Ile Arg
185                 190                 195                 200

Gly Glu Ala Asp Val Met Leu Cys Gly Gly Ser Asp Ala Ala Ile Ile
                205                 210                 215

Pro Ile Gly Leu Gly Gly Phe Val Ala Cys Arg Ala Leu Ser Gln Arg
                220                 225                 230

Asn Thr Asp Pro Thr Lys Ala Ser Arg Pro Trp Asp Ile Asn Arg Asp
                235                 240                 245

Gly Phe Val Met Gly Glu Gly Ala Gly Val Leu Leu Leu Glu Glu Leu
            250                 255                 260

Glu His Ala Lys Lys Arg Gly Ala Thr Ile Tyr Ala Glu Phe Leu Gly
265                 270                 275                 280

Gly Ser Phe Thr Cys Asp Ala Tyr His Val Thr Glu Pro Arg Pro Asp
                285                 290                 295

Gly Ala Gly Val Ile Leu Cys Ile Glu Lys Ala Leu Ala Gln Ser Gly
            300                 305                 310

Val Ser Lys Glu Asp Val Asn Tyr Ile Asn Ala His Ala Thr Ser Thr
            315                 320                 325

Pro Ala Gly Asp Leu Lys Glu Tyr Gln Ala Leu Met His Cys Phe Gly
        330                 335                 340

Gln Asn Pro Lys Leu Arg Val Asn Ser Thr Lys Ser Met Ile Gly His
345                 350                 355                 360

Leu Leu Gly Ala Ala Gly Ala Val Glu Ala Val Ala Thr Ile Gln Ala
                365                 370                 375

Ile Arg Thr Gly Trp Val His Pro Asn Ile Asn Leu Glu Lys Pro Asp
            380                 385                 390

Asn Gly Val Asp Ala Lys Val Leu Val Gly Ser Lys Lys Glu Arg Leu
            395                 400                 405

Asp Val Lys Ala Ala Leu Ser Asn Ser Phe Gly Phe Gly Gly His Asn
        410                 415                 420

Ser Ser Ile Ile Phe Ala Pro Tyr
425                 430

<210> SEQ ID NO 16
<211> LENGTH: 1470
<212> TYPE: DNA
<213> ORGANISM: Glycine max
<220> FEATURE:
<221> NAME/KEY: CDS
<222> LOCATION: (1)..(1467)
<221> NAME/KEY: mat_peptide
<222> LOCATION: (169)..(1467)
```

<400> SEQUENCE: 16

```
atg gct tcg acc acc acc tcc tcc ctc tgc acg tgg ctc gtc gct gct        48
Met Ala Ser Thr Thr Thr Ser Ser Leu Cys Thr Trp Leu Val Ala Ala
    -55                 -50                 -45 tgc atg tca gtc acg tgc gac gcc gac cgc acc aga acc cct cac gca        96
Cys Met Ser Val Thr Cys Asp Ala Asp Arg Thr Arg Thr Pro His Ala
-40                 -35                 -30                 -25 atc ttc cgc tcc tcc aaa aag tct cgc aag tct caa ttc aac gtc tct       144
Ile Phe Arg Ser Ser Lys Lys Ser Arg Lys Ser Gln Phe Asn Val Ser
                -20                 -15                 -10 cga tcc act cat tct ggt aaa aca atg gct gta gct ttg caa cct acc       192
Arg Ser Thr His Ser Gly Lys Thr Met Ala Val Ala Leu Gln Pro Thr
            -5                  -1  1                   5 caa gag gtc aca aca ata aaa aaa cct cct aca aag caa agg cga gta       240
Gln Glu Val Thr Thr Ile Lys Lys Pro Pro Thr Lys Gln Arg Arg Val
        10                  15                  20 gtt gtg aca gga ttg ggt gtg gtt aca cca ctt ggg cat gag cca gat       288
Val Val Thr Gly Leu Gly Val Val Thr Pro Leu Gly His Glu Pro Asp
25                  30                  35                  40 atc ttc tac aat aat ttg ctt gat ggt gtt agt ggc ata agt gag att       336
Ile Phe Tyr Asn Asn Leu Leu Asp Gly Val Ser Gly Ile Ser Glu Ile
                45                  50                  55 gaa aca ttt gac tgt gca gaa tat cca aca agg att gct ggt gaa atc       384
Glu Thr Phe Asp Cys Ala Glu Tyr Pro Thr Arg Ile Ala Gly Glu Ile
            60                  65                  70 aag tct ttc tca act gat ggc tgg gta gca cca aaa ctt tct aag aga       432
Lys Ser Phe Ser Thr Asp Gly Trp Val Ala Pro Lys Leu Ser Lys Arg
        75                  80                  85 atg gat aaa ttt atg ctc tat atg ctg aca gct ggc aaa aaa gcc ttg       480
Met Asp Lys Phe Met Leu Tyr Met Leu Thr Ala Gly Lys Lys Ala Leu
    90                  95                  100 gtt gat ggt gga att act gat gat gta atg gat gag tta aat aaa gat       528
Val Asp Gly Gly Ile Thr Asp Asp Val Met Asp Glu Leu Asn Lys Asp
105                 110                 115                 120 aag tgt gga gtt ctg att ggc tca gca atg ggt ggc atg aag gtt ttc       576
Lys Cys Gly Val Leu Ile Gly Ser Ala Met Gly Gly Met Lys Val Phe
                125                 130                 135 aat gat gcc att gaa gct tta cga atc tca tat aag aag atg aat cct       624
Asn Asp Ala Ile Glu Ala Leu Arg Ile Ser Tyr Lys Lys Met Asn Pro
            140                 145                 150 ttt tgt gta cct ttt gca aca aca aat atg ggt tct gcc atg ctt gca       672
Phe Cys Val Pro Phe Ala Thr Thr Asn Met Gly Ser Ala Met Leu Ala
        155                 160                 165 atg gat ctg gga tgg atg ggc cct aat tat tct atc tct aca gct tgt       720
Met Asp Leu Gly Trp Met Gly Pro Asn Tyr Ser Ile Ser Thr Ala Cys
    170                 175                 180 gct aca agt aac ttt tgt ata ttg aat gca gca aac cat atc att aga       768
Ala Thr Ser Asn Phe Cys Ile Leu Asn Ala Ala Asn His Ile Ile Arg
185                 190                 195                 200 ggt gaa gct gat gtg atg ctt tgt ggt ggc tca gat gct gct att ata       816
Gly Glu Ala Asp Val Met Leu Cys Gly Gly Ser Asp Ala Ala Ile Ile
                205                 210                 215 cca att ggt ttg gga ggc ttt gtg gca tgc agg gca ctc tca caa agg       864
Pro Ile Gly Leu Gly Gly Phe Val Ala Cys Arg Ala Leu Ser Gln Arg
            220                 225                 230 aat act gat cct acc aaa gct tca cgc cct tgg gac att aac cgt gat       912
Asn Thr Asp Pro Thr Lys Ala Ser Arg Pro Trp Asp Ile Asn Arg Asp
        235                 240                 245 gga ttt gtc atg gga gaa ggg gct gga gtt ttg ctt tta gaa gaa ctg       960
Gly Phe Val Met Gly Glu Gly Ala Gly Val Leu Leu Leu Glu Glu Leu
```

-continued

```
                Gly Phe Val Met Gly Glu Gly Ala Gly Val Leu Leu Glu Glu Leu
                        250                 255                 260 gag cat gct aag aaa aga ggt gca acc ata tat gct gaa ttc ctt ggt        1008
Glu His Ala Lys Lys Arg Gly Ala Thr Ile Tyr Ala Glu Phe Leu Gly
265                 270                 275                 280 gga agt ttc acc tgt gat gca tat cat gtg act gag ccg cgt cct gat        1056
Gly Ser Phe Thr Cys Asp Ala Tyr His Val Thr Glu Pro Arg Pro Asp
                285                 290                 295 ggg gct ggt gtt att ctt tgc att gaa aag gca tta gct cag tct gga        1104
Gly Ala Gly Val Ile Leu Cys Ile Glu Lys Ala Leu Ala Gln Ser Gly
            300                 305                 310 gta tca aaa gag gat gtg aat tac ata aat gca cat gcc aca tcc aca        1152
Val Ser Lys Glu Asp Val Asn Tyr Ile Asn Ala His Ala Thr Ser Thr
        315                 320                 325 cca gct gga gat ctt aag gag tac caa gct cta atg cat tgt ttt ggt        1200
Pro Ala Gly Asp Leu Lys Glu Tyr Gln Ala Leu Met His Cys Phe Gly
    330                 335                 340 caa aac ccc aag tta cga gtg aat tct aca aaa tct atg att ggt cat        1248
Gln Asn Pro Lys Leu Arg Val Asn Ser Thr Lys Ser Met Ile Gly His
345                 350                 355                 360 cta cta ggg gca gct ggc gct gtg gaa gct gtg gcc aca ata cag gca        1296
Leu Leu Gly Ala Ala Gly Ala Val Glu Ala Val Ala Thr Ile Gln Ala
                365                 370                 375 att agg aca ggg tgg gtt cat ccc aat atc aac cta gaa aag cca gat        1344
Ile Arg Thr Gly Trp Val His Pro Asn Ile Asn Leu Glu Lys Pro Asp
                380                 385                 390 aat gga gtg gat gct aaa gtg ctt gtt ggc tca aag aaa gag aga ctg        1392
Asn Gly Val Asp Ala Lys Val Leu Val Gly Ser Lys Lys Glu Arg Leu
            395                 400                 405 gat gtc aag gca gcc ttg tcg aat tca ttt ggt ttt ggg ggt cac aat        1440
Asp Val Lys Ala Ala Leu Ser Asn Ser Phe Gly Phe Gly Gly His Asn
        410                 415                 420 tct tca atc ata ttt gca cct tac aag tga                                 1470
Ser Ser Ile Ile Phe Ala Pro Tyr Lys
425                 430

<210> SEQ ID NO 17
<211> LENGTH: 1302
<212> TYPE: DNA
<213> ORGANISM: Glycine max
<220> FEATURE:
<221> NAME/KEY: CDS
<222> LOCATION: (1)..(1299)

<400> SEQUENCE: 17 atg gct gta gct ttg caa cct acc caa gag gtc aca aca ata aaa aaa          48
Met Ala Val Ala Leu Gln Pro Thr Gln Glu Val Thr Thr Ile Lys Lys
1               5                   10                  15 cct cct aca aag caa agg cga gta gtt gtg aca gga ttg ggt gtg gtt          96
Pro Pro Thr Lys Gln Arg Arg Val Val Val Thr Gly Leu Gly Val Val
            20                  25                  30 aca cca ctt ggg cat gag cca gat atc ttc tac aat aat ttg ctt gat         144
Thr Pro Leu Gly His Glu Pro Asp Ile Phe Tyr Asn Asn Leu Leu Asp
        35                  40                  45 ggt gtt agt ggc ata agt gag att gaa aca ttt gac tgt gca gaa tat         192
Gly Val Ser Gly Ile Ser Glu Ile Glu Thr Phe Asp Cys Ala Glu Tyr
    50                  55                  60 cca aca agg att gct ggt gaa atc aag tct ttc tca act gat ggc tgg         240
Pro Thr Arg Ile Ala Gly Glu Ile Lys Ser Phe Ser Thr Asp Gly Trp
65                  70                  75                  80 gta gca cca aaa ctt tct aag aga atg gat aaa ttt atg ctc tat atg         288
```

-continued

```
                Val Ala Pro Lys Leu Ser Lys Arg Met Asp Lys Phe Met Leu Tyr Met
                            85                  90                  95 ctg aca gct ggc aaa aaa gcc ttg gtt gat ggt gga att act gat gat      336
Leu Thr Ala Gly Lys Lys Ala Leu Val Asp Gly Gly Ile Thr Asp Asp
            100                 105                 110 gta atg gat gag tta aat aaa gat aag tgt gga gtt ctg att ggc tca      384
Val Met Asp Glu Leu Asn Lys Asp Lys Cys Gly Val Leu Ile Gly Ser
        115                 120                 125 gca atg ggt ggc atg aag gtt ttc aat gat gcc att gaa gct tta cga      432
Ala Met Gly Gly Met Lys Val Phe Asn Asp Ala Ile Glu Ala Leu Arg
    130                 135                 140 atc tca tat aag aag atg aat cct ttt tgt gta cct ttt gca aca aca      480
Ile Ser Tyr Lys Lys Met Asn Pro Phe Cys Val Pro Phe Ala Thr Thr
145                 150                 155                 160 aat atg ggt tct gcc atg ctt gca atg gat ctg gga tgg atg ggc cct      528
Asn Met Gly Ser Ala Met Leu Ala Met Asp Leu Gly Trp Met Gly Pro
                165                 170                 175 aat tat tct atc tct aca gct tgt gct aca agt aac ttt tgt ata ttg      576
Asn Tyr Ser Ile Ser Thr Ala Cys Ala Thr Ser Asn Phe Cys Ile Leu
            180                 185                 190 aat gca gca aac cat atc att aga ggt gaa gct gat gtg atg ctt tgt      624
Asn Ala Ala Asn His Ile Ile Arg Gly Glu Ala Asp Val Met Leu Cys
        195                 200                 205 ggt ggc tca gat gct gct att ata cca att ggt ttg gga ggc ttt gtg      672
Gly Gly Ser Asp Ala Ala Ile Ile Pro Ile Gly Leu Gly Gly Phe Val
    210                 215                 220 gca tgc agg gca ctc tca caa agg aat act gat cct acc aaa gct tca      720
Ala Cys Arg Ala Leu Ser Gln Arg Asn Thr Asp Pro Thr Lys Ala Ser
225                 230                 235                 240 cgc cct tgg gac att aac cgt gat gga ttt gtc atg gga gaa ggg gct      768
Arg Pro Trp Asp Ile Asn Arg Asp Gly Phe Val Met Gly Glu Gly Ala
                245                 250                 255 gga gtt ttg ctt tta gaa gaa ctg gag cat gct aag aaa aga ggt gca      816
Gly Val Leu Leu Leu Glu Glu Leu Glu His Ala Lys Lys Arg Gly Ala
            260                 265                 270 acc ata tat gct gaa ttc ctt ggt gga agt ttc acc tgt gat gca tat      864
Thr Ile Tyr Ala Glu Phe Leu Gly Gly Ser Phe Thr Cys Asp Ala Tyr
        275                 280                 285 cat gtg act gag ccg cgt cct gat ggg gct ggt gtt att ctt tgc att      912
His Val Thr Glu Pro Arg Pro Asp Gly Ala Gly Val Ile Leu Cys Ile
    290                 295                 300 gaa aag gca tta gct cag tct gga gta tca aaa gag gat gtg aat tac      960
Glu Lys Ala Leu Ala Gln Ser Gly Val Ser Lys Glu Asp Val Asn Tyr
305                 310                 315                 320 ata aat gca cat gcc aca tcc aca cca gct gga gat ctt aag gag tac     1008
Ile Asn Ala His Ala Thr Ser Thr Pro Ala Gly Asp Leu Lys Glu Tyr
                325                 330                 335 caa gct cta atg cat tgt ttt ggt caa aac ccc aag tta cga gtg aat     1056
Gln Ala Leu Met His Cys Phe Gly Gln Asn Pro Lys Leu Arg Val Asn
            340                 345                 350 tct aca aaa tct atg att ggt cat cta cta ggg gca gct ggc gct gtg     1104
Ser Thr Lys Ser Met Ile Gly His Leu Leu Gly Ala Ala Gly Ala Val
        355                 360                 365 gaa gct gtg gcc aca ata cag gca att agg aca ggg tgg gtt cat ccc     1152
Glu Ala Val Ala Thr Ile Gln Ala Ile Arg Thr Gly Trp Val His Pro
    370                 375                 380 aat atc aac cta gaa aag cca gat aat gga gtg gat gct aaa gtg ctt     1200
Asn Ile Asn Leu Glu Lys Pro Asp Asn Gly Val Asp Ala Lys Val Leu
385                 390                 395                 400
```

| | | |
|---|---|---|
| gtt ggc tca aag aaa gag aga ctg gat gtc aag gca gcc ttg tcg aat<br>Val Gly Ser Lys Lys Glu Arg Leu Asp Val Lys Ala Ala Leu Ser Asn<br>                 405                     410                   415 | | 1248 |
| tca ttt ggt ttt ggg ggt cac aat tct tca atc ata ttt gca cct tac<br>Ser Phe Gly Phe Gly Gly His Asn Ser Ser Ile Ile Phe Ala Pro Tyr<br>                 420                     425                   430 | | 1296 |
| aag tga<br>Lys | | 1302 |

<210> SEQ ID NO 18
<211> LENGTH: 433
<212> TYPE: PRT
<213> ORGANISM: Glycine max

<400> SEQUENCE: 18

Met Ala Val Ala Leu Gln Pro Thr Gln Glu Val Thr Thr Ile Lys Lys
 1               5                  10                  15

Pro Pro Thr Lys Gln Arg Arg Val Val Thr Gly Leu Gly Val Val
             20                  25                  30

Thr Pro Leu Gly His Glu Pro Asp Ile Phe Tyr Asn Asn Leu Leu Asp
         35                  40                  45

Gly Val Ser Gly Ile Ser Glu Ile Glu Thr Phe Asp Cys Ala Glu Tyr
     50                  55                  60

Pro Thr Arg Ile Ala Gly Glu Ile Lys Ser Phe Ser Thr Asp Gly Trp
 65                  70                  75                  80

Val Ala Pro Lys Leu Ser Lys Arg Met Asp Lys Phe Met Leu Tyr Met
                 85                  90                  95

Leu Thr Ala Gly Lys Lys Ala Leu Val Asp Gly Gly Ile Thr Asp Asp
            100                 105                 110

Val Met Asp Glu Leu Asn Lys Asp Lys Cys Gly Val Leu Ile Gly Ser
        115                 120                 125

Ala Met Gly Gly Met Lys Val Phe Asn Asp Ala Ile Glu Ala Leu Arg
    130                 135                 140

Ile Ser Tyr Lys Lys Met Asn Pro Phe Cys Val Pro Phe Ala Thr Thr
145                 150                 155                 160

Asn Met Gly Ser Ala Met Leu Ala Met Asp Leu Gly Trp Met Gly Pro
                165                 170                 175

Asn Tyr Ser Ile Ser Thr Ala Cys Ala Thr Ser Asn Phe Cys Ile Leu
            180                 185                 190

Asn Ala Ala Asn His Ile Ile Arg Gly Glu Ala Asp Val Met Leu Cys
        195                 200                 205

Gly Gly Ser Asp Ala Ala Ile Ile Pro Ile Gly Leu Gly Gly Phe Val
    210                 215                 220

Ala Cys Arg Ala Leu Ser Gln Arg Asn Thr Asp Pro Thr Lys Ala Ser
225                 230                 235                 240

Arg Pro Trp Asp Ile Asn Arg Asp Gly Phe Val Met Gly Glu Gly Ala
                245                 250                 255

Gly Val Leu Leu Leu Glu Glu Leu Glu His Ala Lys Lys Arg Gly Ala
            260                 265                 270

Thr Ile Tyr Ala Glu Phe Leu Gly Gly Ser Phe Thr Cys Asp Ala Tyr
        275                 280                 285

His Val Thr Glu Pro Arg Pro Asp Gly Ala Gly Val Ile Leu Cys Ile
    290                 295                 300

Glu Lys Ala Leu Ala Gln Ser Gly Val Ser Lys Glu Asp Val Asn Tyr
305                 310                 315                 320

-continued

```
Ile Asn Ala His Ala Thr Ser Thr Pro Ala Gly Asp Leu Lys Glu Tyr
            325                 330                 335
Gln Ala Leu Met His Cys Phe Gly Gln Asn Pro Lys Leu Arg Val Asn
            340                 345                 350
Ser Thr Lys Ser Met Ile Gly His Leu Leu Gly Ala Ala Gly Ala Val
            355                 360                 365
Glu Ala Val Ala Thr Ile Gln Ala Ile Arg Thr Gly Trp Val His Pro
    370                 375                 380
Asn Ile Asn Leu Glu Lys Pro Asp Asn Gly Val Asp Ala Lys Val Leu
385                 390                 395                 400
Val Gly Ser Lys Lys Glu Arg Leu Asp Val Lys Ala Ala Leu Ser Asn
            405                 410                 415
Ser Phe Gly Phe Gly Gly His Asn Ser Ser Ile Ile Phe Ala Pro Tyr
            420                 425                 430
Lys
```

<210> SEQ ID NO 19
<211> LENGTH: 2232
<212> TYPE: DNA
<213> ORGANISM: Glycine max
<220> FEATURE:
<221> NAME/KEY: CDS
<222> LOCATION: (213)..(1676)
<221> NAME/KEY: mat_peptide
<222> LOCATION: (381)..(1676)

<400> SEQUENCE: 19

```
agcagaaacg cagcagcatc gtgttggaga gtgagacgga atgcattagt gaagaccgag      60
gtttctcaga atctcaataa cccccttcgt tgaaaccaaa acgacgacgc gtcacttcac     120
tttgatgtgt ctcgtcgttt ctactttctg ttgattagcc tcattcactc tctcgctcgc     180
ttgcaaccac acccttggat ttaatttcat tc atg gct tcg acc acc acc tcc      233
                                    Met Ala Ser Thr Thr Thr Ser
                                        -55                 -50 tcc ctc tgc acg tgg ctc gtt gct gct tgc atg tca gtc acg tgc cac      281
Ser Leu Cys Thr Trp Leu Val Ala Ala Cys Met Ser Val Thr Cys His
        -45                 -40                 -35 gcc gac cgc acc aaa acc cct cac gca atg ttc cgc tcc tcc aaa aag      329
Ala Asp Arg Thr Lys Thr Pro His Ala Met Phe Arg Ser Ser Lys Lys
    -30                 -25                 -20 tct cgc tac tct caa ttc aac gtt tgt cga tcc act cat tct ggt aaa      377
Ser Arg Tyr Ser Gln Phe Asn Val Cys Arg Ser Thr His Ser Gly Lys
        -15                 -10                  -5 aca atg gct gta gct ttg caa cct acc caa gag atc acg aca ata aaa      425
Thr Met Ala Val Ala Leu Gln Pro Thr Gln Glu Ile Thr Thr Ile Lys
 -1   1                  5                  10                 15 aaa cct ccc acg aag caa agg cga gtg gtt gtg aca gga ttg ggt gtg      473
Lys Pro Pro Thr Lys Gln Arg Arg Val Val Val Thr Gly Leu Gly Val
                20                  25                  30 gtt aca cca ctt ggg cat gag cca gat atc ttc tac aat aat ttg ctt      521
Val Thr Pro Leu Gly His Glu Pro Asp Ile Phe Tyr Asn Asn Leu Leu
            35                  40                  45 gat ggt gct agt ggc ata agc gag att gaa aca ttt gat tgt gca gaa      569
Asp Gly Ala Ser Gly Ile Ser Glu Ile Glu Thr Phe Asp Cys Ala Glu
        50                  55                  60 tat cca aca agg att gct ggt gaa atc aag tct ttc tca act gat ggc      617
Tyr Pro Thr Arg Ile Ala Gly Glu Ile Lys Ser Phe Ser Thr Asp Gly
    65                  70                  75 tgg gta gca cca aaa ctt tct aag aga atg gat aaa ttt atg ctc tat      665
```

```
                Trp Val Ala Pro Lys Leu Ser Lys Arg Met Asp Lys Phe Met Leu Tyr
                 80                  85                  90                  95 atg ctg aca gct ggc aaa aaa gcc ttg gtt gat ggt gga att act gat             713
Met Leu Thr Ala Gly Lys Lys Ala Leu Val Asp Gly Gly Ile Thr Asp
                100                 105                 110 gat gta atg gat gag tta aat aaa gaa aag tgt gga gtt ctg att ggg             761
Asp Val Met Asp Glu Leu Asn Lys Glu Lys Cys Gly Val Leu Ile Gly
            115                 120                 125 tca gca atg ggt ggc atg aag gtt ttc aat gat gcc atc gaa gct tta             809
Ser Ala Met Gly Gly Met Lys Val Phe Asn Asp Ala Ile Glu Ala Leu
        130                 135                 140 cga atc tca tat aag aag atg aag cct ttt tgt gta cct ttt gca aca             857
Arg Ile Ser Tyr Lys Lys Met Lys Pro Phe Cys Val Pro Phe Ala Thr
    145                 150                 155 aca aat atg ggt tct gcc atg ctt gca atg gat ctg gga tgg atg ggc             905
Thr Asn Met Gly Ser Ala Met Leu Ala Met Asp Leu Gly Trp Met Gly
160                 165                 170                 175 cct aat tat tct atc tct aca gct tgt gct aca agt aac ttt tgt ata             953
Pro Asn Tyr Ser Ile Ser Thr Ala Cys Ala Thr Ser Asn Phe Cys Ile
                180                 185                 190 ttg aat gca gca aac cat atc att aga ggt gaa gct gat gtg atg ctt            1001
Leu Asn Ala Ala Asn His Ile Ile Arg Gly Glu Ala Asp Val Met Leu
            195                 200                 205 tgt gga ggc tca gat gct gct att ata cca att ggt ttg gga ggc ttt            1049
Cys Gly Gly Ser Asp Ala Ala Ile Ile Pro Ile Gly Leu Gly Gly Phe
        210                 215                 220 gtg gca tgc agg gca ctc tca caa agg aat act gat cct acc aaa gct            1097
Val Ala Cys Arg Ala Leu Ser Gln Arg Asn Thr Asp Pro Thr Lys Ala
    225                 230                 235 tca cgc cct tgg gac att aac cgt gat gga ttt gtc atg ggt gaa ggg            1145
Ser Arg Pro Trp Asp Ile Asn Arg Asp Gly Phe Val Met Gly Glu Gly
240                 245                 250                 255 gct gga gtt ttg ctt tta gag gaa ctg gag cat gct aag gaa aga ggt            1193
Ala Gly Val Leu Leu Leu Glu Glu Leu Glu His Ala Lys Glu Arg Gly
                260                 265                 270 gca acc ata tat gct gaa ttc ctt ggt gga agt ttc acc tgt gat gca            1241
Ala Thr Ile Tyr Ala Glu Phe Leu Gly Gly Ser Phe Thr Cys Asp Ala
            275                 280                 285 tat cat gtg act gag ccg cgt cct gat ggg gct ggt gtt ata ctg tgc            1289
Tyr His Val Thr Glu Pro Arg Pro Asp Gly Ala Gly Val Ile Leu Cys
        290                 295                 300 att gaa aag gca tta gct cag tct gga gta tca aaa gag gat gtg aat            1337
Ile Glu Lys Ala Leu Ala Gln Ser Gly Val Ser Lys Glu Asp Val Asn
    305                 310                 315 tac ata aat gca cat gcc aca tcc aca cca gct gga gat ctt aag gag            1385
Tyr Ile Asn Ala His Ala Thr Ser Thr Pro Ala Gly Asp Leu Lys Glu
320                 325                 330                 335 tac caa gct cta atg cat tgt ttt ggt caa aac ccc gag tta aga gtg            1433
Tyr Gln Ala Leu Met His Cys Phe Gly Gln Asn Pro Glu Leu Arg Val
                340                 345                 350 aat tct aca aaa tct atg att ggt cat cta cta ggg gca gct ggc ggt            1481
Asn Ser Thr Lys Ser Met Ile Gly His Leu Leu Gly Ala Ala Gly Gly
            355                 360                 365 gtg gca gct gtg gcc aca ata cag gca att agg aca ggg tgg gtt cat            1529
Val Ala Ala Val Ala Thr Ile Gln Ala Ile Arg Thr Gly Trp Val His
        370                 375                 380 ccc aat atc aac cta gaa aac cca gat aac gga gtg gat gct aaa gtg            1577
Pro Asn Ile Asn Leu Glu Asn Pro Asp Asn Gly Val Asp Ala Lys Val
    385                 390                 395
```

-continued

| | | |
|---|---|---|
| ctt gtt ggc tca aag aaa gag aga ctg gat gtc aag gca gcc ttg tcg<br>Leu Val Gly Ser Lys Lys Glu Arg Leu Asp Val Lys Ala Ala Leu Ser<br>400                         405                   410                              415 | 1625 |
| aat tca ttt ggt ttt ggg ggt cac aat tct tca atc ata ttt gca cca<br>Asn Ser Phe Gly Phe Gly Gly His Asn Ser Ser Ile Ile Phe Ala Pro<br>                    420                         425                         430 | 1673 |
| tac tagtgaaaca gatttcagag cagtactttc ttattattat aagttactga<br>Tyr | 1726 |
| gtacccagac aatgtttatt gcatactaac tccagtgttt tggttggttg agaatatatg | 1786 |
| cggtgtggat tagttggttg gatcagtaac tgttgagaaa cattgttttt tgggatgggg | 1846 |
| ttggttgtgt gcctacagaa tcagagtgtt gatagattat cattatctgg tgctcctggt | 1906 |
| gggagagagt gagtcgctat ctatccacta ccataaaatc ctatctttac catgaatggc | 1966 |
| tagagtagga gttgacccac ttttgatgta accgtttaac aaccattttg atgggatgga | 2026 |
| tacagtcttt tgttttattc ccatgtacaa atagaccctc atggctctgg cattgggca | 2086 |
| ataaccaaat ttcagtgatt gtttagcgga ctcgtcgaat agattatgcc ttttcagttt | 2146 |
| cactggaatt tatataccct ggagggtgat ttcaatttta tgagggtttt gagttttcca | 2206 |
| aaaaaaaaaa aaaaaaaaaa aaaaaa | 2232 |

<210> SEQ ID NO 20
<211> LENGTH: 488
<212> TYPE: PRT
<213> ORGANISM: Glycine max

<400> SEQUENCE: 20

Met Ala Ser Thr Thr Thr Ser Ser Leu Cys Thr Trp Leu Val Ala Ala
    -55                    -50                    -45

Cys Met Ser Val Thr Cys His Ala Asp Arg Thr Lys Thr Pro His Ala
-40                 -35                  -30                     -25

Met Phe Arg Ser Ser Lys Lys Ser Arg Tyr Ser Gln Phe Asn Val Cys
              -20                   -15                     -10

Arg Ser Thr His Ser Gly Lys Thr Met Ala Val Ala Leu Gln Pro Thr
         -5                  -1   1                    5

Gln Glu Ile Thr Thr Ile Lys Lys Pro Pro Thr Lys Gln Arg Arg Val
     10                     15                     20

Val Val Thr Gly Leu Gly Val Val Thr Pro Leu Gly His Glu Pro Asp
25                  30                         35                      40

Ile Phe Tyr Asn Asn Leu Leu Asp Gly Ala Ser Gly Ile Ser Glu Ile
               45                    50                     55

Glu Thr Phe Asp Cys Ala Glu Tyr Pro Thr Arg Ile Ala Gly Glu Ile
                 60                    65                        70

Lys Ser Phe Ser Thr Asp Gly Trp Val Ala Pro Lys Leu Ser Lys Arg
            75                    80                     85

Met Asp Lys Phe Met Leu Tyr Met Leu Thr Ala Gly Lys Lys Ala Leu
     90                     95                    100

Val Asp Gly Gly Ile Thr Asp Asp Val Met Asp Glu Leu Asn Lys Glu
105                110                   115                  120

Lys Cys Gly Val Leu Ile Gly Ser Ala Met Gly Gly Met Lys Val Phe
               125                   130                  135

Asn Asp Ala Ile Glu Ala Leu Arg Ile Ser Tyr Lys Lys Met Lys Pro
                 140                   145                  150

Phe Cys Val Pro Phe Ala Thr Thr Asn Met Gly Ser Ala Met Leu Ala
               155                   160                  165

```
Met Asp Leu Gly Trp Met Gly Pro Asn Tyr Ser Ile Ser Thr Ala Cys
    170             175             180

Ala Thr Ser Asn Phe Cys Ile Leu Asn Ala Ala Asn His Ile Ile Arg
185             190             195             200

Gly Glu Ala Asp Val Met Leu Cys Gly Gly Ser Asp Ala Ala Ile Ile
                205             210             215

Pro Ile Gly Leu Gly Gly Phe Val Ala Cys Arg Ala Leu Ser Gln Arg
            220             225             230

Asn Thr Asp Pro Thr Lys Ala Ser Arg Pro Trp Asp Ile Asn Arg Asp
            235             240             245

Gly Phe Val Met Gly Glu Gly Ala Gly Val Leu Leu Leu Glu Glu Leu
        250             255             260

Glu His Ala Lys Glu Arg Gly Ala Thr Ile Tyr Ala Glu Phe Leu Gly
265             270             275             280

Gly Ser Phe Thr Cys Asp Ala Tyr His Val Thr Glu Pro Arg Pro Asp
            285             290             295

Gly Ala Gly Val Ile Leu Cys Ile Glu Lys Ala Leu Ala Gln Ser Gly
            300             305             310

Val Ser Lys Glu Asp Val Asn Tyr Ile Asn Ala His Ala Thr Ser Thr
        315             320             325

Pro Ala Gly Asp Leu Lys Glu Tyr Gln Ala Leu Met His Cys Phe Gly
    330             335             340

Gln Asn Pro Glu Leu Arg Val Asn Ser Thr Lys Ser Met Ile Gly His
345             350             355             360

Leu Leu Gly Ala Ala Gly Gly Val Ala Ala Val Ala Thr Ile Gln Ala
            365             370             375

Ile Arg Thr Gly Trp Val His Pro Asn Ile Asn Leu Glu Asn Pro Asp
            380             385             390

Asn Gly Val Asp Ala Lys Val Leu Val Gly Ser Lys Lys Glu Arg Leu
            395             400             405

Asp Val Lys Ala Ala Leu Ser Asn Ser Phe Gly Phe Gly Gly His Asn
    410             415             420

Ser Ser Ile Ile Phe Ala Pro Tyr
425             430

<210> SEQ ID NO 21
<211> LENGTH: 1467
<212> TYPE: DNA
<213> ORGANISM: Glycine max
<220> FEATURE:
<221> NAME/KEY: CDS
<222> LOCATION: (1)..(1464)
<221> NAME/KEY: mat_peptide
<222> LOCATION: (169)..(1464)

<400> SEQUENCE: 21 atg gct tcg acc acc acc tcc tcc ctc tgc acg tgg ctc gtt gct gct     48
Met Ala Ser Thr Thr Thr Ser Ser Leu Cys Thr Trp Leu Val Ala Ala
    -55                 -50                 -45 tgc atg tca gtc acg tgc cac gcc gac cgc acc aaa acc cct cac gca     96
Cys Met Ser Val Thr Cys His Ala Asp Arg Thr Lys Thr Pro His Ala
-40                 -35                 -30                 -25 atg ttc cgc tcc tcc aaa aag tct cgc tac tct caa ttc aac gtt tgt    144
Met Phe Arg Ser Ser Lys Lys Ser Arg Tyr Ser Gln Phe Asn Val Cys
                -20                 -15                 -10 cga tcc act cat tct ggt aaa aca atg gct gta gct ttg caa cct acc    192
Arg Ser Thr His Ser Gly Lys Thr Met Ala Val Ala Leu Gln Pro Thr
            -5                  -1   1               5
```

-continued

```
caa gag atc acg aca ata aaa aaa cct ccc acg aag caa agg cga gtg      240
Gln Glu Ile Thr Thr Ile Lys Lys Pro Pro Thr Lys Gln Arg Arg Val
        10                  15                  20 gtt gtg aca gga ttg ggt gtg gtt aca cca ctt ggg cat gag cca gat      288
Val Val Thr Gly Leu Gly Val Val Thr Pro Leu Gly His Glu Pro Asp
 25                  30                  35                  40 atc ttc tac aat aat ttg ctt gat ggt gct agt ggc ata agc gag att      336
Ile Phe Tyr Asn Asn Leu Leu Asp Gly Ala Ser Gly Ile Ser Glu Ile
                    45                  50                  55 gaa aca ttt gat tgt gca gaa tat cca aca agg att gct ggt gaa atc      384
Glu Thr Phe Asp Cys Ala Glu Tyr Pro Thr Arg Ile Ala Gly Glu Ile
                60                  65                  70 aag tct ttc tca act gat ggc tgg gta gca cca aaa ctt tct aag aga      432
Lys Ser Phe Ser Thr Asp Gly Trp Val Ala Pro Lys Leu Ser Lys Arg
            75                  80                  85 atg gat aaa ttt atg ctc tat atg ctg aca gct ggc aaa aaa gcc ttg      480
Met Asp Lys Phe Met Leu Tyr Met Leu Thr Ala Gly Lys Lys Ala Leu
         90                  95                 100 gtt gat ggt gga att act gat gat gta atg gat gag tta aat aaa gaa      528
Val Asp Gly Gly Ile Thr Asp Asp Val Met Asp Glu Leu Asn Lys Glu
105                 110                 115                 120 aag tgt gga gtt ctg att ggg tca gca atg ggt ggc atg aag gtt ttc      576
Lys Cys Gly Val Leu Ile Gly Ser Ala Met Gly Gly Met Lys Val Phe
                    125                 130                 135 aat gat gcc atc gaa gct tta cga atc tca tat aag aag atg aag cct      624
Asn Asp Ala Ile Glu Ala Leu Arg Ile Ser Tyr Lys Lys Met Lys Pro
                140                 145                 150 ttt tgt gta cct ttt gca aca aca aat atg ggt tct gcc atg ctt gca      672
Phe Cys Val Pro Phe Ala Thr Thr Asn Met Gly Ser Ala Met Leu Ala
            155                 160                 165 atg gat ctg gga tgg atg ggc cct aat tat tct atc tct aca gct tgt      720
Met Asp Leu Gly Trp Met Gly Pro Asn Tyr Ser Ile Ser Thr Ala Cys
        170                 175                 180 gct aca agt aac ttt tgt ata ttg aat gca gca aac cat atc att aga      768
Ala Thr Ser Asn Phe Cys Ile Leu Asn Ala Ala Asn His Ile Ile Arg
185                 190                 195                 200 ggt gaa gct gat gtg atg ctt tgt gga ggc tca gat gct gct att ata      816
Gly Glu Ala Asp Val Met Leu Cys Gly Gly Ser Asp Ala Ala Ile Ile
                    205                 210                 215 cca att ggt ttg gga ggc ttt gtg gca tgc agg gca ctc tca caa agg      864
Pro Ile Gly Leu Gly Gly Phe Val Ala Cys Arg Ala Leu Ser Gln Arg
                220                 225                 230 aat act gat cct acc aaa gct tca cgc cct tgg gac att aac cgt gat      912
Asn Thr Asp Pro Thr Lys Ala Ser Arg Pro Trp Asp Ile Asn Arg Asp
            235                 240                 245 gga ttt gtc atg ggt gaa ggg gct gga gtt ttg ctt tta gag gaa ctg      960
Gly Phe Val Met Gly Glu Gly Ala Gly Val Leu Leu Leu Glu Glu Leu
        250                 255                 260 gag cat gct aag gaa aga ggt gca acc ata tat gct gaa ttc ctt ggt     1008
Glu His Ala Lys Glu Arg Gly Ala Thr Ile Tyr Ala Glu Phe Leu Gly
265                 270                 275                 280 gga agt ttc acc tgt gat gca tat cat gtg act gag ccg cgt cct gat     1056
Gly Ser Phe Thr Cys Asp Ala Tyr His Val Thr Glu Pro Arg Pro Asp
                    285                 290                 295 ggg gct ggt gtt ata ctg tgc att gaa aag gca tta gct cag tct gga     1104
Gly Ala Gly Val Ile Leu Cys Ile Glu Lys Ala Leu Ala Gln Ser Gly
                300                 305                 310 gta tca aaa gag gat gtg aat tac ata aat gca cat gcc aca tcc aca     1152
Val Ser Lys Glu Asp Val Asn Tyr Ile Asn Ala His Ala Thr Ser Thr
```

```
                    315                 320                 325
cca gct gga gat ctt aag gag tac caa gct cta atg cat tgt ttt ggt      1200
Pro Ala Gly Asp Leu Lys Glu Tyr Gln Ala Leu Met His Cys Phe Gly
    330                 335                 340 caa aac ccc gag tta aga gtg aat tct aca aaa tct atg att ggt cat      1248
Gln Asn Pro Glu Leu Arg Val Asn Ser Thr Lys Ser Met Ile Gly His
345                 350                 355                 360 cta cta ggg gca gct ggc ggt gtg gca gct gtg gcc aca ata cag gca      1296
Leu Leu Gly Ala Ala Gly Gly Val Ala Ala Val Ala Thr Ile Gln Ala
                365                 370                 375 att agg aca ggg tgg gtt cat ccc aat atc aac cta gaa aac cca gat      1344
Ile Arg Thr Gly Trp Val His Pro Asn Ile Asn Leu Glu Asn Pro Asp
            380                 385                 390 aac gga gtg gat gct aaa gtg ctt gtt ggc tca aag aaa gag aga ctg      1392
Asn Gly Val Asp Ala Lys Val Leu Val Gly Ser Lys Lys Glu Arg Leu
        395                 400                 405 gat gtc aag gca gcc ttg tcg aat tca ttt ggt ttt ggg ggt cac aat      1440
Asp Val Lys Ala Ala Leu Ser Asn Ser Phe Gly Phe Gly Gly His Asn
    410                 415                 420 tct tca atc ata ttt gca cca tac tag                                  1467
Ser Ser Ile Ile Phe Ala Pro Tyr
425                 430

<210> SEQ ID NO 22
<211> LENGTH: 1299
<212> TYPE: DNA
<213> ORGANISM: Glycine max
<220> FEATURE:
<221> NAME/KEY: CDS
<222> LOCATION: (1)..(1296)

<400> SEQUENCE: 22 atg gct gta gct ttg caa cct acc caa gag atc acg aca ata aaa aaa       48
Met Ala Val Ala Leu Gln Pro Thr Gln Glu Ile Thr Thr Ile Lys Lys
  1               5                  10                  15 cct ccc acg aag caa agg cga gtg gtt gtg aca gga ttg ggt gtg gtt       96
Pro Pro Thr Lys Gln Arg Arg Val Val Val Thr Gly Leu Gly Val Val
                20                  25                  30 aca cca ctt ggg cat gag cca gat atc ttc tac aat aat ttg ctt gat      144
Thr Pro Leu Gly His Glu Pro Asp Ile Phe Tyr Asn Asn Leu Leu Asp
            35                  40                  45 ggt gct agt ggc ata agc gag att gaa aca ttt gat tgt gca gaa tat      192
Gly Ala Ser Gly Ile Ser Glu Ile Glu Thr Phe Asp Cys Ala Glu Tyr
        50                  55                  60 cca aca agg att gct ggt gaa atc aag tct ttc tca act gat ggc tgg      240
Pro Thr Arg Ile Ala Gly Glu Ile Lys Ser Phe Ser Thr Asp Gly Trp
 65                  70                  75                  80 gta gca cca aaa ctt tct aag aga atg gat aaa ttt atg ctc tat atg      288
Val Ala Pro Lys Leu Ser Lys Arg Met Asp Lys Phe Met Leu Tyr Met
                 85                  90                  95 ctg aca gct ggc aaa aaa gcc ttg gtt gat ggt gga att act gat gat      336
Leu Thr Ala Gly Lys Lys Ala Leu Val Asp Gly Gly Ile Thr Asp Asp
            100                 105                 110 gta atg gat gag tta aat aaa gaa aag tgt gga gtt ctg att ggg tca      384
Val Met Asp Glu Leu Asn Lys Glu Lys Cys Gly Val Leu Ile Gly Ser
        115                 120                 125 gca atg ggt ggc atg aag gtt ttc aat gat gcc atc gaa gct tta cga      432
Ala Met Gly Gly Met Lys Val Phe Asn Asp Ala Ile Glu Ala Leu Arg
    130                 135                 140 atc tca tat aag aag atg aag cct ttt tgt gta cct ttt gca aca aca      480
Ile Ser Tyr Lys Lys Met Lys Pro Phe Cys Val Pro Phe Ala Thr Thr
```

```
                145                 150                 155                 160
aat atg ggt tct gcc atg ctt gca atg gat ctg gga tgg atg ggc cct              528
Asn Met Gly Ser Ala Met Leu Ala Met Asp Leu Gly Trp Met Gly Pro
                165                 170                 175 aat tat tct atc tct aca gct tgt gct aca agt aac ttt tgt ata ttg              576
Asn Tyr Ser Ile Ser Thr Ala Cys Ala Thr Ser Asn Phe Cys Ile Leu
            180                 185                 190 aat gca gca aac cat atc att aga ggt gaa gct gat gtg atg ctt tgt              624
Asn Ala Ala Asn His Ile Ile Arg Gly Glu Ala Asp Val Met Leu Cys
        195                 200                 205 gga ggc tca gat gct gct att ata cca att ggt ttg gga ggc ttt gtg              672
Gly Gly Ser Asp Ala Ala Ile Ile Pro Ile Gly Leu Gly Gly Phe Val
    210                 215                 220 gca tgc agg gca ctc tca caa agg aat act gat cct acc aaa gct tca              720
Ala Cys Arg Ala Leu Ser Gln Arg Asn Thr Asp Pro Thr Lys Ala Ser
225                 230                 235                 240 cgc cct tgg gac att aac cgt gat gga ttt gtc atg ggt gaa ggg gct              768
Arg Pro Trp Asp Ile Asn Arg Asp Gly Phe Val Met Gly Glu Gly Ala
                245                 250                 255 gga gtt ttg ctt tta gag gaa ctg gag cat gct aag gaa aga ggt gca              816
Gly Val Leu Leu Leu Glu Glu Leu Glu His Ala Lys Glu Arg Gly Ala
            260                 265                 270 acc ata tat gct gaa ttc ctt ggt gga agt ttc acc tgt gat gca tat              864
Thr Ile Tyr Ala Glu Phe Leu Gly Gly Ser Phe Thr Cys Asp Ala Tyr
        275                 280                 285 cat gtg act gag ccg cgt cct gat ggg gct ggt gtt ata ctg tgc att              912
His Val Thr Glu Pro Arg Pro Asp Gly Ala Gly Val Ile Leu Cys Ile
    290                 295                 300 gaa aag gca tta gct cag tct gga gta tca aaa gag gat gtg aat tac              960
Glu Lys Ala Leu Ala Gln Ser Gly Val Ser Lys Glu Asp Val Asn Tyr
305                 310                 315                 320 ata aat gca cat gcc aca tcc aca cca gct gga gat ctt aag gag tac              1008
Ile Asn Ala His Ala Thr Ser Thr Pro Ala Gly Asp Leu Lys Glu Tyr
                325                 330                 335 caa gct cta atg cat tgt ttt ggt caa aac ccc gag tta aga gtg aat              1056
Gln Ala Leu Met His Cys Phe Gly Gln Asn Pro Glu Leu Arg Val Asn
            340                 345                 350 tct aca aaa tct atg att ggt cat cta cta ggg gca gct ggc ggt gtg              1104
Ser Thr Lys Ser Met Ile Gly His Leu Leu Gly Ala Ala Gly Gly Val
        355                 360                 365 gca gct gtg gcc aca ata cag gca att agg aca ggg tgg gtt cat ccc              1152
Ala Ala Val Ala Thr Ile Gln Ala Ile Arg Thr Gly Trp Val His Pro
    370                 375                 380 aat atc aac cta gaa aac cca gat aac gga gtg gat gct aaa gtg ctt              1200
Asn Ile Asn Leu Glu Asn Pro Asp Asn Gly Val Asp Ala Lys Val Leu
385                 390                 395                 400 gtt ggc tca aag aaa gag aga ctg gat gtc aag gca gcc ttg tcg aat              1248
Val Gly Ser Lys Lys Glu Arg Leu Asp Val Lys Ala Ala Leu Ser Asn
                405                 410                 415 tca ttt ggt ttt ggg ggt cac aat tct tca atc ata ttt gca cca tac              1296
Ser Phe Gly Phe Gly Gly His Asn Ser Ser Ile Ile Phe Ala Pro Tyr
            420                 425                 430 tag                                                                          1299

<210> SEQ ID NO 23
<211> LENGTH: 432
<212> TYPE: PRT
<213> ORGANISM: Glycine max

<400> SEQUENCE: 23
```

-continued

```
Met Ala Val Ala Leu Gln Pro Thr Gln Glu Ile Thr Thr Ile Lys Lys
 1               5                  10                 15
Pro Pro Thr Lys Gln Arg Arg Val Val Thr Gly Leu Gly Val Val
             20                  25                  30
Thr Pro Leu Gly His Glu Pro Asp Ile Phe Tyr Asn Asn Leu Leu Asp
             35                  40                  45
Gly Ala Ser Gly Ile Ser Glu Ile Glu Thr Phe Asp Cys Ala Glu Tyr
         50                  55                  60
Pro Thr Arg Ile Ala Gly Glu Ile Lys Ser Phe Ser Thr Asp Gly Trp
 65                  70                  75                  80
Val Ala Pro Lys Leu Ser Lys Arg Met Asp Lys Phe Met Leu Tyr Met
                 85                  90                  95
Leu Thr Ala Gly Lys Lys Ala Leu Val Asp Gly Ile Thr Asp Asp
                100                 105                 110
Val Met Asp Glu Leu Asn Lys Glu Lys Cys Gly Val Leu Ile Gly Ser
             115                 120                 125
Ala Met Gly Gly Met Lys Val Phe Asn Asp Ala Ile Glu Ala Leu Arg
         130                 135                 140
Ile Ser Tyr Lys Lys Met Lys Pro Phe Cys Val Pro Phe Ala Thr Thr
145                 150                 155                 160
Asn Met Gly Ser Ala Met Leu Ala Met Asp Leu Gly Trp Met Gly Pro
                165                 170                 175
Asn Tyr Ser Ile Ser Thr Ala Cys Ala Thr Ser Asn Phe Cys Ile Leu
            180                 185                 190
Asn Ala Ala Asn His Ile Ile Arg Gly Glu Ala Asp Val Met Leu Cys
            195                 200                 205
Gly Gly Ser Asp Ala Ala Ile Ile Pro Ile Gly Leu Gly Gly Phe Val
        210                 215                 220
Ala Cys Arg Ala Leu Ser Gln Arg Asn Thr Asp Pro Thr Lys Ala Ser
225                 230                 235                 240
Arg Pro Trp Asp Ile Asn Arg Asp Gly Phe Val Met Gly Glu Gly Ala
                245                 250                 255
Gly Val Leu Leu Leu Glu Glu Leu Glu His Ala Lys Glu Arg Gly Ala
            260                 265                 270
Thr Ile Tyr Ala Glu Phe Leu Gly Gly Ser Phe Thr Cys Asp Ala Tyr
        275                 280                 285
His Val Thr Glu Pro Arg Pro Asp Gly Ala Gly Val Ile Leu Cys Ile
        290                 295                 300
Glu Lys Ala Leu Ala Gln Ser Gly Val Ser Lys Glu Asp Val Asn Tyr
305                 310                 315                 320
Ile Asn Ala His Ala Thr Ser Thr Pro Ala Gly Asp Leu Lys Glu Tyr
                325                 330                 335
Gln Ala Leu Met His Cys Phe Gly Gln Asn Pro Glu Leu Arg Val Asn
            340                 345                 350
Ser Thr Lys Ser Met Ile Gly His Leu Leu Gly Ala Ala Gly Gly Val
            355                 360                 365
Ala Ala Val Ala Thr Ile Gln Ala Ile Arg Thr Gly Trp Val His Pro
        370                 375                 380
Asn Ile Asn Leu Glu Asn Pro Asp Asn Gly Val Asp Ala Lys Val Leu
385                 390                 395                 400
Val Gly Ser Lys Lys Glu Arg Leu Asp Val Lys Ala Ala Leu Ser Asn
                405                 410                 415
```

```
Ser Phe Gly Phe Gly Gly His Asn Ser Ser Ile Ile Phe Ala Pro Tyr
        420                 425                 430
```

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:5' primer
      for amplification of the mature maize KASII fragment

<400> SEQUENCE: 24
catatggctg ttgccttaca agc                                    23

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:3'primer
      for amplification of the mature maize KASII fragment

<400> SEQUENCE: 25
ctcgagtcac ttaaaggggg caaagag                                27

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: 5'primer
      for amplification of the first and second mature soybean KASII
      fragments

<400> SEQUENCE: 26
acgtacgtca tatggctgta gctttgcaac ct                          32

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: 3'primer
      for amplification of the first mature soybean KASII
      fragment

<400> SEQUENCE: 27
acgtacgtga gctctcactt gtaaggtgca aatatg                      36

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: 3'primer
      for amplification of the second mature soybean KASII
      fragment

<400> SEQUENCE: 28
acgtacgtga gctcctagta tggtgcaaat                             30

<210> SEQ ID NO 29
<211> LENGTH: 1262
<212> TYPE: DNA
<213> ORGANISM: Artificial Sequence
<220> FEATURE:
<223> OTHER INFORMATION: Description of Artificial Sequence:globulin
      promoter -continued

```
<400> SEQUENCE: 29
ttttggtacc gccgagtgcc atccttggac actcgataaa gtatatttta ttttttttat      60
tttgccaacc aaacttttg tggtatgttc ctacactatg tagatctaca tgtaccattt     120
tggcacaatt acaaaaatgt tttctataac tattagattt agttcgttta tttgaatttc     180
ttcggaaaat tcacatatga actgcaagtc actcgaaaca tgaaaaaccg tgcatgcaaa     240
ataaatgata tgcatgttat ctagcacaag ttacgaccga tttcagaagc agaccagaat     300
cttcaagcac catgctcact aaacatgacc gtgaacttgt tatccagttg tttaaaaatt     360
gtataaaaca caaataaagt cagaaattaa tgaaacttgt ccacatgtca tgatatcata     420
tatagaggtt gtgataaaaa tttgatattg tttcggtaaa gttgtgacgt actatgtgta     480
gaaacctaag tgacctacac ataaaatcat agagtttcaa tgtagttcac tcgacaaaga     540
ctttgtcaag tgtccgataa aaagtattca gcaaagaagc cgttgtcgat ttactgttcg     600
tcgagatctc tttgccgagt gtcacactag gcaaagtctt tacggagtgt ttttcaggct     660
ttgacactcg gcaaagcgct cgattccagt agtgacagta atttgcatca aaaatagccg     720
agagatttaa aatgagtcaa ctaatagacc aactaattat tagctattag tcgttagctt     780
ctttaatcta agctaaaacc aactaatagc ttatttgttg aattacaatt agctcaacgg     840
aattctctgt tttttctata aaaagggaa actgccctc atttacagca aactgtccgc     900
tgcctgtcgt ccagatacaa tgaacgtacc tagtaggaac tcttttacac gctcggtcgc     960
tcgccgcgga tcggagtccc aggaacacga caccactgtg gaacacgaca aagtctgctc    1020
agaggcggcc acaccctggc gtgcaccgag ccggagcccg gataagcacg gtaaggagag    1080
tacggcggga cgtggcgacc cgtgtgtctg ctgccacgca gccttcctcc acgtagccgc    1140
gcggccgcgc cacgtaccag ggcccggcgc tggtataaat gcgcgccacc tccgctttag    1200
ttctgcatac agccaaccca acacacaccc gagcatatca cagtgacact acaccatgga    1260
aa                                                                  1262
```

US 6,323,395 B1

NUCLEOTIDE SEQUENCES OF MAIZE AND SOYBEAN β-KETOACYL-ACYL CARRIER PROTEIN SYNTHASE II AND THEIR USE IN THE REGULATION OF FATTY ACID CONTENT OF OIL

RELATED APPLICATIONS

This application claims the priority of U.S. Provisional Patent Application No. 60/068,784, filed Dec. 24, 1997.

FIELD OF INVENTION

This invention relates to the preparation and use of nucleic acid fragments or genes encoding maize and soybean βKetoacyl-Acyl Carrier Protein Synthase II (KAS II) enzymes to create transgenic plants having altered oil profiles.

BACKGROUND OF THE INVENTION

Oils produced by plants can be found in a wide variety of products including soaps, lubricants, and foods. Interestingly, different plant species synthesize various oil types. For example, coconut and palm plants produce oils that are abundant in fatty acids having medium chain lengths (10–12 carbon atoms). These oils are used in the manufacture of soaps, detergents and surfactants and represent a US market size greater than $350 million per year. Other plants, such as rape, produce oils abundant in long chain fatty acids (22 carbon atoms) and are used as lubricants and anti-slip agents. Additional applications of plant oils include their use in plasticizers, coatings, paints, varnishes and cosmetics (Volker et al., (1992) Science 257:72–74; Ohlrogge, (1994) Plant Physiol. 104:821–826). However, the predominant use of plant oils is in the production of food and food products.

The characteristics of oils are determined predominately by the number of carbon atoms comprising the fatty acid chain. Most oils derived from plants are composed of varying amounts of palmitic (16:0), stearic (18:0), oleic (18:1), linoleic (18:2) and linolenic (18:3) fatty acids. Palmitic and stearic acids are 16- and 18-carbon long saturated fatty acids, respectively. Conventionally, they are designated as "saturated" since the fatty acid chains have no double bonds and therefore contain the maximal number of hydrogen atoms possible. Saturated fatty acids are linear molecules and tend to form self-stacked structures thereby resulting in high melting temperatures. For example, animal fats, which are solid at room temperature, are typically high in saturated fatty acids. The other predominant fatty acids found in plant oils, oleic, linoleic, and linolenic, are 18-carbon long fatty acid chains having one, two, and three double bonds therein, respectively. Oleic acid is typically considered a mono-unsaturated fatty acid, whereas linoleic and linolenic are considered to be poly-unsaturated fatty acids. These fatty acid chains are nonlinear due to bending induced by the insertion of the double bond in the cis conformation. Double bond insertion decreases melting point due to the inability of the fatty acid molecules to self-stack. For example, vegetable oils, which are typically liquid at room temperature, are high in unsaturated fatty acids.

Over the years, vegetable oils have gradually replaced animal-derived oils and fats as the major source of dietary fat intake. However, saturated fat in most industrialized nations has remained at 15 to 20% of total caloric intake. The United States Department of Agriculture has recently recommended that saturated fats make up less than 10% of daily caloric intake. To facilitate consumer awareness, current labeling guidelines issued by the United States Food and Drug Administration now require total saturated fatty acid levels be less than 1.0 g per 14 g serving to receive the "low-sat" label and less than 0.5 g per 14 g serving to receive the "no-sat" label. This means that the saturated fatty acid content of plant oils would need be less than 7% and 1.75% to receive the "low sat" and "no sat" label, respectively. Therefore, there has been a surge in increased consumer demand for "low-sat" oils. To date, this has been met principally with canola oil, and to a much lesser degree with sunflower, and safflower oils.

The total saturated fatty acid level of corn oil, approximately 13.9%, does not meet the labeling guidelines discussed above. On average, corn oil is comprised of 11.5% palmitic acid, 2.2% stearic acid, 26.6% oleic acid, 58.7% linoleic acid, and 0.8% linolenic acid. Corn oil also contains 0.26 arachidic acid, a twenty-carbon saturated fatty acid (Dunlap et. al., (1995) J. Amer. Oil Chem. Soc. 72:981–987). The fatty acid composition of corn oil instills it with properties that are most desirable in edible oils. These include properties such as heat stability, flavor, and long shelf life. However, consumer demand for "low sat" oils has resulted in a significant decrease in corn oil utilization and thus market share. Therefore, a corn oil with low levels of saturated fatty acids is highly desirable in that it would meet the consumer demand for healthier oils while having most or all of the properties that made corn oil popular in the past and a preferred oil for many uses.

Although corn oil with low levels of saturated fatty acids is desirable, there is also a demand for corn oil having high levels of saturated fatty acids. For example, about half of the total consumption of vegetable oils is in the form of margarine and shortening. However, the use of corn oil for these products requires chemical modification of the oil due to its low melting point. Typically, an increased melting point is achieved through catalytic hydrogenation which increases the level of saturated fatty acids. In this process, hydrogen atoms are added at double bonds found in the fatty acid through the use of a catalyst. An additional side reaction that occurs during hydrogenation is the substantial conversion of the naturally occurring cis double bonds to the trans isomer, which is more stable. There have been some controversies regarding health risks associated with intake of oils containing trans double bonds. In a recent study, it was shown that a diet high in trans isomer consumption actually raised serum lipoprotein profiles and cholesterol levels (Mensink and Katan (1990) N. Eng. J. Med. 323:439–445). Therefore, production of oil containing a higher content of saturated fatty acids would reduce the need for hydrogenation in margarine and shortening production thereby reducing the content of trans isomers in the diet. In addition, partial hydrogenation typically increases cost an additional 2 to 3 cents per pound of oil. Therefore, a corn oil with naturally high saturates levels is also highly desirable for production of margarine and shortening since this would fulfill a market need while reducing manufacture cost.

Corn is typically not considered to be an oil crop as compared to soybean, canola, sunflower and the like. In fact, the oil produced by corn is considered to be a byproduct of the wet milling process used to extract starch. Because of this, there has been little interest in modifying the saturate levels of corn oil until that disclosed herein.

As disclosed herein, the saturate levels of fatty acids in corn oil can be altered by modifying the expression levels of β-Ketoacyl-Acyl carrier protein Synthase II (KAS II). KAS II catalyzes the elongation of fatty acid intermediates from 16:0-acyl carrier protein (ACP) (palmitoyl-ACP) to 18:0-ACP (stearoyl-ACP) by the addition of a two carbon moiety from malonyl-ACP to 16:0-ACP. During fatty acid biosynthesis, KAS II competes with the palmitoyl-acyl carrier protein thioesterase (PTE) for 16:0-ACP substrate. PTE terminates chain elongation by hydrolyzing the ACP moiety from the fatty acid intermediate, thereby liberating free fatty acids which are ultimately incorporated into seed oil. In this way, PTE is in large part responsible for regulating the amount of 16:0 in the triacylglycerol fraction. However, the equilibrium established by the competition of PTE and KAS II for palmitoyl-ACP plays a large role in fatty acid profiles observed in corn oil.

Over-expression of KAS II in plants is a strategy to reduce the amount of 16:0 in seed oil by shifting the equilibrium of palmitoyl-ACP to stearoyl-ACP. An increase in KAS II concentration forces the carbon flux toward 18:0-ACP, which is rapidly converted to 18:1-ACP by stearoyl-ACP desaturase (delta-9 desaturase). The amount of 16:0-ACP available for the thioesterase is effectively depleted, and the amount of saturated fatty acid in seed oil in the form of 16:0 is reduced. Alternatively, down-regulation of KAS II in plants is a strategy to increase the amount of 16:0 in seed oil by shifting the equilibrium from stearoyl-ACP production to palmitoyl-ACP production.

SUMMARY OF THE INVENTION

In the present invention, KAS II has been isolated and cloned from maize and soybean. The saturate level of oils found in plant cells can be altered by modifying the expression and activity levels of KAS II within the cell.

One aspect of the disclosed invention is genes and nucleic acid fragments encoding maize and soybean KAS II. Maize and soybean KAS II elongates acyl-acyl carrier protein units (acyl-ACP) having 16 carbon atoms into acyl-ACP units having 18 carbon atoms by the addition of malonyl-ACP.

Another aspect of the invention relates to altering saturate levels within a cell by modifying expression levels of KAS II. The genes and nucleic acid fragments disclosed herein can be used to alter saturate levels by placing said genes and fragments in the antisense orientation. Plants being transformed with KAS II in the antisense orientation results in the oils of said plants having increased 16:0 and increased total saturate levels. Results similar to those produced by antisense techniques can also be produced through the use of ribozymes designed specifically for either maize KAS II or soybean KAS II.

Another aspect of the invention relates to altering saturate levels within a cell by modifying expression levels of KAS II through expressing the genes and nucleic fragments thereof in the sense orientation. Expression of said genes and fragments thereof in the sense orientation can result in cosuppression effects. Plants being transformed with KAS II in the sense orientation producing cosuppression effects produce plant oils having increased 16:0 and increased total saturate levels.

In yet a further aspect, the genes and fragments disclosed herein can alter the saturate levels of plant oils when in the sense orientation by over-expressing the proteins encoded thereby. Over-expressing maize or soybean KAS II in a plant can produce oils having lowered 16:0 and lowered total saturate levels.

An additional aspect of the present invention is the production of a chimeric gene using the genes and nucleic acid fragments disclosed herein in combination with promoter regulatory elements and the use of said chimeric genes within a plant cell.

Yet an additional aspect of the present invention is the transformation of plant species disclosed herein with said chimeric genes.

Other aspects, embodiments, advantages, and features of the present invention will become apparent from the following specification.

DETAILED DESCRIPTION OF THE INVENTION

The present invention relates to methods and compositions for obtaining plant oils having altered saturate levels. The following phrases and terms are defined below:

By "altered saturate levels" is meant that the level of total saturated fatty acids of a plant oil produced by a modified plant is different from that of a normal or non-modified plant. Alterations in total saturate levels can be achieved by either increasing or decreasing saturated fatty acids.

By "antisense RNA" is meant an RNA transcript that comprises sequences complementary to a target RNA and/or mRNA or portions thereof and that blocks the expression of a target gene by interfering with the processing, transport, and/or translation of its primary transcript and/or mRNA. The complementarity may exist with any part of the target RNA, i.e., at the 5' non-coding sequences, 3' non-coding sequence, introns, or the coding sequence. Antisense RNA is typically a complement (mirror image) of the sense RNA.

By "cDNA" is meant DNA that is complementary to and derived from a mRNA.

By "chimeric DNA construction" is meant a recombinant DNA containing genes or portions thereof from one or more species in either the sense or antisense orientation.

By "complementarity" is meant a nucleic acid that can form hydrogen bond(s) with other nucleic acid sequences either through traditional Watson-Crick or other non-traditional types of base paired interactions.

By "constitutive promoter" is meant promoter elements that direct continuous gene expression in all cell types and at all times (i.e., actin, ubiquitin, CaMV 35S, 35T, and the like).

By "cosuppression" is meant the introduction of a foreign gene having substantial homology to an endogenous gene, and in a plant cell causes the reduction in activity of the foreign gene and/or the endogenous protein product.

By "developmental specific" promoter is meant promoter elements responsible for gene expression at specific plant developmental stages, such as in early or late embryogenesis.

By "enhancer" is meant nucleotide sequence elements which can stimulate promoter activity such as those from maize streak virus (MSV) and alcohol dehydrogenase intron 1.

By "enzymatic nucleic acid molecule" is meant all nucleic acid molecules with enzymatic activity having complimentarily in a substrate binding region to a specified gene target, and which is able to specifically cleave that target. The term enzymatic nucleic acid is used interchangeably with phrases such as ribozymes, catalytic RNA, enzymatic RNA, catalytic DNA, nucleozyme, DNAzyme, RNA enzyme, and the like. All of these terminologies describe ucleic acid molecules with enzymatic activity.

By "expression" as used herein, is meant the transcription and stable accumulation of the enzymatic nucleic acid molecules, mRNA, and/or the antisense RNA inside a plant cell. Expression of genes also involves transcription of the gene and translation of the MRNA into precursor or mature proteins.

By "foreign" or "heterologous gene" is meant a gene encoding a protein whose exact amino acid sequence is not normally found in the host cell, but is introduced by standard gene transfer techniques.

By "gene" is meant to include all genetic material involved in protein expression including chimeric DNA constructions, genes, plant genes and portions thereof.

By "genome" is meant genetic material contained in each cell of an organism and/or virus.

By "inducible promoter" is meant promoter elements which are responsible for expression of genes in response to a specific signal, such as: physical stimuli (heat shock genes); light (RUBP carboxylase); hormone (Em); metabolites and stress.

By "modified plant" is meant a plant wherein the mRNA, protein levels or protein specific activity levels KAS II have been altered relative to that seen in a unmodified plant. Modification can be achieved by methods such as antisense, cosuppression, over-expression, or ribozymes.

By "plant" is meant a photosynthetic organism including both eukaryotes and prokaryotes.

By "promoter regulatory element" is meant nucleotide sequence elements within a nucleic fragment or gene which controls the expression of that nucleic acid fragment or gene. Promoter sequences provide the recognition for RNA polymerase and other transcriptional factors required for efficient transcription. Promoter regulatory elements from a variety of sources can be used efficiently in plant cells to express sense and antisense gene constructs. They can also be used to express ribozymes. Promoter regulatory elements are also meant to include constitutive, tissue-specific, developmental-specific, inducible promoters and the like. Promoter regulatory elements may also include certain enhancer sequence elements that improve transcriptional efficiency.

By "tissue-specific" promoter is meant promoter elements responsible for gene expression in specific cell or tissue types, such as the leaves or seeds (i.e., zein, oleosin, napin, ACP, globulin and like).

By "transgenic plant" is meant a plant expressing a chimeric gene introduced through transformation efforts.

In plants, KAS II is solely responsible for the elongation of palmitoyl-ACP to stearoyl-ACP. This occurs by KAS II enzymatically adding malonyl-ACP, a 2-carbon moiety, to palmitoyl-ACP, a 16 carbon moiety, thereby producing stearoyl-ACP, a 18-carbon moiety. It has been found herein that changes in the levels of KAS II in plant cells alters fatty acid profiles thereby altering saturate levels in plant oils.

In corn seed oil, the predominant fatty acids are linoleic acid (18:2 at about 59%), oleic acid (18:1 at about 26%) and palmitic (16:0 at about 11%), with stearic acid (18:0) generally comprising at about 2.5% or less (Glover and Mertz, (1987) in: Nutritional Quality of Cereal Grains: genetic and agronomic improvement., p.183–336, (eds. Olson, R. A. and Frey, K. J.) Amer. Soc. Agronomy, Inc., Madison, Wis.; Fitch-Haumann, (1985) J. Am. Oil. Chem. Soc. 62:1524–1531). Biosynthesis of fatty acids is initiated in the plastids where they are synthesized as thioesters of acyl carrier protein (ACP) by a fatty acid synthase complex. More specifically, fatty acid production is accomplished by a series of condensation reactions involving addition of malonyl-ACP sequentially to a growing fatty acid acyl chain by the enzyme KAS I. Most fatty acid-ACP units reach carbon chain lengths of 16 and are then elongated to 18 carbon units by KAS II. The vast majority of C18 fatty acids then become desaturated by stearoyl-ACP -9 desaturase at the C9 position to produce oleyl-ACP, which can be hydrolyzed to form oleic acid.

Both saturated and unsaturated fatty acid-ACP units are hydrolyzed by acyl-ACP thioesterases to produce free fatty acids. These free fatty acids then cross the plastid membrane to the cytosol where they are incorporated into plant oils (Somerville and Browse, (1991) Science 252:80–87; Browse and Sommerville (1991) Annu. Rev Plant Physiol. Plant Mol. Biol. 42:467–506; Harwood (1989) Critical Reviews in Plant Sci. 8:1–43; Chasan (1995) Plant Cell 7:235–237).

However, since stearoyl-ACP Δ-9 desaturase is not rate-limiting, the key components in determining saturate levels is the ability of KAS II to elongate a palmitoyl-ACP molecule to stearoyl-ACP before hydrolysis by the palmitoyl-ACP thioesterase can occur. Therefore, increasing or reducing levels of KAS II in plants or altering the total enzymatic activity of said enzyme will alter the overall rates of 18-carbon flux and thus saturate and unsaturate levels in the oil produced by said plant.

As further described herein, maize and soybean KAS II may be used to modify the saturate levels in oils produced by transgenic plants. Preferably, genes and nucleic fragments encoding for KAS II are isolated from either maize or soybean. More preferably the KAS II sequences are those disclosed herein as SEQ ID NO:5, SEQ ID NO:7, SEQ ID NO:8, SEQ ID NO:14, SEQ ID NO:16, SEQ ID NO:17, SEQ ID NO:19, SEQ ID NO:21, and SEQ ID NO;22.

By altering KAS II gene expression or the level of the protein's activity, the saturate levels of a plant oil may be modified. Alterations in KAS II expression levels can be achieved using antisense techniques. Antisense inhibition has been used to inhibit a variety of plant target genes (van der Krol et al., (1988) Gene 72:45–50; Ecker et al., (1986) Proc. Natl. Acad. Sci. USA 83:5372–5376; van der Krol et al., (1988) Biotechniques 6:958–976; Knutzon et al.,(1992) Proc. Natl. Acad. Sci. 89:2624). Typically, an antisense probe can be made using polymerase chain reaction techniques, hereinafter PCR, wherein small oligonucleotide primers are used to make an DNA molecule in the 5' to 3' direction that is the complement (mirror image) of the coding or sense strand of said DNA. The DNA encoding the antisense RNA molecule is typically placed 3' to a desired promoter regulatory element and plant cells of interest are transformed as described herein. The general methods and teachings of antisense have been disclosed in Shewmaker et al., in U.S. Pat. Nos. 5,107,065 and 5,453,566, which are incorporated by reference.

The length of the antisense portion needed to produce a phenotypic effect can vary. For example, phenotypic effects due to antisense have been shown using complete cDNA sequences (Sheehy et al., Proc. Natl. Acad. Sci. USA (1988) 85:8805–8809) as well as partial cDNA sequences (Cannon et al., Plant Molec. Biol. (1990) 15:39–47). There is also evidence that the 3' noncoding sequences and fragments of 5' coding sequences containing as few as 41 base pairs can both have utility in producing antisense effects (Ch'ng et al., (1989) Proc. Natl. Acad. Sci. USA, 86:10006–10010; Cannon et al., Plant Molec. Biol. (1990) 15:39–47).

It is expected that genomic DNA sequences associated with either maize or soybean KAS II, including the 5' and 3' noncoding regions and intron sequences, can be used to create chimeric genes constructs encoding for antisense RNA. Isolation and cloning of said genomic DNA encoding maize or soybean KAS II can be performed using a variety of methods detailed in Sambrook et al., (Molecular Cloning, A Laboratory Manual, 2$^{nd}$ Ed. (1989) Cold Spring Harbor Laboratory Press), which is incorporated herein by reference.

As further described, the nucleic acid fragments and genes encoding maize or soybean KAS II can be cloned in the antisense orientation. Preferably, the maize globulin and maize ubiquitin promoters can be used to produce the chimeric genes for plant transformation. Maize tissues transformed with maize or soybean KAS II genes and fragments in the antisense orientation can produce plant oils having altered fatty acid profiles relative to nontransformed controls. When using the KAS II gene or fragments in the antisense orientation, it is most desirable to increase 16:0 levels within the oils produced by the transgenic plant. Typically, as stated previously, the 16:0 levels in maize oil are about 11.0%; however, when using the KAS II gene or fragments thereof in the antisense orientation, the 16:0 levels in maize plants can be made higher.

In addition to antisense, another way to manipulate gene or nucleic acid expression is with cosuppression. The use of cosuppression to alter expression of endogenous plant genes is well described in the art. Typically, a genomic clone, a cDNA clone, or portions thereof are inserted in the sense orientation 3' to the promoter regulatory element of choice.

Cosuppression of endogenous genes has been demonstrated using entire cDNA sequences (Napoli et al., (1990) Plant Cell 2:279–289; van der Krol et al., (1990) 2:291–299) as well as a partial cDNA sequence (Smith et al., (1990) Mol. Gen. Genetics 224:477–481). Endogenous genes can also be inhibited by the introduction of noncoding regions of a gene of interest into a cell (Brusslan et. al., (1993) Plant Cell 5:667–677; Matzke et al., (1993) Plant Molecular Biology 16:821–830) In a related aspect, promoter regulatory elements corresponding to the endogenous gene of interest have also been shown to be suitable agents for inducing cosuppression events and are included herein (Brusslan et al., (1993) Plant Cell 5:667–677; Kinney (1996) Development of genetically engineered oilseeds. 12th International Symposium on Plant Lipids, Toronto, Canada Jul. 7–12, 1996). Therefore, another aspect of the present invention is the altering of saturate levels in plant oil composition through inhibition of genes expressing maize KAS II using cosuppression techniques.

For cosuppression, the nucleic acid fragments and genes encoding maize KAS II are cloned in the sense orientation.

Maize tissues transformed with maize KAS II genes and fragments in the sense orientation can produce plant oils having altered fatty acid profiles relative to nontransformed controls. When using the KAS II gene or fragments in the sense orientation resulting in a cosuppression effect, it is most desirable to increase 16:0 levels within the oils produced by the transgenic plant. Typically, as stated previously, the 16:0 levels are about 11.0%; however, when using the KAS II gene or fragments thereof in the sense orientation resulting in a cosuppression effect, the 16:0 levels in maize transgenic plants can be made higher.

Yet another aspect of the present invention is the altering of saturate levels in plant oils by inhibiting expression of maize KAS II using ribozymes. Ribozymes can be targeted to virtually any RNA transcript and efficient cleavage has been achieved in vivo and in vitro (Zaug et al., (1986) Nature 324:429; Kim et al., (1987) Proc. Natl. Acad. Sci. USA 84:8788; Dreyfus, (1988) Einstein Quarterly J. Bio. Med. 6:92; Haselof and Gerlach (1988) Nature 334:585; Cech (1988) J. Amer. Med. Assoc. 260:3030; and Jefferies et al., (1989) Nucl. Acids. Res. 17:1371). Because of their sequence-specificity, ribozymes may be used as efficient tools to modulate gene expression in a variety of organisms (Usman and McSwiggen, (1995) Ann. Rep. Med. Chem. 30:285–294; and Christoffersen and Marr, (1995) J. Med. Chem. 38:2023–2037). Methods of producing ribozymes against targets are disclosed in the PCT publication WO097/10328, which is incorporated herein by reference. Expressing ribozymes targeted to RNA encoding maize or soybean KAS II genes or fragments is another mechanism for down regulation of mRNA levels, decreasing protein levels and subsequent alterations in the saturate levels of plant oils.

Another mechanism by which plant oils can be modified is by over-expressing maize or soybean KAS II. This can be achieved by placing the genes or nucleic acid fragments for these proteins in the sense orientation 3' to the promoter regulatory element of choice. These chimeric genes can then be transformed into plants, thereby producing plant oils having altered saturate levels relative to nontransformed controls. Over-expressing KAS II in plants causes the 16:0 levels in maize plants to range from about 4.8 to about 9.5%; preferably from about 4.8 to about 7.0%; more preferably from about 4.8 to about 4.9%, and most preferred 3.0%. The total saturate levels range from about 3.0 to about 8.3%; more preferably about 3.0 to about 6.8%, and most preferred 3.0%.

In addition to using these genes and nucleic fragments for maize, other plant species which may be modified include but are not limited to soybean, Brassicaceae sp., canola, rape, sunflower, flax, safflower, coconut, palm, olive, peanut, cotton, castor bean, coriander, Crambe sp., Cuphea sp., Euphorbia sp., Oenothera sp., jojoba, Lesquerella sp., marigold, Limnanthes sp., Vernonia sp., Sinapis alba, and cocoa, with maize being most preferred. Most if not all of these plant species have been previously transformed by those skilled in the art.

In order to produce transgenic plants having altered oil compositions described herein, vectors containing chimeric genes or fragments of maize or soybean KAS II, in either the sense or antisense orientation, or ribozymes as described herein, are inserted into the plant genome. Preferably, these recombinant vectors are capable of stable integration into the plant genome and selection of transformed plant lines expressing selectable agents are expressed either by constitutive or inducible promoters in the plant cell. The chimeric genes containing maize or soybean KAS II genes or fragments, either in the sense, or antisense orientation, or genes encoding ribozymes designed against maize KAS II genes are expressed in the plant cells under the control of a constitutive, tissue-specific, developmental, or inducible promoter and the like.

Several techniques exist for introducing foreign recombinant vectors into plant cells, and for obtaining plants that stably maintain and express the introduced gene. Such techniques include acceleration of genetic material coated onto microparticles directly into cells(U.S. Pat. No. 4,945, 050 to Cornell and U.S, Pat No. 5,141,131 to DowElanco). Plants may be transformed using Agrobacterium technology, see U.S. Pat. No. 5,177,010 to University of Toledo, 5,104, 310 to Texas A&M, European Patent Application 0131624B1, European Patent Applications 120516, 159418B1 and 176,112 to Schilperoot, U.S. Pat. No. 5,149, 645, 5,469,976, 5,464,763 and 4,940,838 and 4,693,976 to Schilperoot, European Patent Applications 116718, 290799, 320500 all to Max Planck, European Patent Applications 604662, 627752 and U.S. Pat. No. 5,591,616 to Japan Tobacco, European Patent Applications 0267159, and 0292435 and U.S. Pat. No. 5,231,019 all to Ciba Geigy, U.S. Pat. Nos. 20 5,463,174 and 4,762,785 both to Calgene, and U.S. Pat. Nos. 5,004,863 and 5,159,135 both to Agracetus. Other transformation technology includes whiskers technology, see U.S. Pat. Nos. 5,302,523 and 5,464,765 both to Zeneca. Electroporation technology has also been used to transform plants, see WO 87/06614 to Boyce Thompson Institute, 5,472,869 and 5,384,253 both to Dekalb, WO9209696 and WO 09321335 both to Plant Genetic Systems. All of these transformation patents and publications are incorporated by reference.

In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during dedifferentiation using appropriate techniques described herein.

Another variable is the choice of a selectable marker. The preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialophos); imidazolinones, sulfonylureas and triazolopyrimidine herbicides, such as chlorosulfuron; bromoxynil, dalapon and the like.

In addition to a selectable marker, it may be desirous to use a reporter gene. In some instances a reporter gene may be used without a selectable marker. Reporter genes are genes which are typically not present or expressed in the recipient organism or tissue. The reporter gene typically encodes for a protein which provides for some phenotypic change or enzymatic property. Examples of such genes are provided in K. Weising et al. Ann. Rev. Genetics, 22, 421 (1988), which is incorporated herein by reference. A preferred reporter gene is the beta-glucuronidase (GUS) gene.

Regardless of transformation technique, the gene encoding said maize or soybean KAS II in either the sense or antisense orientation or ribozymes thereof is preferably incorporated into a gene transfer vector adapted to express the said gene in a plant cell by including in the vector a plant promoter regulatory element. In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see PCT/US96/1682; WO 97/13402 published Apr. 17, 1997) and the like may be used. Plant promoter regulatory elements include, but are not limited to ribulose-1,6-bisphosphate (RUBP) carboxylase small subunit (ssu), beta-conglycinin promoter, phaseolin promoter, ADH promoter, heat-shock promoters and tissue specific promoters.

Promoter regulatory elements may also contain certain enhancer sequence elements that may improve the transcription efficiency. Typical enhancers include but are not limited to Adh-intron 1 and Adh-intron 6. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active during a certain stage of the plants'development as well as active in plant tissues and organs. Examples of such include but are not limited to pollen-specific, embryo specific, corn silk specific, cotton fiber specific, root specific, seed endosperm specific promoter regulatory elements and the like. Under certain circumstances it may be desirable to use an inducible promoter regulatory element, which is responsible for expression of genes in response to a specific signal, such as: physical stimulus (heat shock genes); light (RUBP carboxylase); hormone (Em); metabolites; and stress. Other desirable transcription and translation elements that function in plants may be used. Numerous plant-specific gene transfer vectors are known to the art.

One of the issues regarding exploiting transgenic plants having altered saturate levels is the expression of multiple chimeric genes at once. European Patent Application 0400246A1 describes transformation of two Bt genes in a plant; however, these could be any two genes or fragments thereof in either the sense or antisense orientation. The options could include but are not limited to genes and fragments encoding maize or soybean KAS II with acyl-ACP thioesterase genes or genes encoding proteins such as stearoyl-ACP desaturase and the like, as well as genes to impart insect control or herbicide resistance. Another way to produce a transgenic plant having multiple traits is to produce two plants, with each plant containing the oil modifying gene of interest. These plants can then be back-crossed using traditional plant breeding techniques to produce plants wherein phenotypic characteristics are related to the presence of more than one chimeric gene.

The particular embodiments of this invention are further exemplified in the Examples. However, those skilled in the art will readily appreciate that the specific experiments detailed are only illustrative of the invention as described more fully in the claims which follow thereafter.

EXAMPLE 1

KAS II Activity Assays

Acyl carrier protein (ACP; Sigma Chemical co., St. Louis, Mo.) was dissolved [12.5 mg/mL in 25 mM $KH_2PO_4$ (pH 7.6)], chilled to 0° C., and re-purified by adding 50% (w/v) trichloroacetic acid (TCA) dropwise to 5% (v/v) final concentration. The solution was centrifuged at 10,000×g for 30 min at 4° C. and the pellet was then suspended in 20 mM Tris base (25 mL final volume). Contaminating proteins were precipitated on ice by adding 80% (w/v) ammonium sulfate for 45 min and collected by centrifugation at 23,700×g for 45 min. ACP, which remained in the supernatant, was concentrated by TCA precipitation and resolubilized with 1 mL of Tris base, supra.

Acyl-ACP synthetase was purified from *E. coli* as described by Rock and Cronan, (1979) *J. Biological Chem.*, 254:7116–7122. C16:0-ACP was synthesized for 20 h at 37° C. essentially as described by Rock et al., (1981) *Methods in Enzymology*, 72:397–403, and stored at −20° C.

Malonyl CoA-ACP transacylase, hereafter MTA, was purified from *E. coli* as described by Alberts et al. (1969) *Methods in Enzymology*, 14:50–53. Transacylase reactions were performed in 100 μL of reaction mixture [100 mM KH$_2$PO$_4$, pH 6.5, 100 μM ACP, 100 μM malonyl CoA, 10 nCi [2-$^4$C] malonyl CoA (43.1 Ci/mol), and 2 mM dithiothreitol (DTT). ACP was incubated with an equal volume of 20 mM DTT for 15 min before being added to the reaction mixture. Reactions were started by adding 10 μL of either enzyme alone or enzyme that had been incubated for 15 min with an inhibitor and allowed to proceed for 5 min at 23° C. Reactions, which were terminated by adding 400 μL of ice cold 5% (v/v) perchloric acid, were then placed on ice for 20 min before being centrifuged for 5 min at 14,000×g. Pellets were washed 3× with 5% perchloric acid before being resuspended in 500 82 L KH$_2$PO$_4$ buffer and counted using scintillation. KAS II activity was measured by modifying the method of Garwin et al. (1980) *J. Biological Chem.* 255:11949–11956. Reaction buffer contained 200 mM KH$_2$PO$_4$ (pH 6.8), 1.25 mM ethylenediaminetetraacetic acid (EDTA), 0.6 mM DTT, 10 μU MTA, 50 μM acyl carrier protein (ACP) (Sigma Chemical Co., St. Louis, Mo.), 10 μM [2-$^{14}$C] malonyl-CoA (20 Ci/mol; Amersham, Arlington Hts. Ill.), 60 μM 16:0-ACP, 5% glycerol and enzyme in a total reaction volume of 20 μL. For maximal activity, ACP (1 mM) and MTA (129 μU/mL) underwent thiol reduction in 1.25 mM EDTA, 0.6 mM DTT, and 100 mM KH2PO4, pH 6.8, for 15 min at 37° C. prior to addition to the assay. This mixture was then added to malonyl-CoA (1 μmole) and [2-$^4$C] malonyl-CoA and incubated for an additional 5 min. Palmitoyl-ACP was then added and incubated at 37° C. for 15 min. Reactions were started by adding KAS II enzyme that had been pre-incubated in KH$_2$PO$_4$, pH 7.5, 20% glycerol, 1 mM EDTA, and 0.6 mM DTT for 15 min. Reactions were stopped after 15 min by adding 400 μL of reducing agent [100 mM KH$_2$PO$_4$, 400 mM KCl, 30% tetrahydrofuran, and 5 mg/mL NaBH$_4$]. Tubes were then vortexed thoroughly and incubated for at least 30 min at 37° C. Afterwards, toluene (400 μL) was added, samples were vortexed, and centrifuged at 14,000×g for 10 sec to separate phases. The toluene layer (300 μL) was added to 5 mL Aquasol (NEN, Boston, Mass.) and incorporated [2-$^4$] malonyl CoA was determined by scintillation counting.

EXAMPLE 2

Isolation and Characterization of KAS II From Maize and Soybean Seed

Soybean and maize KAS II were purified from seed harvested 20–25 days after pollination. Typically, 200 g of seeds were harvested and stored at −70° C. until used. All steps of protein purification were done at 4° C. or on ice. Seeds were homogenized for 5 min in a Warring Blender with 300 mL of buffer A [50 mM KH$_2$PO$_4$, pH 7.5, containing 20% glycerol (v/v), 1 mM EDTA, and 2 mM DTT]. The homogenate was then centrifuged at 10,000×g for 20 min, filtered through four layers of cheesecloth, and then centrifuged at 25,000×g for 20 min. The recovered supernatant was brought to 40% (w/v) ammonium sulfate, stirred for 1 h at 4° C., and centrifuged at 25,000×g for 20 min. The resulting supernatant was then brought to 80% (w/v) ammonium sulfate, stirred for 1 h, and collected via centrifugation at 25,000×g for 20 min. The resulting pellet was dissolved in 10 mL of buffer B [20 mM KH$_2$PO$_4$, pH 7.5, with 10% glycerol (v/v), 1 mM EDTA, and 2 mM DTT] and then dialyzed. Dialyzed protein was applied to Reactive Green 19-agarose (Sigma Chemical Co.) which has been previously packed into a 2.5×16 cm column equilibrated with buffer A having 10% glycerol. KAS II activity was eluted with buffer A having 10% glycerol and 300 mM KH$_2$PO$_4$.

Fractions having synthase activity were pooled, dialyzed, and applied to a MonoQ HR 5/5 column (Pharmacia, Piscataway, N.J.). KAS II activity was eluted using a linear gradient of 0–0.5 M LiCl in buffer B over 60 min at 1 mL/min. Active fractions were then pooled, dialyzed against buffer B, and applied to a 1 mL ACP-Sepharose affinity column. The ACP-Sepharose affinity column was made by covalently attaching purified ACP to cyanogen bromide activated Sepharose CL4B beads according to manufacturer instructions (Pharmacia). After washing, enzyme activity was eluted with 5 volumes of 100 mM KH$_2$PO$_4$ (pH 7.5) containing 10% glycerol, 1 mM EDTA, and 4 mM DTT followed by a 10 volume of 250 mM KH2PO4, pH 7.5, containing 10% glycerol, 1 mM EDTA, and 4 mM DTT.

The ACP-Sepharose purified fractions were applied to a 1 mL cerulenin-Sepharose affinity column (Shimakata and Stumpf (1982) *Proc. Nat. Acad. Sci. USA*, 79:5805–5812), which was made in a manner similar to the ACP-Sepharose matrix, supra. Enzyme activity was eluted with 5 volumes of 250 mM KH$_2$PO$_4$pH 7.5, containing 10% glycerol, 1 mM EDTA, and 4 mM DTT.

Proteins from the cerulenin-Sepharose columns were analyzed by SDS-PAGE (Laemmli, 1970, *Nature* 227:680–685) on a 4–20% gel (Integrated Separation Systems, Woodburn, Mass.). Pooled fractions from the cerulenin-Sepharose column for either maize or soybean contain only a 46 kDa band silver-stained. The cerulenin-Sepharose fraction having a single band also had strong condensing activity towards C16:0-ACP, thereby indicating that the enzyme was KAS II. The $K_m$ values of maize and soybean KAS II were 14.1 μM and 18.0 μM, respectively, as determined using double reciprocal plots.

EXAMPLE 3

Isolation and Cloning of cDNAs Encoding Maize and Soybean KAS II

A cDNA clone encoding maize KAS II was obtained from a cDNA library derived from maize kernels of inbred CS608 (Mycogen Seeds, San Diego, Calif.) that had been grown in a greenhouse and hand pollinated. The cDNA library was prepared from said kernels harvested at 20 days after pollination, hereinafter 20-DAP. At 20 DAP, embryos were immediately collected, frozen on dry ice, and stored at −70° C. RNA was extracted by grinding 2.5 g to a fine powder in liquid nitrogen. Afterwards, 10 mL of extraction buffer [50 mM Tris-HCl, pH 8.0, 4% para-amino salicyclic acid (Sigma Chemical Co), 1% tri-iso-propylnaphtalenesulfonic acid (Eastman Kodak Co., Rochester, N.Y.), 10 mM DTT, and 10 mM sodium meta-bisulfite (Sigma Chemical Co.)] was then added and the mixture was homogenized for 1 min using a TEKMAR TISSUMIZER (Tekmar Co., Cincinnati, Ohio). The homogenate was extracted with an equal volume of phenol equilibrated with 0.1 M Tris-HCl, pH 8.0. Organic and aqueous phases were separated by centrifugation at 4° C. The aqueous phase was removed and extracted with an equal volume of chloroform/octanol (24:1). The supernatant was then transferred, centrifuged, transferred again, and a one-half volume of 7.5 M ammonium acetate (pH 8.0) was added. RNA was then precipitated on ice for 30 min.

Precipitated RNA was collected by centrifugation and dissolved in 1 mL of diethylpyrocarbonate-treated water (0.1% v/v), hereinafter DEPC-water. One-half volume of 7.5 M ammonium acetate (pH 8.0) and two volumes of 100% ethanol were added and the RNA was allowed to precipitate at −20° C. for 30 min. The precipitate was collected by centrifugation, washed in ice-cold 70% ethanol, air dried, and dissolved in 0.5 mL DEPC-treated water.

PolyA+mRNA was purified on oligo dT-cellulose (Collaborative Biomedical Products, Bedford, Mass.) columns. Type 3 oligo-dT cellulose (0.1 g) was equilibrated in 5 mL of buffer 1 for 30 min, where buffer 1 is loading buffer with 0.5 M NaCl and loading buffer is 20 mM Tris-HCl, pH 7.6, 1 mM EDTA, and 0.1% sodium lauryl sulfate (SDS). The column was washed with 3 volumes of DEPC-water, 3 volumes of wash buffer [0.1 N NaOH, 5 mM EDTA], 3 volumes of DEPC-water, and 5 volumes of buffer 1. The dissolved RNA pellet was heated at 65° C. for 5 min, diluted 2× with buffer 2 [2× loading buffer] and then applied to the oligo-dT column. The flow through material was then collected, reheated, and reapplied to the column. Following, the column was washed with 10 volumes of buffer 1 followed by 10 volumes of buffer 3 [loading buffer having 0.1 M NaCl]. PolyA$^+$RNA was eluted with 3 volumes of elution buffer [10 mM Tris-HCl, pH 7.5, 1 mM EDTA, 0.05% SDS] and collected in 0.5 mL fractions. RNA fractions were combined, buffered to 0.3 M sodium acetate pH 5.2, and precipitated at −20° C. for 16 h after addition of 2.2 volumes of 100% ethanol. The precipitate was collected by centrifugation, washed with 70% ethanol, dried, and dissolved in 50 μL DEPC-treated water. This material was then repurified on a fresh oligo-dT column as described herein to produce highly-enriched polyA$^+$MRNA. RNA concentrations were determined by measuring $OD_{260\ nm}$.

Five μg of polyA$^+$RNA was converted to cDNA and cloned into the LAMBDA UNI-ZAP vector using the Lambda ZAP-cDNA synthesis and cloning kit according to the manufacturers protocols (Stratagene, La Jolla, Calif.). The resulting library had an original titer of 3.38×10$^{10}$ plaque forming units/mL (pfu/mL), greater than 95% recombinants and an average insert size of 1.35 kb. The cDNA library was amplified according to Sambrook et al., (Molecular Cloning, A Laboratory Manual, 2$^{nd}$ Ed. (1989) Cold Spring Harbor Laboratory Press) and had a titer of 6.0×10$^6$ pfu/mL. Total library cDNA was batch rescued and isolated as follows: 5 mL of XL1 Blue *E. coli* cells (Stratagene) at $OD_{600\ nm}$=1.0 in 10 mM MgSO$_4$ were mixed with 8.3 μL (5×$^8$ pfu) of amplified embryo cDNA library phage-stock, and 100 μL EXASSIST helper phage (Stratagene) and incubated at 37° C. for 20 min. Twenty-five mL of TY medium [8.0 g/L tryptone, 5.0 g/L yeast extract, and 2.5 g/L NaCl, pH 7.8] was added and cells were incubated at 37° C. for 3 h while shaking. Afterwards, the bacterial cells were heat killed at 68° C. for 15 min and the supernatant was recovered. Five hundred μL supernatant was mixed with 14.5 mL of SOLR cells (Stratagene) (OD$_{600\ nm}$=1.5), incubated at 37° C. for 15 min, added to 500 mL LB [10 g/L tryptone, 10 g/L NaCl, and 5 g/L yeast extract containing 50 μg/mL Ampicillin], and grown overnight. Afterwards, plasmid DNA was obtained by alkaline lysis/CsCl purification, according to Sambrook et al (Molecular Cloning, A Laboratory Manual, 2$^{nd}$ Ed. (1989) Cold Spring Harbor Laboratory Press) and analyzed by agarose gel electrophoresis following digestion with EcoRI/XhoI. A smear ranging from 0.5 to 3.0 kb was observed following electrophoresis.

To isolate a clone encoding maize KAS II, a DNA fragment was amplified using polymerase chain reaction technology, hereinafter PCR, to produce a probe which could be used to isolate a full length cDNA. A 5' primer with 256-fold degeneracy and a 3' primer with 256-fold degeneracy, entered herein as SEQ ID NO:1 and SEQ ID NO:2, respectively, were synthesized on an Applied Biosystems High-Throughput DNA Synthesizer Model 394 (Foster City, Calif.). Double stranded cDNA was used as template. PCR amplification was performed as follows: 10 ng template DNA, 5 μL 10× reaction buffer, hereinafter 10×RB, [100 mM Tris-HCl pH 8.3, 500 mM KCl, 15 mM MgCl$_2$, 0.01% (w/v) gelatin], 5 μL of 2 mM deoxyribose nucleotides triphosphate (dNTPs), 50 pmole primers (SEQ ID NO:1 and SEQ ID NO:2), 2.5 units AMPLITAQ DNA Polymerase (Perkin-Elmer, Norwalk, Conn.) and water for a total volume of 50 μL. A DNA Thermal Cycler (Perkin-Elmer Cetus Model #9600, Norwalk, Conn.) was programmed as follows: 96° C. for 1 min; [94° C. (1 min), 55° C. (2 min), and 72° C. (3 min)] for 35 cycles; followed by 7 min at 72° C. A DNA product of 527 base pairs (bp) was obtained, sequenced as described infra, and entered herein as SEQ ID NO:3.

The PCR fragment was cloned directly into the PCR®2.1 vector (Invitrogen, Carlsbad, Calif.) and transformed into One Shot™ INVαF' competent cells (Invitrogen) according to manufacturers specifications. The DNA was extracted using the Qiawell Plasmid Purification System (Qiagen, Santa Clarita, Calif.) according to the manufacturers instructions. Recombinant clones were sequenced by dideoxy chain termination using PRISM AMPLITAQ READY REACTION DYEDEOXY Terminator cycle sequencing kit #401384 according to the manufacturer (Perkin-Elmer Applied Biosystems Division, Foster City, Calif.). Samples were run on an ABI373A automated DNA sequencer (Perkin-Elmer, Applied Biosystems Division). DNA sequence analysis of SEQ ID NO:3 was performed using MACVECTOR v. 4.1.4 (Oxford Molecular, Campbell, Ky.), which gave theoretical translations and alignments thus generating the amino acid sequence entered herein as SEQ ID NO:4.

The CS608 embryo cDNA library described herein was screened using a DNA fragment which was essentially SEQ ID NO:3 with the addition of the DNA nucleotides AAT-TCGGCTT at the 5' end and AAGCCG at the 3' end of said sequence. These extra bases were derived from the TA vector. This fragment (543 bp) was used to obtain full length,clones encoding maize KAS II. Probe DNA was obtained by digesting the TA cloned PCR fragment with EcoR1. This material was then run on a preparative 1% agarose gel, the 543 bp band was excised and the DNA was extracted with QIAEX (Qiagen). An $\alpha^{32}$P-deoxyribocytosine triphosphate (dCTP)-labeled probe was generated using HIGHPRIME Random Labeling kit (Boehringer Mannheim, Indianapolis, Ind.) according to the manufacturer instructions using 5 μL of [$\alpha^{32}$P]-dCTP (3000 Ci/mmole, 10 μCi/μL, DuPont, NEN Life Science Products, Boston, Mass.). Afterwards, the labeling reaction was applied to a NICK column (Pharmacia) equilibrated with TE [10 mM Tris-HCl, pH 8.0, 1 mM EDTA]. Labeled DNA was eluted with 2 volumes of TE (400 μL each). The probe was heat denatured before being added to hybridization buffer as described herein.

Methods for phage titering, plating, coring and rescuing were as described in the LAMBDA ZAP II Library (Stratagene) instruction manual. The cDNA library was plated (85,000 pfu/plate) on two 24.3×24.3 cm NUNC assay plates (Nunc Inc. Roskilde, Denmark). Duplicate phage lifts were taken from each plate using 0.45 Am MAGNAGRAPH-NT nylon membrane (MSI, Westborough, Mass.). Filters were treated as follows: 5 min with 0.5 N NaOH/1.5 M NaCl, pH 12.8; 5 min air dry; 5 min with 0.5 M Tris, (pH 7.6)/1.5 M NaCl; and 5 min air dry. DNA was cross-linked to the membranes while on filter paper dampened with 2×SSC [1×SSC is 0.15 M NaCl, 0.015 M sodium citrate, pH 7.0] using a STRATALINKER UV Crosslinker (Stratagene).

Filter prehybridization was performed at 42° C. in 150 mL hybridization buffer containing 50% (v/v) formamide, 6×SSC, 10× Denhardt's solution [1× Denhardt's solution is 0.02% Ficoll (Type 400, Pharmacia), 0.02% polyvinylpyrollidone, and 0.02% bovine serum albumin], 0.1% (w/v) SDS, and 200 μg/mL sheared and denatured salmon sperm DNA. After 3 h, used hybridization buffer was replaced with 100 mL of fresh hybridization buffer containing labeled probe (specific activity=5×10$^8$dpm/Ag). Hybridization continued for 18–20 h at 42° C. with gentle rotation. Afterwards, filters were washed twice at 55–60° C. for 40 min in 1 L of wash solution containing 0.2×SSC and 0.1% SDS. Filters were then exposed to Kodak XOMAT-AR Film (Eastman Kodak Company, Rochester, N.Y.) with intensifying screens (Lightening Plus, DuPont CRONEX, DuPont, Wilmington Del.) for 16 h at −70° C. Examination of films allowed the identification of positive plaques.

Positive plaques were cored out and stored in 1 mL SM buffer [5.8 g/L NaCl, 2 g/L MgSO$_4$, 20 mM Tris-HCl, pH 7.5, 5 mL/L of 2% (w/v) gelatin] with 50 μL chloroform. Phage were plated for secondary screening using 50 μL of a 1:1000 dilution of the primary phage stock. Positive plaques from the secondary screening were cored out and stored in 500 μL of SM buffer. Phage from these stocks were then plated for tertiary screenings using amounts ranging from 5 μL of undiluted secondary stock to 20 μL of 1:100 dilution in SM buffer. All subsequent hybridizations were performed as described, supra. Isolates were rescued into phagemid form per the LAMBDA-ZAP II Library Instruction Manual (Stratagene). Rescued phagemid were plated by combining 200 μL SOLR cells (Stratagene) grown to OD$_{600nm}$=0.5 to 1.0 with 50–100 μL phagemid and incubating for 15 min at 37° C. Cells containing phagemid were streaked on LB agar containing Ampicillin (75 μg/mL) and grown overnight at 37° C. DNA was extracted from 4 mL liquid cultures grown overnight at 37° C. in TB [1.2% tryptone, 2.4% yeast extract, 0.4% glycerol, 0.17 M KH$_2$PO$_4$, and 0.72 M K$_2$HPO$_4$] using the alkaline lysis/polyethylene glycol protocol described in the PRISM READY REACTION DYEDEOXY Terminator Cycle Sequencing Kit Protocol#401388 Rev. B (Perkin-Elmer, Applied Biosystems Division). A sequence of the full length maize KAS II cDNA and corresponding amino acid sequence is entered herein as SEQ ID NO:5 and SEQ ID NO:6, respectively. The DNA sequence encoding the precursor protein is entered herein as SEQ ID NO:7. The DNA and amino acid sequence for the mature protein are entered herein as SEQ ID NO:8 and SEQ ID NO:9, respectively.

EXAMPLE 4

Isolation of a Soybean KAS II Probe

A soybean KAS II probe was isolated by PCR amplification using conditions described herein, supra. A 5' primer with 128-fold degeneracy and a 3' primer with 1024-fold degeneracy, entered herein as SEQ ID NO:10 and SEQ ID NO:11, respectively, were used. Template DNA used for the amplification was batch rescued soybean cDNA library DNA using the methods described herein, supra (Stratagene, La Jolla, Calif.). The resulting 596 bp fragment, entered herein as SEQ ID NO: 12, was sequenced directly. Sequencing was performed as described herein and the deduced amino acid translation is entered herein as SEQ ID NO:13.

A commercially available soybean epicotyl cDNA library (Stratagene) was probed with the 596 bp DNA soybean KAS II fragment, SEQ ID NO:12, to isolate full length cDNAs encoding soybean KAS II. Probe DNA was prepared and used to screen the phage library as described previously, supra. Two cDNAs were identified and the DNA and amino acid sequence are entered herein for the first cDNA as SEQ ID NO:14 and SEQ ID NO:15, respectively. The precursor DNA for the first soybean KAS II clone is entered herein as SEQ ID NO:16 and the mature DNA and amino acid sequences are entered herein as SEQ ID NO:17 and SEQ ID NO:18, respectively. The DNA and amino acid sequence entered herein for the second soybean KAS II clone is SEQ ID NO:19 and SEQ ID NO:20, respectively. The precursor DNA for the second soybean KAS II clone is entered herein as SEQ ID NO:21 and the mature DNA and amino acid sequences are entered herein as SEQ ID NO:22 and SEQ ID NO:23, respectively.

EXAMPLE 5

Expression, Purification, and Analysis of *E. coli* Produced Maize and Soybean KAS II Vectors based on the pET26b expression vector (Novagen, Madison, Wis.) were constructed for the expression of KAS II protein in *E. coli* under the control of T7 promoter transcription and translation signals. KAS II DNA fragments containing 5' Nde I and 3' Xho I or Sac I sites were generated by PCR amplifications and ligated into the 5' Nde I and 3' Xho I or Sac I restriction sites of pET 26b in frame with the ATG start codon for methionine encoded by the plasmid. 5' and 3' primers for amplification of the mature maize KAS II fragment were according to SEQ ID NO:24 and SEQ ID NO:25, respectively. 5' and 3' primers for amplification of the first mature soybean KAS II fragment were according to SEQ ID NO:26 and SEQ ID NO:27, respectively. 5' and 3' primers for amplification of the second mature soybean KAS II fragment were according to SEQ ID NO:26 and SEQ ID NO:28, respectively. The KAS II fragments were generated using PCR amplification reactions containing the following components: 100 ng phagemid cDNA (SEQ ID NO:5 for maize KAS II; SEQ ID NO:14 for the first soybean KAS II clone; SEQ ID NO:19 for the second soybean KAS II clone), 10 μl of 10× RB, 10 μl 2 mM nucleotide mixture, 100–200 pmoles of each primer set, and 5 units of AmpliTaq™ polymerase (Perkin Elmer/ABI, Foster City, Calif.). Amplifications were performed using the GENEAMP PCR system 9600 (Perkin-Elmer) programmed with the following thermal profile: 96° C. (1 min); [94° C. (30 sec), 60° C. (30 sec), and 72° C. (45 sec)] for seventeen cycles; followed by 7 min at 72° C. The resulting amplification products were essentially SEQ ID NO:8, SEQ ID NO:17, and SEQ ID NO:22 with the following modifications: SEQ ID NO:8 had the nucleotides CAT and CTCGAG at the 5' and 3' ends, respectively; SEQ ID NO:17 had the nucleotides ACGTACGTCA AND GAGCTCACGT ACGT at the 5' and 3' ends, respectively; and SEQ ID NO:22 had the nucleotides ACGTACGTCAT and GAGCTCACG-TACGT at the 5' and 3' ends, respectively. The PCR fragments were cloned directly into the pCR®2.1 vector (Invitrogen, Carlsbad, Calif.) and transformed into One Shot™INVαF' competent cells (Invitrogen) according to manufacturers specifications. 3 mL cultures were grown up overnight in TE [1.2% tryptone, 2.4% yeast extract, 0.4% glycerol, 0.17 M KH$_2$PO$_4$, and 0.72 M K$_2$HPO$_4$] and DNA was extracted using a mini-prep protocol described by Sambrook et al (Molecular Cloning, A Laboratory Manual, 2$^{nd}$ Ed. (1989) Cold Spring Harbor Laboratory Press). Extracted DNA was digested with EcoRl and run on analytical agarose gels to detect the presence of the appropriately sized insert. Preparative digests of the desired isolates were performed with Nde I and Xho I or Nde I and Sac I. DNA was run on preparative agarose gels and the Nde I/Xho I or Nde I/Sac I fragments were extracted from the agarose gel using Qiaex® (Qiagen) and ligated into pET 26b vectors digested with Nde/Xho I or Nde/Sac I using the Rapid DNA Ligation Kit (Boehringer Mannheim). The resulting vectors were named pDAB388 (pET26+maize KAS II (SEQ ID NO:8)), pDAB393 (pET26b+first soybean KAS II (SEQ ID NO:17)), pDAB394 (pET 26b+second soybean KAS II (SEQ ID NO:22)).

For expression, BL21/pLys-S E. coli cells (Novagen, Madison, Wis.) were transformed with plasmid pDAB388, pDAB393 or pDAB394 and transformants were selected on LB agar plates containing 30 μg/mL kanamycin and 35 μg/mL chloramphenicol. After growing overnight at 37° C., cells were scraped and placed into 25 mL LB broth containing 30 μg/mL kanamycin and 35 μg/mL chloramphenicol and allowed to grow to $OD_{600nm}$=0.6. Isopropyl-beta-D-thiogalactopyranoside, hereinafter IPTG, was added to a final concentration of 1 mM, and cells were incubated at 37° C. with shaking for 2.5 to 5 h. Cells were then pelleted at 2000×g and frozen on dry ice, thawed for 5 min at 37° C., frozen, and thawed again. Afterwards, the cells were resuspended in 0.5 mL E. coli lysis buffer [10 mM Tris-HCl, pH 8.0; 150 mM NaCl, 1 mM EDTA, 0.1% (v/v) Triton X-100] containing freshly added DNase and RNase (50 μg/mL each). Cells were held at 37° C. for 30 min followed by centrifugation at 15,000×g for 15 min at 4° C. Resulting supernatants were stored at −20° C.

EXAMPLE 6

Enzymatic Analysis of Heterologously Expressed KAS II

For enzymatic analysis of E coli expressed soybean and maize KAS II, substrates were made as follows: ACP (Sigma Chemical Co.) was further purified by three cycles of precipitation at pH 4.0 using 10% (v/v) acetic acid followed by resolubilization in 50 mM Tris-HCl, pH 8.0. Decanoic acid, 10:0 and palmitic acid, 16:0 were obtained from Sigma. Acyl-ACPs were synthesized and purified as described previously, supra. Synthase assays were conducted as described herein. Synthase activity was measured by synthase-catalyzed condensation of [$2^{14}C$] malonyl-CoA with either C10:0-ACP or C16:0-ACP. In some cases, cerulenin, which completely inhibits KAS I activity at concentrations of 5 μM or greater, was used. Addition of cerulenin to levels of 50 μM results in about 50% inhibition of KAS II. Incorporated malonyl-CoA was extracted into toluene prior to quantitating by liquid scintillation counting. Protein concentrations were determined according to Bradford ((1976) Anal. Biochem. 189:248–254). Linear regressions were used for determination of kinetic constants from double reciprocal plots.

The substrate specificity of partially purified maize and both soybean KAS II proteins expressed in E. coli was determined as shown in Table 1. Expressed maize and soybean KAS II had the highest level of activity towards 16:0-ACP when compared to 10:0-ACP.

TABLE 1

Substrate specificity of partially purified maize and soybean KAS II expressed in E. coli.

| Source | C10:0-ACP[a] | C16:0-ACP | 50 μM Cerulenin | |
|---|---|---|---|---|
| | | | C10:0-ACP | C16:0-ACP |
| pET26 | 675 ± 109 | 788 ± 159 | 49.7 ± 5 | 476 ± 22 |
| pDAB388 | 734 ± 41 | 909 ± 53 | 14 ± 1 | 433 ± 13 |
| pDAB393 | 870 ± 7 | 2396 ± 62 | 116 ± 67 | 1320 ± 25 |
| pDAB394 | 890 ± 9 | 2162 ± 96 | 43 ± 12 | 1249 ± 116 |

[a]Numbers listed are counts per minute of radio-labeled [$2^{-14}C$]malonyl-CoA condensation of either C10:0-ACP to C12:0-ACP or C16:0-ACP to C18:0-ACP per minute.

EXAMPLE 7

Construction of Maize Transformation Vectors

Two maize expression vectors containing the globulin seed specific promoter driving soybean KAS II were constructed. The first plasmid, pDAB395, encodes only the globulin promoter driving the first soybean KAS II gene (SEQ ID NO:16) and was co-bombarded with plasmid pDAB308 which carried the BAR selectable marker gene. The second plasmid, pDAB397, carries both the globulin promoter driving the soybean KAS II gene and the BAR selectable marker gene eliminating the need for co-transformation.

Plasmid pDAB395 is a 5564 bp plasmid containing the following components: nucleotides 1 to 12 correspond to bases 1–12 of pUC18 if nucleotide 1 of pUC18 is defined as the G residue of the restriction site EcoR1 and moving in a clockwise direction toward the sense strand coding for ampicillin resistance (Messing, J. et al (1983) Gene 26: 101–106); nucleotides 13 to 1263 are the globulin promoter corresponding to bases 5 to 1255 of SEQ ID NO:29; nucleotides 1264 to 2733 encode the first soybean KAS II cDNA corresponding to SEQ ID NO:16; bases 2734 to 2739 are an Xho I site; nucleotides 2756 to 3008 are the NOS untranslated 3' region (DePicker et. al., (1982) J. Molec. Appl. Genet. 1:561–573); nucleotides 3020 to 3423 correspond to bases 1–404 of pUC18; and nucleotides 3434 to 5664 correspond to nucleotides 405–2635 of pUC18.

Plasmid pDAB395 was co-bombarded with the plasmid pDAB308 which contains a selectable marker gene. Plasmid pDAB308 is a 4496 base pair plasmid having the following sequence: position 1 corresponds to base 441 of pUC19 (Messing, J. (1983) in "Methods in Enzymology" (Wu, R. et al., Eds) 101:20–78) and is the base after the final C residue of the SphI site. Reading on the strand contiguous to the LacZ gene coding strand, which corresponds to nucleotides 4468 to 4496 and 1851 to 2105 of plasmid of pDAB308. Nucleotides 20 to 271 of plasmid pDAB308 correspond 7093 to 7344 of the Cauliflower Mosaic Virus CabbS strain, hereinafter CaMV, (Franck, et al., (1980) Cell 21:285–294); nucleotides 280 to 626 of plasmid pDAB308 correspond to nucleotides 7093 to 7439 of CaMV; nucleotides 647 to 666 of plasmid pDAB308 correspond to nucleotides 167 to 186 of Maize Streak Virus, hereinafter MSV, (Mullineaux, et al., (1984) EMBO J. 3:3063–3068); nucleotides 667 to 756 of plasmid pDAB308 correspond to nucleotides 188 to 277 of MSV; nucleotides 757 to 849 of plasmid pDAB308 correspond to bases CA followed by nucleotides 120 to 210 of maize alcohol dehydrogenase 1S, hereinafter Adh1, (Dennis, et al.,(1984) Nucl. Acids Res. 12:3983–4000) containing parts of exon 1 and intron 1; nucleotides 850 to 967 of plasmid pDAB308 correspond to nucleotides 555 to 672 of Adh1 containing parts of intron 1 and exon 2; nucleotides 978 to 1017 of plasmid pDAB308 correspond to nucleotides 278 to 317 of MSV; nucleotides 1018 to 1566 of plasmid pDAB308 correspond to a modified BAR coding region from pIJ4104 (White et al., (1990) Nucl. Acids. Res. 18:1062) having the AGC (serine) codon in the second position replaced by GCC (alanine) and nucleotide 546 changed from G to A; nucleotides 1591 to 1847 of plasmid pDAB308 correspond to nucleotides 1298 to 1554 of nopaline synthase (DePicker, et al.,(1982) J. Molec. Appl. Genet. 1:561–573); and nucleotides 1848 to 4496 of plasmid pDAB308 correspond to the base G followed by the rest of pUC 19.

Plasmid pDAB397 is a 7746 bp plasmid consisting of the following sequences: nucleotides 1 to 2252 of pDAB397 correspond to the reverse complement of nucleotides 435 to 2686 of pUC19. Nucleotides 2280 to 3522 of pDAB397 are the maize globulin promoter amplified from proprietary inbred CS406. Nucleotides 3523 to 4993 of pDAB397 correspond to SEQ ID NO:16 Bases 5015–5282 of pDAB397 corresponds to nucleotides 4420 to 4687 of plasmid pBI101 (Clontech, Palo Alto, Calif.). Nucleotides 5285 to 5449 of pDAB397 are the reverse complement of nucleotides 238–402 of pUC19. Nucleotides 5514 to 6122 of pDAB397 comprise the double enhanced 35S promoter, with nucleotides 5776 to 6122 corresponding to nucleotides 7093 to 7439 of the Cauliflower Mosaic Virus genome (Franck et al., (1980) Cell 21:285–294). Nucleotides 5514 to 5767 of pDAB397 are a duplication of nucleotides 5774 to 6027. Nucleotides 6143 to 6253 of pDAB397 correspond to nucleotides 167 to 277 of the Maize Streak Virus genome (Mullineaux et al., (1984) EMBO J. 3:3063–3068). Nucleotides 6254 to 6470 of pDAB397 correspond to the modified first intron of the maize alcohol dehydrogenase gene (Adhl-S) (Dennis et al., (1984) Nucleic Acids Res. 12:3983–4000). The modification resulted in removal of 343 nucleotides (bases 1313 to 1656) with bases 1222 to 1312 (intron 5' end) and nucleotides 1657 to 1775 (intron 3' end) of the maize Adhi-S gene remaining. Nucleotides 6471 to 6505 of pDAB397 correspond to Maize Streak Virus (MSV) nucleotides 278 to 312. Both sections of the Maize Streak Virus, hereinafter MSV, sequence comprise the untranslated leader of the MSV coat protein V2 gene, and are interrupted in plasmid pDAB397 by the modified Adh1 intron. Nucleotides 6509 to 7065 of plasmid pDAB397 corresponds to nucleotides 29 to 585 of the phosphinotricin acetyl transferase (BAR) gene of Streptomyces hygroscopicus (White et al., (1989) Nucleic Acids Res. 18:1062). To facilitate cloning, nucleotides 34 and 575 of the published sequence were changed from A to G and G to A, respectively. This sequence serves as the selectable marker in plant cells. Nucleotides 7071 to 7324 of pDA2397 correspond to nucleotides 4420 to 4683 of plasmid pBI101 (Clontech, Palo Alto, Calif.). Nucleotides 7342 to 7345 of pDAB397 comprise the linker TCGG. The remaining sequence of pDAB397 (nucleotides 7346 to 7746) correspond to nucleotides 284 to 684 of pUC19.

EXAMPLE 8

Production and Regeneration of Transgenic KASII Maize Isolates

Type II callus cultures were initiated from immature zygotic embryos of the genotype "Hi-II." (Armstrong et al, (1991) Maize Cooperation Newsletter, pp.92–93). Embryos were isolated from greenhouse-grown ears from crosses between Hi-II parent A and Hi-II parent B or F2 embryos derived from a self- or sib-pollination of a Hi-II plant. Immature embryos (1.5 to 3.5 mm) were cultured on initiation medium consisting of N6 salts and vitamins (Chu et al, (1978) *The N6 medium and its application to anther culture of cereal crops*. Proc. Symp. Plant Tissue Culture, Peking Press, 43–56) 1.0 mg/L 2,4-D, 25 mM L-proline, 100 mg/L casein hydrolysate, 10 mg/L AgNO$_3$, 2.5 g/L GELRITE, and 20 g/L sucrose, with a pH of 5.8. Selection for Type II callus took place for ca. 2–12 weeks. After four to six weeks callus was subcultured onto maintenance medium (initiation medium in which AgNO$_3$ was omitted and L-proline was reduced to 6 mM).

The plasmids pDAB397 and pDAB395/pDAB308 were transformed into embryogenic callus. For blasting 140 μg of plasmid DNA was precipitated onto 60 mg of alcohol-rinsed, spherical gold particles (1.5–3.0 Mm diameter) by adding 74 μL of 2.5M CaCl$_2$H$_2$O and 30 μL of 0.1M spermidine (free base) to 300 μL of plasmid DNA and H$_2$O. The solution was immediately vortexed and the DNA-coated gold particles were allowed to settle. The resulting clear supernatant was removed and the gold particles were resuspended in 1 ml of absolute ethanol. This suspension was diluted with absolute ethanol to obtain 15 mg DNA-coated gold/mL.

Approximately 600 mg of embryogenic callus tissue was spread over the surface of Type II callus maintenance medium as described herein lacking casein hydrolysate and L-proline, but supplemented with 0.2 M sorbitol and 0.2 M mannitol as an osmoticum. Following a 4 h pre-treatment, tissue was transferred to culture dishes containing blasting medium (osmotic media solidified with 20 g/L tissue culture agar (JRH Biosciences, Lenexa, Kans.) instead of 7 g/L GELRITE (Schweizerhall, South Plainfield, N.J.). Helium blasting accelerated suspended DNA-coated gold particles towards and into the prepared tissue targets. The device used was an earlier prototype of that described in U.S. Pat. No. 5,141,131 which is incorporated herein by reference. Tissues were covered with a stainless steel screen (104 μm openings) and placed under a partial vacuum of 25 inches of Hg in the device chamber. The DNA-coated gold particles were further diluted 1:1 with absolute ethanol prior to blasting and were accelerated at the callus targets four times using a helium pressure of 1500 psi, with each blast delivering 20 μL of the DNA/gold suspension. Immediately post-blasting, the tissue was transferred to osmotic media for a 16–24 h recovery period. Afterwards, the tissue was divided into small pieces and transferred to selection medium (maintenance medium lacking casein hydrolysate and L-proline but having 30 mg/L BASTA (Agrevo)). Every four weeks for 3 months, tissue pieces were non-selectively transferred to fresh selection medium. After 11 weeks and up to 18 weeks, callus sectors found proliferating against a background of growth-inhibited tissue were removed and isolated. The resulting BASTA-resistant tissue was subcultured biweekly onto fresh selection medium. Following gas chromatography/fatty acid methyl ester, hereinafter GC/FAME, analyses, as described herein, positive transgenic lines were identified and transferred to regeneration media.

Regeneration was initiated by transferring callus tissue to cytokinin-based induction medium, which consisted of Murashige and Skoog salts, hereinafter MS salts, and vitamins (Murashige and Skoog, (1962) Physiol. Plant. 15: 473–497) 30 g/L sucrose, 100 mg/L myo-inositol, 30 g/L mannitol, 5 mg/L 6-benzylaminopurine, hereinafter BAP, 0.025 mg/L 2,4-D, 30 mg/L BASTA, and 2.5 g/L GELRITE (Schweizerhall) at pH 5.7. The cultures were placed in low light (125 ft-candles) for one week followed by one week in high light (325 ft-candles). Following a two week induction period, tissue was non-selectively transferred to hormone-free regeneration medium, which was identical to the induction medium except that it lacked 2,4-D and BAP, and was kept in high light. Small (1.5–3 cm) plantlets were removed and placed in 150×25 mm culture tubes containing SH medium (SH salts and vitamins (Schenk and Hildebrandt, (1972) Can. J. Dot. 50:199–204), 10 g/L sucrose, 100 mg/L myo-inositol, 5 mL/L FeEDTA, and 2.5 g/L GELRITE (Schweizerhall), pH 5.8). Plantlets were transferred to 10 cm pots containing approximately 0.1 kg of METRO-MIX 360 (The Scotts Co. Marysville, Ohio) in the greenhouse as soon as they exhibited growth and developed a sufficient root system. They were grown with a 16 h photoperiod supplemented by a combination of high pressure sodium and metal halide lamps, and were watered as needed with a combination of three independent Peters Excel fertilizer formulations (Grace-Sierra Horticultural Products Company, Milpitas, Calif.). At the 3–5 leaf Stage, plants were transferred to five gallon pots containing approximately 4 kg METRO-MIX 360.

Primary regenerants were self- or sib-pollinated, or outcrossed to either elite inbreds or transgenic plants after an additional 6–10 weeks in the 5 gallon pots. $R_1$ seed is being collected at 40–45 days post-pollination.

EXAMPLE 8

Gas Chromatography-Fatty Acid Methyl Ester Analysis (GC/FAME) of Maize Tissues

The procedure for extraction and esterification of fatty acids from plant tissue was a modification of Browse et. al. ((1986) *Anal. Biochem.* 152:141–145). One to 20 mg of plant tissue was placed in a test tube. After addition of 1 mL of methanolic-HCL (Supelco, Bellefonte, Pa.), the tubes were purged with nitrogen gas and sealed. Tubes were then heated at 80° C. for 1 h and allowed to cool. Fatty acid methyl esters were removed from the reaction mixture by extraction with hexane, which involved adding 1 mL of hexane and 1 mL of 0.9% (w/v) NaCl followed by vigorous shaking. After centrifugation at 16,000×g for 5 min the top hexane layer was removed and used for FAME analysis.

Analysis was performed by injection of 1 µL of sample on a Hewlett-Packard (Wilmington, Del.) Series II model 5890 gas chromatograph equipped with a flame ionization detector and a J&W Scientific (Folsom, Calif.) DB-23 column. The oven temperature was maintained at 150° C. throughout the run (20 min) and the flow of the carrier gas (helium) was 80 cm/sec. Conditions allowed separation of the five fatty acid methyl esters of interest having varying carbon lengths: 16:0, palmityl methyl ester; 18:0, stearyl methyl ester; 18:1, oleoyl methyl ester; 18:2, linoleoyl methyl ester; and 18:3, linolenyl methyl ester. Data collection and analysis was performed with a Hewlett-Packard Series II Model 3396 integrator and a PE Nelson (Perkin-Elmer) data collection system. The percentage of each fatty acid methyl ester in the sample was taken directly as indicated by the data collection system. Quantitative amounts of each fatty acid methyl ester were calculated using peak areas of a standard (Matreya, Pleasant Gap, Pa.) having known amounts of the five fatty acid methyl esters of interest. The amount determined was used to estimate the percentage of each fatty acid per total fresh weight. Adjustments were not made for loss of fatty acids during the extraction and esterification procedure since recoveries typically ranged from 90 to 100% depending on the original amount of the sample. The presence of plant tissue in the extraction mixture had no effect on the recovery of known quantities of standard.

EXAMPLE 9

Method For Production of Maize Somatic Embryos and Analysis of Fatty Acids Therein Embryogenic callus material containing the genes of interest was maintained as described herein. Continuous production of somatic embryos, which make up a large portion of embryogenic callus, was performed by transferring the callus tissue every two weeks. While the somatic embryos continued to proliferate, they usually remained in an early stage of embryo development because of the continued presence of 2,4-D in the culture medium. Somatic embryos could be regenerated into plantlets when callus was subjected to the regeneration procedure described herein. During regeneration, somatic embryos formed roots and a shoot, subsequently ceasing development as an embryo.

Somatic embryos were made to develop as seed embryos by growing embryogenic callus on MS medium containing 6% (w/v) sucrose. The callus was grown for 7 days and then somatic embryos were individually transferred to MS medium with 6% sucrose and 10 µM abscisic acid, hereinafter ABA.

Somatic embryos were assayed for fatty acid composition using GC/FAME 3 to 7 days after growth on MS medium containing 6% sucrose and 10 µM ABA. Their fatty acid composition was compared to the fatty acid composition of embryogenic callus and to maize zygotic embryos 12 DAP (Table 2). Fatty acid composition of embryogenic callus differed from that of somatic embryos in that the callus had higher percentages of 16:0 and 18:3 while having lower percentages of 18:1 and 18:2. In addition, the percentage of lipid by fresh weight for the embryogenic callus was 0.4% compared to the somatic embryos 4.0%. The fatty acid composition of the zygotic embryos and somatic embryos were very similar and their percentage of lipid by fresh weight were nearly identical. These data validated the use of the somatic embryo culture system as an in vitro system for testing the effect of certain genes on lipid synthesis in developing embryos of maize.

TABLE 2

A comparison of the fatty acid composition of embryogenic callus, somatic embryos and zygotic embryos.

| | Percent Fatty Acid Composition | | |
|---|---|---|---|
| Fatty Acid Methyl Ester | Embryogenic Callus[a] | Somatic Embryo[a,b] | Zygotic Embryo[a,c] |
| 16:0 | 19.4 ± 0.9 | 12.6 ± 0.7 | 14.5 ± 0.4 |
| 18:0 | 1.1 ± 0.1 | 1.6 ± 0.8 | 1.1 ± 0.1 |
| 18:1 | 6.2 ± 2.0 | 18.2 ± 4.9 | 18.5 ± 1.0 |
| 18:2 | 55.7 ± 3.1 | 60.7 ± 5.1 | 60.2 ± 1.5 |
| 18:3 | 8.8 ± 2.0 | 1.9 ± 0.3 | 1.4 ± 0.2 |

[a]The percentage of lipid by fresh weight of tissue was 0.4 ± 0.1, 4.0 ± 1.1, and 3.9 ± 0.6 for embryogenic callus, somatic embryo, and zygotic embryo, respectively.
[b]Somatic embryos were grown on MS medium containing 6% sucrose and 10 mM ABA.
[c]Zygotic embryo were tested 12 DAP.

Somatic embryos transformed with pDAB395 were produced from embryogenic callus using the methods described herein. Control somatic embryos were produced from untransformed lines having backgrounds identical to that of the transformed lines. The 16:0 content of the control somatic embryos averaged ca. 13%. A reduction in 16:0 was evident in 11 of the 31 transgenic lines tested. The average reduction in 16:0 ranged from 23 to 55%. Table 3 shows the total fatty acid composition of somatic embryos produced from lines 395-18 and 395-27, in which the average reduction in 16:0 content compared to control somatic embryos, was 43% and 34% respectively.

TABLE 3

Fatty acid composition of somatic embryos produced from transgenic cultures containing KAS II (pDAB395).

| Culture Line | Average Fatty Acid Content (Percent of Total Fatty Acids ± SE) | | | | | Total Fatty Acid Content (% of fresh weight) |
|---|---|---|---|---|---|---|
| | 16:0 | 18:0 | 18:1 | 18:2 | 18:3 | |
| 395-18 | 7.9 (±1.9) | 1.1 (±0.4) | 16.4 (±2.8) | 71.5 (±3.4) | 1.8 (±0.5) | 2.5 (±1.1) |
| control | 13.9 (±1.1) | 1.7 (±0.5) | 21.2 (±4.8) | 60.5 (±5.2) | 1.5 (±0.3) | 4.4 (±1.5) |
| 395-27 | 8.2 (±1.4) | 1.3 (±0.2) | 19.6 (±2.4) | 69.0 (±2.7) | 1.5 (±0.3) | 5.0 (±0.7) |
| control | 12.4 (±0.6) | 1.2 (±0.3) | 19.0 (±4.0) | 65.2 (±4.7) | 1.5 (±0.2) | 5.1 (±1.5) |

Embryogenic callus from lines 395-18 and 395-27 was used to regenerate plants as described herein. Pollinations were made, seed were obtained as described herein, and fatty acid methyl ester analysis was performed on a small portion (0.5 to 1.5 mg) of each seed embryo. A comparison of the fatty acid composition of seed which showed the reduced 16:0 phenotype from these two lines is shown in Table 4. All of the lines described above showing reduced 16:0 levels contained at least one intact copy of the gene of interest, as determined by Southern analysis. Those seed showing reduced 16:0 in lines 395-18 and 395-27 had levels that were ca. 53% and 36%, respectively, lower than that seen for the controls. Seed having lowered levels of 16:0 had concomitant small increases in 18:0 content. The average total saturated fatty acid percentage for lines 395-18 and 395-27 was 7.7% and 9.2%, respectively. The seed with the lowest level of 16:0 had the following fatty acid profile: 4.1% of 16:0; 2.8% of 18:0; 23.9% of 18:1; 67.1% of 18:2 and 0.6% of 18:3, with total fatty acid content of 32.1 percent fresh weight. The seed with the lowest percentage of total saturated fatty acids had the following fatty acid profile: 4.2% of 16:0; 2.1% of 18:0; 19.6% of 18:1; 73.5% of 18:2 and 0.6% of 18:3, with total fatty acid content of 13.5 percent fresh weight. The data described herein demonstrate that a reduction in the levels of saturated fatty acids, particularly palmitate (16:0), in somatic embryos and seeds of maize, can be obtained by transformation with a gene construct composed of a KAS II gene in a sense orientation relative to a seed-specific promoter.

TABLE 4

The fatty acid composition of seed embryos from 395-18 and 395-27.

| Embryos From Plant Line: | Average Fatty Acid Content (as Percent of Total Fatty Acid ± SE) | | | | | Total Fatty Acid Content (% Fresh Wt) |
|---|---|---|---|---|---|---|
| | 16:0 | 18:0 | 18:1 | 18:2 | 18:3 | |
| 395-18 self seed | 5.6 (±1.1) | 2.1 (±0.3) | 21.7 (±3.8) | 69.7 (±3.8) | 0.7 (±0.2) | 25.6 ± 5.1 |
| 395-27 self seed | 7.6 (±0.4) | 1.6 (±0.1) | 19.9 (±1.4) | 70.2 (±1.5) | 0.5 (±0.1) | 30.5 ± 3.4 |

TABLE 4-continued

The fatty acid composition of seed embryos from 395-18 and 395-27.

| Embryos From Plant Line: | Average Fatty Acid Content (as Percent of Total Fatty Acid ± SE) | | | | | Total Fatty Acid Content (% Fresh Wt) |
|---|---|---|---|---|---|---|
| | 16:0 | 18:0 | 18:1 | 18:2 | 18:3 | |
| Control[a] | 11.9 (±0.8) | 1.4 (±0.2) | 16.3 (±1.4) | 69.3 (±1.2) | 0.7 (±0.1) | 30.0 ± 4.5 |

[a]Control seed embryos were from plants regenerated from cultures transformed with a gene not involved in oil biosynthesis.

EXAMPLE 10

Biochemical Analysis of Embryos From Plants Transformed With the Plasmid pDAB395

As described previously, plants were produced which were transformed with the first soybean KAS II gene in the sense orientation relative to the globulin promoter (pDA2395). Individual zygotic embryos were dissected from R1 seed 22 to DAP and analyzed for fatty acid composition as described herein. For KAS II analysis, protein was extracted from each individual zygotic embryo of Ri seed normalized for protein concentrations (BioRAD), and analyzed using [$2^{14}$C] malonyl-CoA. The natural variation of KAS II activity was determined for the nontransformed line HiII. In addition, transformed lines which did not contain the gene of interest were also used as controls. The results are shown in Table 5.

TABLE 5

Increased KAS II activity and decreased 16:0 content in R1 seed embryos of maize plants transformed with plasmid pDAB395.

| Plant Code | Embryo's Tested | 16:0[a] Content | Synthase Activity[b] | Percent of Control[c] |
|---|---|---|---|---|
| HiII Control | 20 | 12.1 ± 1.2 | 1522 ± 96 | 100 |
| Normal 16:0 | 6 | 12.4 ± 1.1 | 1483 ± 151 | 97 |
| Low 16:0 395-18.14 x 2x7511 | 4 | 6.4 ± 1.1 | 2118 ± 80 | 139 |
| Normal 16:0 | 10 | 12.1 ± 1.8 | 1561 ± 216 | 102 |
| Low 16:0 | 10 | 4.5 ± 0.6 | 2373 ± 101 | 156 |

[a]16:0 content is percentage of total fatty acids.
[b]Synthase activity was measured by synthase-catalyzed condensation of [2-$^{14}$C]malonyl-CoA with C16:0-ACP. Numbers listed are counts per minute of radio-labeled [2-$^{14}$C]malonyl-CoA condensation of 16:0-ACP to 18:0-ACP per minute.
[c]Percent change of synthase activity as compared to the control.

A linear correlation was observed between the average palmitate (16:0) content and KAS II activity of R1 seed embryos tested. Variations were observed when examining 16:0 content in the progeny of R1 seed embryos which can be explained by the expected segregation of the globulin sense soybean KAS II transgene in this generation. The data in Table 5 summarizes the results for R1 seed embryos of line 395-18 displaying a reduced 16:0 content (characterized as below 8.0%).

The average 16:0 content of R1 seed embryos from lines 395-18 was significantly lower than the control seed embryos. The average synthase activity was also greater than the control. Again, a linear correlation was observed between 16:0 content and synthase activity.

The results described above clearly demonstrated that transformation of maize plants with a soybean KAS II gene under control of the globulin promoter resulted in a change in the fatty acid composition of seeds. Furthermore a strong correlation was observed between decreases in 16:0 content and increases in KAS II activity.

EXAMPLE 11

Southern Analysis of Transformed Callus and Plant Tissues

BASTA resistant lines transformed with various plasmids were characterized by Southern analysis to confirm the presence of the transgene using a DNA probe specific for the coding region of the gene of interest. DNA from leaf material was analyzed.

Leaf material from plants was harvested at the 6–8 leaf stage. Genomic DNA was prepared from lyophilized tissue as described by Saghai-Maroof et. al. ((1984) *Proceed. Nat. Acad. Sci. USA* 81:8014–8018). Eight µg of each DNA was digested with the restriction enzyme(s) specific for each plasmid construct using conditions suggested by the manufacturer (Bethesda Research Laboratory) and separated by electrophoresis on a 0.8% agarose gel. The DNA was then blotted onto nylon membranes as described by Southern ((1975) *J. Mol. Biol.*, 98:503–517). The radioactive probe was then hybridized to the genomic DNA on the blots in 45 mL of minimal hybridization buffer [10% polyethylene glycol, 7% SDS, 0.6×SSC, 10 mM sodium phosphate, 5 mM EDTA and 100 µg/mL denatured salmon sperm DNA] overnight at 60° C. After hybridization, blots were washed at 60° C. in 0.25×SSC and 0.2% SDS for 45 min., blotted dry and exposed to XAR-5 film (Kodak) overnight on two intensifying screens (DuPont).

Results of Southern analysis of the transformed lines is presented in Table 6.

TABLE 6

Southern Analysis of transformed plants.

| Plasmid Used for Transformation | Restriction enzymes used | Expected size hybridization product | Number of lines with the expected hybridization product |
|---|---|---|---|
| pDAB395 | KpnI / XhoI | 2.7 kb | 7 |
| pDAB397 | PstI / XbaI | 3.9 kb | 1 |

EXAMPLE 12

Purification and Characterization of Soybean KAS II Heterologously Expressed In *E. Coli*

For immunodetection, proteins were separated on 4–20% SDS-polyacrylamide gels as described, supra., transferred to ECL nitrocellulose membranes (Amersham Life Sciences, Arlington Heights, Ill.) using a Pharmacia Semi-Dry Blotter and Towbin buffer (Towbin et al., 1979 *Proc. Natl. Acad. Sci. USA* 76:4350–4354). Membranes were probed with domain-specific anti-KASII antibodies were generated against an 18 amino acid oligopeptide corresponding to amino acids 334 to 351 of SEQ ID NQ;18 (Genemed Biotechnologies, Inc. South San Francisco, Calif.). This region was distinct from KAS II proteins found in both maize and *E. coli* KAS II and KAS I. The secondary antibody was horseradish peroxidase conjugated goat anti-rabbit serum (Bio-Rad Laboratories, Hercules, Calif.). Immunoreactive polypeptides were detected using the ECL Western Blotting Detection Reagent (Amersham Life Sciences, Arlington Heights, Ill.).

KAS II was purified from *E. coli* by immunoprecipitation with domain-specific antibodies as described previously, supra. Extracts of *E. coli* cultures containing either pET26 (control) or pDAB395 (pET26 with soybean KAS II gene) were incubated with domain-specific antibodies overnight at 4° C. on an end-over-end rotator. After incubation, the supernatants were centrifuged with excess Protein A-Sepharose beads preincubated in 10 mM Tris (pH 8.0). The matrix was then added to a column and washed with 10 column volumes of 10 mM Tris, pH 8.0. KAS II was eluted with 100 mM glycine, (pH 3.0), and immediately neutralized with 1 M Tris (pH 8.0). Protein was dialyzed overnight in 25 mM sodium phosphate (pH 7.4) and then applied to a MonoQ HR 5/5 column (Pharmacia). KAS II activity was eluted using a linear gradient of 0–0.5 M LiCl in buffer B, supra., over 1 h at a flow rate of 1 mL/min. Fractions were assayed for activity and active fractions were pooled and desalted. Active fractions were analyzed by SDS-PAGE (Laemmli, 1970 *Nature* 227:680–685) on a 4–20% SDS-PAGE (Integrated Separation Systems, Woodburn, Mass). Activity correlated to a single Coomassie stained band having a denatured size of 46 kDa. Analysis of proteins obtained from pET26 expressed in *E. coli* and treated identically had no Coomassie stainable protein. Biochemical analysis of purified soybean KASII expressed in *E. coli* was performed as described herein, supra, and is shown in Table 7.

TABLE 7

Substrate specificity of immunoprecipitated purified soybean KAS II expressed in *E. coli*.

| Enzyme Source | C10:0 ACP[a] | C16:0-ACP | 50 µM cerulenin C16:0-ACP | Boiled Enzyme C16:0-ACP |
|---|---|---|---|---|
| pET26 | 82.5 ± 0.7 | 96.5 ± 30.4 | 69 ± 1.4 | 64.5 ± 14.8 |
| pDAB393 | 207.0 ± 9.9 | 1929.5 ± 2.1 | 1192 ± 11.3 | 47.0 ± 15.6 |

[a]Numbers listed are counts per minute of radio-labeled [2-$^{14}$C]malonyl-CoA condensation of either C10:0-ACP to C12:0-ACP or C16:0-ACP to C18:0-ACP per minute.

The molecular mass of native KAS II was determined by gel filtration using a Superdex 200 column (Pharmacia LKB Biotechnology, Inc.) equilibrated in 25 mM $KH_2PO_4$ (pH7.0). The column was calibrated using protein standards (BioRAD, Hercules, Calif.), which included blue dextran, thyroglobin ($M_r$, 670,000), bovine gamma globulin ($Mr_r$, 158,000), chicken ovalbumin ($M_r$, 44,000), equine myoglobin ($M_r$, 17,000), vitamin B-12 ($M_r$, 1,350). The native molecular weight of the purified heterologously expressed soybean KAS II was determined to be 82,000±5,000, as compared to a subunit size 46 kDa determined by SDS-PAGE, thus indicating that soybean KAS II functions as a homodimer.

We claim:

1. An isolated DNA construct comprising, in the 5' to 3' direction:
   a promoter regulatory element,
   a nucleic acid fragment that encodes a β-ketoacyl-acyl carrier protein synthase II isolated from maize or soybean, said nucleic acid fragment being selected from the group consisting of SEQ ID NO:5, SEQ ID NO:7, SEQ ID NO:8, SEQ ID NO:14, SEQ ID NO:16, SEQ ID NO:17, SEQ ID NO:19, SEQ ID NO:21, and SEQ ID NO:22, and
   a transcriptional terminator sequence.

2. The DNA construct of claim 1 wherein said promoter regulatory element is selected from the group consisting of ubiquitin promoter, maize globulin promoter, maize streak virus enhancer region, 35s promoter, doubly enhanced 35s promoter and the first intron of maize alcohol dehydrogenase.

3. The DNA construct of claim 1 wherein said nucleic acid fragment is in the sense orientation.

4. The DNA construct of claim 1 wherein said nucleic acid fragment is in an antisense orientation.

5. An isolated nucleic acid fragment selected from the group consisting of SEQ ID NO:1, SEQ ID NO:2, SEQ ID NO:3, SEQ ID NO:5, SEQ ID NO:7, SEQ ID NO:8, SEQ ID NO:10, SEQ ID NO:11, SEQ ID NO:12, SEQ ID NO:14, SEQ ID NO:16, SEQ ID NO:17, SEQ ID NO:19, SEQ ID NO:21, SEQ ID NO:22, SEQ ID NO:24, SEQ ID NO:25, SEQ ID NO:26, SEQ ID NO:27, and SEQ ID NO:28.

6. A DNA isolate consisting essentially of a DNA sequence encoding β-ketoacyl-acyl carrier protein synthase II isolated from maize or soybean, wherein said β-ketoacyl-acyl carrier protein synthase II has an amino acid sequence selected from the group consisting of SEQ ID NO:4, SEQ ID NO:6, SEQ ID NO:9, SEQ ID NO:13, SEQ ID NO:15, SEQ ID NO:18, SEQ ID NO:20, and SEQ ID NO:23.

7. A plant cell containing a DNA construct of claim 1.

8. The plant cell of claim 7 wherein said promoter regulatory element is selected from the group consisting of ubiquitin promoter, maize globulin promoter, maize streak virus enhancer region, 35s promoter, doubly enhanced 35s promoter and the first intron of maize alcohol dehydrogenase.

9. The plant cell of claim 7 wherein said nucleic acid fragment is in the sense orientation.

10. The plant cell of claim 7 wherein said nucleic acid fragment is in an antisense orientation.

11. The plant cell of claim 7 wherein said plant cell is selected from the group consisting of soybean, Brassicaceae sp., canola, rape, sunflower, flax, safflower, coconut, palm, olive, peanut, cotton, castor bean, coriander, Crambe sp., Cuphea sp., Euphorbia sp., Oenothera sp., jojoba, Lesquerella sp., marigold, Limnanthes sp., Vernonia sp., *Sinapis alba*, cocoa, and maize.

12. The plant cell of claim 11 wherein said plant cell is a seed embryo cell.

13. A transgenic plant produced from the plant cell of claim 7.

14. A seed, and the progeny thereof, produced from the transgenic plant of claim 13.

15. A method of producing a plant oil having altered levels of fatty acids comprising:

growing a plant cell having integrated into its genome a construct comprising, in the 5' to 3' direction, a promoter regulatory element functional in a plant cell, a nucleic acid fragment that encodes a β-ketoacyl-acyl carrier protein synthase II isolated from maize or soybean, said nucleic acid fragment being selected from the group consisting of SEQ ID NO:5, SEQ ID NO:7, SEQ ID NO:8, SEQ ID NO:14, SEQ ID NO:16, SEQ ID NO:17, SEQ ID NO:19, SEQ ID NO:21, and SEQ ID NO:22, and a transcriptional terminator sequence, wherein overexpression of β-ketoacyl-acyl carrier protein synthase II gene results in the production of altered levels of fatty acid in said plant cell.

16. The method of claim 15 wherein said plant cell is selected from the group consisting of soybean, Brassicaceae sp., canola, rape, sunflower, flax, safflower, coconut, palm, olive, peanut, cotton, castor bean, coriander, Crambe sp., Cuphea sp., Euphorbia sp., Oenothera sp., jojoba, Lesquerella sp., marigold, Limnanthes sp., Vernonia sp., *Sinapis alba*, cocoa, and maize.

17. The method of claim 15 wherein said plant cell is a seed embryo cell.

18. The method of claim 15 comprising the further step of regenerating a transgenic plant from said plant cell.

19. The method of claim 18 wherein said plant oil is isolated from said transgenic plant and the progeny thereof.

20. The method of claim 15 wherein said nucleic acid fragment is in the sense orientation.

21. The method of claim 15 wherein said nucleic acid fragment encoding is in an antisense orientation.

22. The isolated nucleic acid fragment of claim 5 selected from the group consisting of SEQ ID NO:5, SEQ ID NO:7, SEQ ID NO:8, SEQ ID NO:14, SEQ ID NO:16, SEQ ID NO:17, SEQ ID NO:19, SEQ ID NO:21, and SEQ ID NO:22.

* * * * *